US007381744B1

(12) United States Patent
Boyd

(10) Patent No.: US 7,381,744 B1
(45) Date of Patent: Jun. 3, 2008

(54) METHOD OF TREATING OSTEOPOROSIS COMPRISING VACUOLAR-TYPE (H+)-ATPASE-INHIBITING COMPOUNDS

(75) Inventor: Michael R. Boyd, Ijamsville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/914,708

(22) PCT Filed: Mar. 2, 2000

(86) PCT No.: PCT/US00/05582

§ 371 (c)(1),
(2), (4) Date: Dec. 20, 2001

(87) PCT Pub. No.: WO00/51589

PCT Pub. Date: Sep. 8, 2000

Related U.S. Application Data

(60) Provisional application No. 60/122,953, filed on Mar. 5, 1999, provisional application No. 60/169,564, filed on Dec. 8, 1999.

(51) Int. Cl.
*A61K 31/335* (2006.01)
*A61K 31/70* (2006.01)
*C07D 313/00* (2006.01)

(52) U.S. Cl. .......................... 514/450; 514/27; 514/28; 549/269; 549/270

(58) Field of Classification Search ................ 514/450, 514/27, 28, 62; 549/269, 270
See application file for complete search history.

(56) References Cited

U.S. PATENT DOCUMENTS

2002/0042079 A1* 4/2002 Simon et al. ................ 435/7.1

FOREIGN PATENT DOCUMENTS

| WO | WO 93/18652 | * | 9/1993 |
| WO | WO 99/05136 | * | 2/1999 |
| WO | WO 99/05136 A1 | | 2/1999 |
| WO | WO 99/21835 | * | 5/1999 |
| WO | WO 00/51589 A2 | | 9/2000 |
| WO | WO 00/51589 A3 | | 7/2001 |

OTHER PUBLICATIONS

Yamamoto et al., "Balfilomycin A1 Prevents Maturation of Autophagic Vacuoles by Inhibiting Fusion Between Autophagosomes and Lysosomes in Rat Hepatoma Cell Line" 1998, cell Structure and Function, 23, 33-42.*
Gagliardi et al., "5-(5,6-Dichloro-2-indolyl)-2-methoxy-2,4-pentadienamides: Novel and Selective Inhibitors of the vacuolar H+-ATPase of Osteoclasts with Bone Antiresorptive Activity" 1998, Journal of Medicinal Chemistry, 41, 1568-1573.*

Boyd et al. "The Lobatamides, Novel Cytotoxic Macrolides from Southwestern Pacific Tunicates" 1998, J. Org. Chem. 63(22), 7805-10.*
Akifusa et al., *Exp. Cell Res.*, 238, 82-89 (1998).
Aldridge et al., *J. Chem. Soc.*, 1623-1627 (1971).
Altan et al., *J. Exp. Med.*, 187, 1583-1598 (1998).
Arabshahi et al., *Tetrahedron Lett.*, 29, 10, 1099-1102 (1988).
Benderra et al., *Int. J. Onco.*, 12, 711-715 (1998).
Benslimane et al., *J. Natural Prod.*, 51, 3, 582-583 (1988).
Blair et al., *Science*, 245, 855-857 (1987).
Bowman et al., *Proc. Natl. Acad. Sci. USA*, 85, 7972-7976 (1988).
Boyd and Paull, *Drug Dev. Res.*34, 91-109 (1995).
Boyd, *Anticancer Drug Development Guide: Preclinical Screening, Clinical Trials, and Approval*(Teicher, B.A., ed.) Totowa NJ: Humana Press, Inc. pp. 23-42 (1997).
Boyd, *Current Therapy in Oncology*(Niederhuber, ed.), Philadelphia: B.C. Decker, Inc., pp. 11-22 (1993).
Boyd, *Cytotoxic Anticancer Drugs: Models and Concepts for Drug Discovery and Development*(Valeriote, F.A. et al., eds.) Amsterdam: Kluwer Academic Publishers, pp. 11-34 (1992).
Boyd: Cancer: *Principles and Practice of Oncology Updates*(DeVita, V.T., Jr., et al., eds), Philadelphia: Lippincott, 3, 11-123 (1989).
Broady et al., *J. Chem. Soc. Chem. Commun.* 708-711 (1991).
Carmeli et al., *J. Nat. Prod.*, 53, 6, 1533-1542 (1990).
Caroll et al., *Aust. J. Chem.*, 46, 825-832 (1993).
Chan et al., *Anal. Biochem.*157, 375-380 (1986).
Charan et al., *Tetrahedron*, 52, 27, 9111-9120 (19960.
Choukchou-Braham et al., *Tetrahedron Lett.*, 35, 23, 3949-3952 (1994).

(Continued)

*Primary Examiner*—Shengjun Wang
(74) *Attorney, Agent, or Firm*—Leydig, Voit & Mayer, Ltd.

(57) ABSTRACT

The present invention provides vacuolar-type (H+)-ATPase-inhibiting compounds, compositions thereof, and methods of using them to treat or prevent a condition treatable by the inhibition of a vacuolar-type (H+)-ATPase. The composition of the present invention comprises a compound of the present invention and a carrier. The method of the present invention includes administering a vacuolar-type (H+)-ATPase inhibiting-effective amount of a compound of the present invention. The compound of the present invention has formula (I) wherein $R^1$ and $R^2$ are H, saturated or unsaturated alkyl, aryl, $R^6CH_2$—, $R^6CO$—, or $R^6SO_2$—, wherein $R^6$ is H, saturated or unsaturated alkyl, or aryl; $R^3$ is H, alkyl, aryl, an oxime, or an oxime methyl ether; the aromatic ring is unsubstituted or substituted; and Z is a contiguous linker comprising a chain of 0-10 atoms which, together with the five atoms beginning with the carbon of the aromatic ring in meta-relationship with $OR^1$ and ending with the carbon directly attached to the alkyl oxygen of the lactone, integrally form a 5-17 membered ring; or a pharmaceutically acceptable salt, an ester, or a prodrug thereof.

11 Claims, 14 Drawing Sheets

OTHER PUBLICATIONS

Collins, *Cancer Chemotherapy: Principles and Practice*, 2, J.B. Lippincott, 16-31 (1990).
Copp et al., *Tetrahedron Lett.*, 30, 28, 3703-3706 (1989).
Dale et al., *J. Am. Chem. Soc.*, 95, 512-519 (1973).
D'Auria et al., *Tetrahedron*, 49, 38, 8657-8664 (1993).
David et al., *Exp. Opin. Invest. Drugs*, 4, 725-740 (1995).
Dekker et al., *J. Antibiotics*, 51, 14-20 (1998).
Doi et al., *Tetrahedron*, 50, 29, 8651-8656 (1994).
Dröse et al., *Biochemistry*, 32, 3902-3906 (1993).
Dröse et al., *J. Exp. Biol.* 200, 1-8 (1997).
Durgnat et al., *Helvetica Chim. Acta*, 76, 222-240 (1993).
Erickson et al., *J. Org. Chem.*, 62, 23, 8188-8192 (1997).
Farina et al., *Therapeutic Focus*, 4, 4, 163-172 (1999).
Faulkner et al., *Marine Nat. Prod.*9, 497-539 (1992).
Fenical et al., *Marine Tech. Soc.*, 388-394 (1974).
Finbow et al., *Biochem. J.*, 324, 697-712 (1997).
Forgac, *Physiological Rev.*, 69, 765-796 (1989).
Fu et al., *J. Am. Chem. Soc.*, 116, 12125-12126 (1994).
Furstner et al., *Tetrahedron*, 55, 8215-8230 (1999).
Fusetani et al., *Tetrahedron Lett.*, 30, 21, 2809-2812 (1989).
Gagliardi et al., *J. Med. Chem*, 41, 1883-1893 (1998).
Gagliardi et al., *J. Med. Chem.*, 41, 1568-1573 (1998).
Galinis et al., *J. Org. Chem.*, 62, 8968-8969 (19970.
Gerard et al., *J. Exp. Biol.*, 201, 21-31 (19980.
Ghosh et al., *Tetrahedron Lett.*, 39, 8803-8806 (1998).
Gordon et al., *J. Org. Chem.*, 49, 97-100 (1984).
Grever et al., *Cancer Principles and Pratice of Oncology*, 5th Ed. (Devita et al., eds.) Philadelphia: Lippincott-Raven, pp. 385-394 (1977).
Guella et al., *Helvetica Chim. Acta*, 70, 621-626 (1987).
Hall et al., *bone and Mineral*, 27, 159-166 (1994).
Hall et al., *Inflamm. Res.*, 45, 1-9 (1996).
Howard et al., *Tetrahedron Lett.*, 46, 4449-4452 (1979).
Ishii et al., *J. Antibiot.*, 48, 12-20 (1995).
Jaspars et al., *J. Org. Chem.*, 59, 3253-3255 (1994).
Jensen et al., *J. Org. Chem.*, 37, 10, 1639-1647 (1972).
Johnston et al., *J. Org. Chem.*, 13, 5, 941-944 (1970).
Kaneko et al., *Tetrahedron Lett.*, 35, 4107-4110 (1994).
Keeling et al., *Ann. New York Acad. Sci*, 834, 600-608 (1997).
Keman et al., *J. Org. Chem.*, 53. 5014-5020 (1988).
Keman et al., *Tetrahedron Lett.*, 28, 25, 2809-2812 (1987).
Kim et al., *J. Natural Prod.*, 56, 10, 1813-1816 (1993).
Kim et al., *J. Org. Chem.* 64, 153-155 (1999).
Kinoshita et al., *FEBS Lett.*, 337, 221-225 (1994).
Kinoshita et al., *FEBS Lett.*, 398, 61-66 (1996).
Kobayashi et al., *J. Natural Prod.*, 56, 5, 787-791 (1993).
Kobayashi et al., *J. Org. Chem.*, 59, 255-257 (1994).
Kobayashi et al., *Tetrahedron*, 51, 13, 3727-3736 (1995).
Kunze et al., *J. Antibiotics*, 51, 1075-1080 (1998).
Leclercq et al., *Tetrahedron Lett.*, 50,84 65-8488 (1994).
Manabe et al., *J. Cell Physiol.*, 157, 445-452 (1993).
Marquardt et al., *J. Natl. Cancer Inst.*, 83, 1098-1102 (19910.

Martinez-Zaguilan et al., *Am. J. Physiol.*, 265, C1015-C1029 (1993).
Martinez-Zaguilan et al., *Ann. NY Acad. Sci.*, 671, 478-480 (1992).
Martinez-Zaguilan et al., *Am. J. Physiol.*, 176, 196-205 (1998).
Matsunaga et al., *J. Am. Chem. Soc.*, 108, 847-849 (198).
McKee et al., *J. Org. Chem.*, 63, 7805-7810 (1998).
Mellman et al., *Ann. Rev. Biochem.*, 55, 663-699 (1986).
Mohamadi et al., *J. Computat. Chem.*, 11, 440-467 (1990).
Monks et al., *J. Natl. Cancer Inst.*, 83, 757-766 (1991).
Montcourrier et al., *Clin. Exp. Metastatis*, 15, 382-392 (1997).
Montcourrier et al., *J. Cell Sci.*, 107, 2381-2391 (1994).
Moriyama et al., *J. Biochem.*, 115, 213-218 (1994).
Murray et al., *Aust. J. Chem.*, 48, 1253-1266 (1995).
Nelson, *TIPS*, 12, 71-75 (1991).
Nishihara et al., *Biochem. Biophys. Res. Commun.*, 212, 255-262 (1995).
Oh et al., *J. Org. Chem.*, 54, 4499-4503 (1989).
Ohkuma et al., *In Vitro Cell Devel. Biol.*, 29A, 862-866 (1993).
Ohta et al., *J. Pathol.*, 185, 324-330 (1998).
Ohtani et al., *J. Org. Chem.*, 56, 1296-1297 (1991).
Parameswaran et al., *Chemical Abstracts*, 120, 600 (1994).
Paull et al., *Cancer Chemotherapeutic Agents*(Foye, ed.), Washington D.C.: American Chemical Society Books, 9-45, (1995).
Paull et al., *Cancer Res.*, 52, 3892-3900 (1992).
Perona et al., *Nature*, 334, 438-440 (1988).
Rashid et al., *J. Nat. Prod.*, 58, 7, 1120-1125 (1995).
Rochfort et al., *Aust. J. Chem.*, 49, 1217-1219 (1996).
Roesener et al., *J. Am. Chem. Soc.*, 108, 846-847 (1986).
Rovinski et al., *J. Natural Prod.*, 47, 3, 557 (1984).
Rubinstein et al., *J. Natl. Cancer Inst.*, 82, 1113-1118 (1990).
Sausville, *Anticancer Drug Development Guide: Preclinical Screening, Clinical Trials, and Approval*(Teicher, B.A., ed.) Totowa, NJ: Humana Press, Inc., pp. 217-226 (1997).
Shimojima et al., *J. Med. Chem.*, 26, 1370-1374 (1983).
Shimojima et al., *J. Med. Chem.*, 28, 3-9 (1985).
Shimojima et al., *Tetrahedron Lett.*, 23, 51, 5435-5438 (1982).
Skehan et al., *J. Natl. Cancer Inst.*, 82, 1107-1112 (1990).
Stevens et al., *Annu. Rev. Cell Dev. Bio.*, 13, 779-808 (1997).
Stinson et al., *Anticancer Res.*, 12, 1035-1054 (1992).
Stone et al., *Kindney Int.*, 33, 767-774 (1988).
Suzumura et al., *Tetrahedron Lett.*, 38, 43, 7573-7576 (1997).
Urry et al., *Tetrahedron*, 27, 3109-3114 (1966).
Vaananen et al, *J. Cell, Biol.*, 111, 1305-1311 (1990).
Venkateswarlu et al., *J. Natural Prod.*, 57, 9, 1283-1285 (1994).
Wang et al., *J. Biol. Chem.*, 265, 21957-21965 (1990).
Ward et al., *Tetrahedron*, 51, 45, 12301-12318 (1995).
Wassaman, *Science*, 235, 553-560 (1987).
Weinstein et al., *Science*, 275, 343-349 (1997).
Windholz et al., *J. Org. Chem.*, 37, 10, 1647-1651 (1972).
Wolkowski et al., *Tetrahedron Lett.*, 565-568 (1972).
Zhi et al., 11 *Plant Biochem.*, 123, 123: 193621t (1995).

\* cited by examiner

Concanamycin A

Bafilomycin A

METHOD OF TREATING OSTEOPOROSIS COMPRISING VACUOLAR-TYPE (H+)-ATPASE-INHIBITING COMPOUNDS

CROSS-REFERENCE TO RELATED PATENT APPLICATIONS

This patent application is the U.S. National Phase of PCT/US00/05582 filed on Mar. 3, 2000, which claims priority to U.S. provisional patent application No. 60/122,953 filed Mar. 5, 1999, and U.S. provisional patent application No. 60/169,564 filed Dec. 8, 1999.

TECHNICAL FIELD

The present invention relates to vacuolar-type (H+)-ATPase-inhibiting lactones, compositions, and methods of using them.

BACKGROUND OF THE INVENTION

Vacuolar (or vacuolar-type, or V-type) (H+)-ATPases have been described as "a universal proton pump of eukaryotes" (Finbour and Harrison, Biochem. J., 324, 697-712 (1997)). Vacuolar-type (H+)-ATPases are present in many tissues and cells of the body. Intracellular vacuolar (H+)-ATPase activities are present in certain organelles, and are responsible for maintaining the internal acidity thereof. This maintenance is essential for a variety of physiological functions such as: sorting of membrane and organellar proteins; proinsulin conversion; neurotransmitter uptake; cellular degradative processes; and, receptor cycling. See Mellman et al., Ann. Rev. Biochem., 55, 663-699 (1986); Forgac, Physiological Rev., 69, 765-796 (1989); Stevens and Forgac, Annu. Rev. Cell. Dev. Biol., 13, 779-808 (1997); Nelson, TIPS, 12, 71-75 (1991).

Vacuolar-type (H+)-ATPase activity is also located within specialized plasma membranes. Important examples include the vacuolar-type (H+)-ATPase activity in the plasma membranes of kidney intercalated cells, osteoclasts and sperm cells. See Stone and Xie, Kidney Int., 33, 767-774 (1988); Vaananen et al, J. Cell. Biol., 111, 1305-1311, (1990); Blair et al., Science, 245, 855-857, (1987); Wang and Gluck, J. Biol. Chem., 265, 21957-21965 (1990); Hall and Chambers, Inflamm. Res., 45, 1-9 (1996); Hall and Schaueblin, Bone and Mineral, 27, 159-166 (1994); David and Baron, Exp. Opin. Invest. Drugs, 4, 725-740 (1995); Wassarman, Science, 235, 553-560 (1987); Nelson, TIPS, 12, 71-75 (1991).

Because of the importance of vacuolar-type (H+)-ATPase activity in the maintenance of many physiological functions, compounds which inhibit vacuolar-type (H+)-ATPase will have useful pharmacological applications in a variety of different situations. See reviews by Nelson, TIPS, 12, 71-74 (1991), and Keeling et al., Ann. New York Acad. Sci, 834, 600-608 (1997), and references contained therein. For example, a given vacuolar-type (H+)-ATPase inhibitor may have utility against one or more disease states or physiological functions, in which it is desirable to inhibit an intra-organellar, vacuolar-type (H+)-ATPase-mediated process, such as acidification, accumulation of a neurotransmitter, receptor turnover, lysosomal storage, and the like. See Mellman et al., Ann. Rev. Biochem., 55, 663-699 (1986); Forgac, Physiological Rev., 69, 765-796 (1989); Stevens and Forgac, Annu. Rev. Cell. Dev. Biol., 13, 779-808 (1997); Nelson, TIPS, 12, 71-75 (1991). Similarly, a given vacuolar-type (H+)-ATPase inhibitory compound may be useful against one or more disease states or physiological functions, in which it is desirable to modify a plasma membrane vacuolar-type (H+)-ATPase-mediated process, such as urinary acidification, bone resorption, or the acrosomal acid secretion required for fertility. See Stone and Xie, Kidney Int., 33, 767-774 (1988); Vaananen et al, J. Cell. Biol., 111, 1305-1311 (1990); Blair et al., Science, 245, 855-857 (1987); Wang and Gluck, J. Biol. Chem., 265, 21957-21965 (1990); Hall and Chambers, Inflamm. Res., 45, 1-9 (1996); Hall and Schaueblin, Bone and Mineral, 27, 159-166 (1994); David and Baron, Exp. Opin. Invest. Drugs, 4, 725-740 (1995); Wassarman, Science, 235, 553-560 (1987); Nelson, TIPS, 12, 71-75, (1991).

Compounds that inhibit vacuolar-type (H+)-ATPases also will have important utility as adjuncts to cancer therapy. For example, there is literature evidence indicating involvement of vacuolar-type (H+)-ATPases in processes related to cellular proliferation, angiogenesis, tumor cell invasiveness, metastasis, and drug resistance (see, e.g., Akifusa et. al., Exp. Cell Res., 238, 82-89 (1998); Altan et al., J. Exp. Med., 187, 1583-1598 (1998); Gerard et al., J. Exp. Biol., 201, 21-31 (1998); Ishii et al., J. Antibiot., 48, 12-20 (1995); Moriyama et al., J. Biochem., 115, 213-218 (1994); Ohkuma et al., In Vitro Cell Devel. Biol., 29A, 862-866 (1993); Perona et al., Nature, 334, 438-440 (1988); Montcourrier et al., J. Cell Sci., 107, 2381-2391 (1994); Montcourrier et al., Clin. Exp. Metastatis, 15, 382-392 (1997); Martinez-Zaguilan et al., Ann. NY Acad. Sci., 671, 478-480 (1992); Martinez-Zaguilan et al., Am. J. Physiol., 265, C1015-C1029 (1993); Martinez-Zaguilan et al., J. Cell. Physiol., 176, 196-205 (1998); Nishihara et al., Biochem. Biophys. Res. Commun., 272, 255-262 (1995); Manabe et al., J. Cell Physiol., 157, 445-452 (1993); Kinoshita et al., FEBS Lett., 337, 221-225 (1994); Kinoshita et al., FEBS Lett., 398, 61-66 (1996); Ohta et al., Brit. J. Cancer, 73, 1511-1517 (1996); Ohta et al., J. Pathol., 185, 324-330 (1998); Marquardt et al., J. Natl. Cancer Inst., 83, 1098-1102 (1991); and Banderra et al., Int. J. Oncol., 12, 711-715 (1998)). Therefore, compounds that inhibit these phenomena will be useful adjuncts for cancer chemotherapy.

Among the numerous challenges faced by medicinal chemistry research is the challenge of identifying new vacuolar-type (H+)-ATPase-inhibitory leads applicable to medical treatments. Purely synthetic approaches toward the identification of novel vacuolar-type (H+)-ATPase inhibiting agents have been typically unsuccessful, partly due to the technological and human limitations inherent in laboratory synthesis. Although biological metabolites provide a vast resource of new structurally diverse chemical compounds, some of which have demonstrated biological activity, the agents available for exploiting therapeutic opportunities through inhibition of vacuolar-type (H+)-ATPase have heretofore been few. The concanamycins, for example, are among the few potent inhibitors of vacuolar-type (H+)-ATPase heretofore reported, but are structurally complex and do not provide a good template from which simpler, synthetically practical vacuolar-type (H+)-ATPase inhibitors can be prepared.

Thus, there remains a need for new vacuolar-type (H+)-ATPase inhibitors, pharmaceutical compositions, and methods of using such compounds. The present invention provides such compounds, compositions, and methods. These and other advantages of the present invention, as well as additional inventive features, will be apparent from the description of the invention provided herein.

BRIEF SUMMARY OF THE INVENTION

The present invention provides a method of preventing or treating a condition treatable by the inhibition of vacuolar-type (H+)-ATPase. The method of the present invention includes administering a vacuolar-type (H+)-ATPase inhibiting-effective amount of at least one compound of the formula:

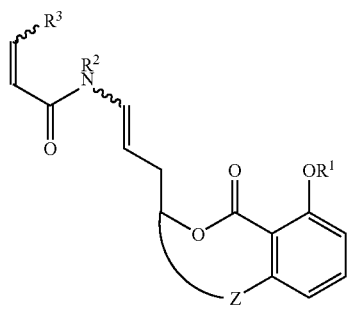

(I)

wherein $R^1$ and $R^2$ are the same or different and each is H, a straight-chain or branched saturated or unsaturated alkyl, an aryl, $R^6CH_1-$, $R^6CO-$, or $R^6SO_2-$, wherein $R^6$ is H, a straight-chain or branched saturated or unsaturated alkyl, or an aryl; $R^3$ is H, a straight-chain or branched saturated or unsaturated alkyl, an aryl, an oxime, or an oxime methyl ether; the saturated alkyl, the unsaturated alkyl, and the aryl defined in $R^1$-$R^3$ and $R^6$ can be unsubstituted or substituted; the aromatic ring of formula (I) is unsubstituted or substituted with at least one substituent selected from the groups consisting of a halogen, a nitro, an amino, a hydroxyl, a thio, an acyl, an alkyl, and a cyano; and Z is a contiguous linker comprising a chain of 0-12 atoms (including heteroatoms) which atoms, together with the five atoms beginning with the carbon of the aromatic ring of formula (I) in meta-relationship with $OR^1$ and ending with the carbon directly attached to the alkyl oxygen of the lactone, which carbons are covalently bonded to either end of linker Z, integrally form a 5-17 membered ring; or a pharmaceutically acceptable salt, an ester, or a prodrug thereof. The compound(s) used in accordance with the present invention can be administered alone or in combination with a therapeutically effective amount of at least one additional vacuolar-type (H+)-ATPase inhibitor, other than a compound of the present invention.

DETAILED DESCRIPTION OF THE INVENTION

Figure 2:
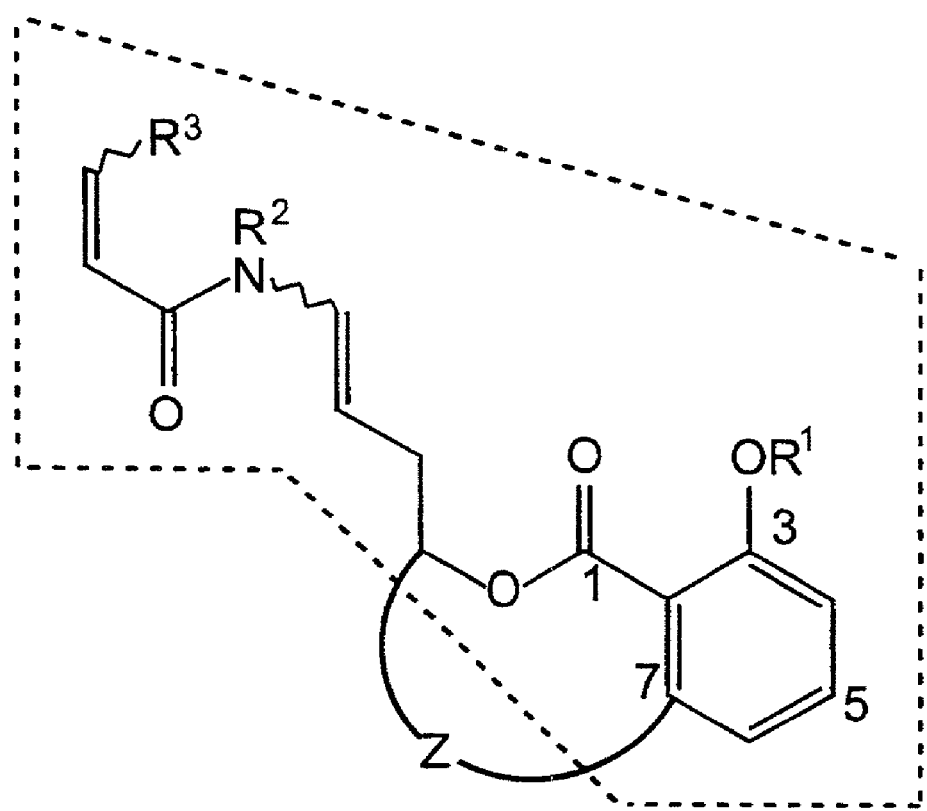
FIG. 2 illustrates a structural component motif for compounds of the present invention.

Highlighted in FIG. 2 (by the regions encompassed within the dotted lines) is the structural component motif shared by the compounds of the present invention. Surprisingly and unexpectedly it has been found that compounds possessing the structural component motif highlighted in FIG. 2 have vacuolar-type (H+)-ATPase inhibiting activity. The structural component motif represented in FIG. 2 provides a practical template that can be used to produce a vast number of structurally diverse, yet synthetically accessible vacuolar-type (H+)-ATPase inhibitors.

Accordingly, the present invention provides vacuolar-type (H+)-ATPase-inhibiting compounds, compositions thereof, and a method of inhibiting vacuolar-type (H+)-ATPase using one or more of such compounds or compositions, preferably those that include the structural component motif highlighted in FIG. 2. The present inventive method of inhibiting vacuolar-type (H+)-ATPase can be utilized in a variety of therapeutic and non-therapeutic applications, for example, as a control in diagnostic kits, bioassays, or the like, but is preferably applied therapeutically toward the treatment or prevention of a condition (e.g., an abnormal condition or a disease) treatable by the inhibition of vacuolar-type (H+)-ATPase. Thus, in a preferred embodiment, the present invention provides a method of treating or preventing a condition or disease treatable by the inhibition of vacuolar-type (H+)-ATPase, which method includes administering a vacuolar-type (H+)-ATPase inhibiting-effective amount of a compound that includes the structural component highlighted in FIG. 2. More preferably, the present inventive method of treating or preventing a condition treatable by the inhibition of vacuolar-type (H+)-ATPase includes administering a vacuolar-type (H+)-ATPase inhibiting-effective amount of at least one compound of the formula:

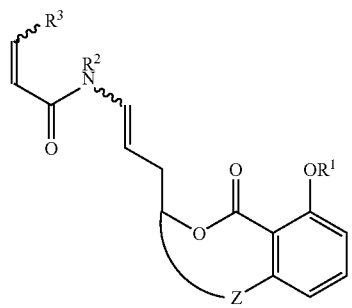

(I)

wherein $R^1$ and $R^2$ are the same or different and each is H, a straight-chain or branched saturated or unsaturated alkyl, an aryl, $R^6CH_2$—, $R^6CO$—, or $R^6SO_2$—, wherein $R^6$ is H, a straight-chain or branched saturated or unsaturated alkyl or an aryl; $R^3$ is H, a straight-chain or branched saturated or unsaturated alkyl, an aryl, an oxime, or an oxime methyl ether; the saturated alkyl, the unsaturated alkyl and the aryl defined in $R^1$-$R^3$ and $R^6$ can be unsubstituted or substituted with at least one substituent selected from the group consisting of a halogen, a nitro, an amino, a hydroxyl, a thio, an acyl, an alkyl, and a cyano; the aromatic ring of formula (I) is unsubstituted or substituted with a substituent selected from the group consisting of a halogen, a nitro, an amino, a hydroxyl, a thio, an acyl, an alkyl, and a cyano; and Z is a contiguous linker comprising a chain of 0-12 atoms (including heteroatoms) which atoms, together with the five atoms beginning with the carbon of the aromatic ring of formula (I) in meta-relationship with $OR^1$ and ending with the carbon directly attached to the alkyl oxygen of the lactone, which carbons are covalently bonded to either end of linker Z, integrally form a 5-17 membered ring; or a pharmaceutically acceptable salt, an ester, or a prodrug thereof. The compound(s) of the present invention can be administered alone, or in combination with a therapeutically effective amount of at least one additional compound other than a compound of the present invention.

The compounds of the present invention can be obtained by one of ordinary skill in the art by isolation from natural sources; chemical synthesis using well-known and readily available chemical reactions, reagents, and procedures; by semisynthesis; or the like.

In one embodiment, the present invention provides a method of treating or preventing a condition treatable by the inhibition of vacuolar-type (H+)-ATPase, which method includes administering a vacuolar-type (H+)-ATPase inhibiting-effective amount of a compound of Formula (I), wherein Z is a contiguous linker comprising a chain of 7-12 atoms which (including heteroatoms) integrally form a 12-17 membered ring. Examples of such compounds include, for example, compounds of the formula:

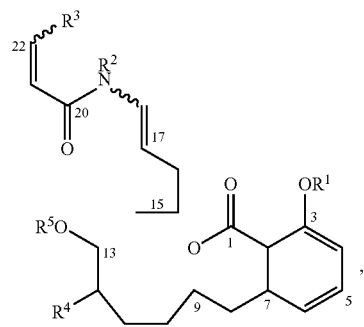

(IA)

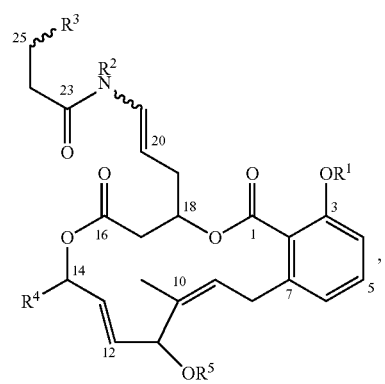

(IB)

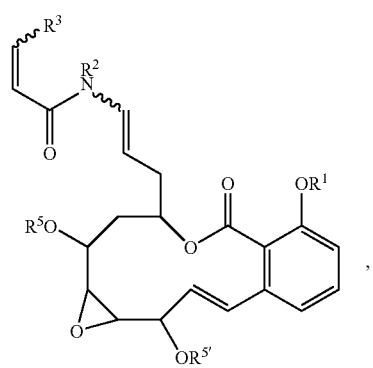

(IC)

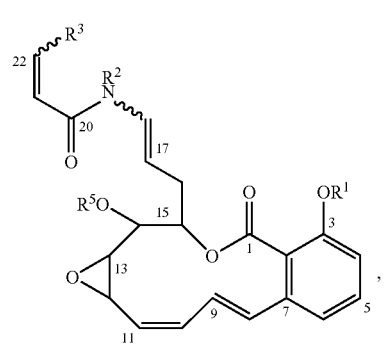

(ID)

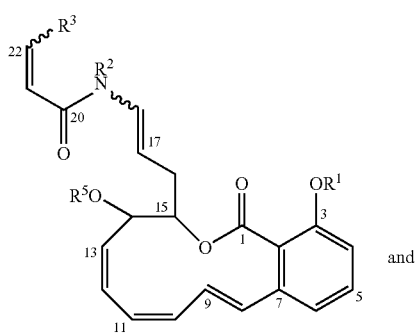

(IE)

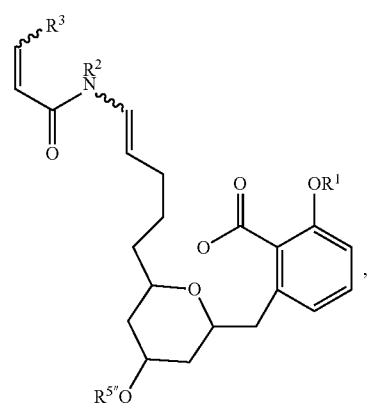

(IF)

wherein $R^1$ and $R^2$ are the same or different and each is H, a straight-chain or branched saturated or unsaturated alkyl, an aryl, $R^6CH_2$—, $R^6CO$—, or $R^6SO_2$—, wherein $R^6$ may be H, a straight-chain or branched saturated or unsaturated alkyl or an aryl; $R^3$ is H, a straight-chain or branched saturated or unsaturated alkyl, an aryl, an oxime, or an oxime methyl ether; $R^4$ is H, an alkyl, or $R^7CH_2$—, wherein $R^7$ is $R^6O$—, $R^6CO_2$—, or $R^6SO_3$—; $R^5$, $R^{5'}$ and $R^{5''}$ are the same or different and each is H, a straight-chain or branched saturated or unsaturated alkyl, an aryl, a glycoside, $R^6CH_2$—, $R^6CO$—, or $R^6SO_2$—; the saturated alkyl, unsaturated alkyl and aryl defined in $R^1$-$R^3$, $R^5$, $R^{5'}$, $R^{5''}$ and $R^6$, and the alkyl defined in $R^4$, are unsubstituted or substituted with at least one substituent selected from the group consisting of a halogen, a nitro, an amino, a hydroxyl, a thio, an acyl, an alkyl, and a cyano; and the aromatic ring of formula (I) is unsubstituted or substituted with at least one substituent selected from the group consisting of a halogen, a nitro, an amino, a hydroxyl, a thio, an acyl, an alkyl, and a cyano; pharmaceutically acceptable salts, esters, and prodrugs thereof.

The term "saturated alkyl" means a straight-chain or branched-chain saturated alkyl which, unless otherwise specified, contains from about 1 to about 20 carbon atoms, preferably from about 1 to about 10 carbon atoms, more preferably from about 1 to about 8 carbon atoms, and most preferably from about 1 to about 6 carbon atoms. Examples of saturated alkyls include methyl, ethyl, propyl, isopropyl, n-butyl, sec-butyl, isobutyl, tert-butyl, pentyl, isoamyl, hexyl, octyl, dodecanyl, and the like. Saturated alkyl substituents can be unsubstituted or substituted, for example, with at least one substituent selected from the group consisting of a halogen, a nitro, an amino, a hydroxyl, a thio, an acyl, an alkyl, and a cyano.

The term "unsaturated alkyl" means saturated alkyl (straight-chain or branched-chain), as defined herein, in which one or more of the single carbon-carbon bonds thereof is instead a multiple bond, for example, a double or a triple bond. Thus, unsaturated alkyls include alkenyl and alkynyl substituents, as well as substituents that have a combination of double and triple bonds. The term "alkenyl" means a straight-chain or branched-chain alkenyl having one or more double bonds. Unless otherwise specified, the alkenyl can contain from about 2 to about 20 carbon atoms, preferably from about 2 to about 10 carbon atoms, more preferably from about 2 to about 8 carbon atoms, and most preferably from about 2 to about 6 carbon atoms. Examples of alkenyls include vinyl, allyl, 1,4-butadienyl, isopropenyl, and the like. The term "alkynyl" means a straight-chain or branched-chain alkynyl radical having one or more triple bonds. Unless otherwise specified, alkynyls can contain from about 2 to about 20 carbon atoms, preferably from about 2 to about 10 carbon atoms, more preferably from about 2 to about 8 carbon atoms, and most preferably from about 2 to about 6 carbon atoms. Examples of alkynyls include ethynyl, propynyl (propargyl), butynyl, and the like. Unsaturated alkyl substituents can be unsubstituted or substituted, for example, with at least one substituent selected from the group consisting of a halogen, a nitro, an amino, a hydroxyl, a thio, an acyl, an alkyl, and a cyano.

Unless otherwise specified, unsaturated alkyls, as defined herein, can contain from about 2 to about 20 carbon atoms, preferably from about 2 to about 10 carbon atoms, more preferably from about 2 to about 8 carbon atoms, and most preferably from about 2 to about 6 carbon atoms. Unsaturated alkyl substituents can be unsubstituted or substituted, for example, with at least one substituent selected from the group consisting of a halogen, a nitro, an amino, a hydroxyl, a thio, an acyl, an alkyl, and a cyano.

The term "aryl" means an aromatic carbocyclic radical, as commonly understood in the art, and includes monocyclic and polycyclic aromatics such as, for example, phenyl and naphthyl rings. Preferably, the aryl comprises one or more six-membered rings including, for example, phenyl, naphthyl, and biphenyl. Aryl substituents can be unsubstituted or substituted, for example, with at least one substituent selected from the group consisting of a halogen, a nitro, an amino, a hydroxyl, a thio, an acyl, an alkyl, and a cyano.

The term "glycoside" means a substituent that yields on hydrolysis a sugar, for example glucose, galactose, amino sugars (e.g., D-glucosamine and N-acetyl-β-glucosamine), and the like.

Compounds of Formula (IA) and Formula (IB), examples of which are disclosed in U.S. Patent Application Ser. No. 60/122,953, and are given the trivial names salicylihalamides and lobatamides, respectively. Examples of vacuolar-type (H+)-ATPase inhibiting compounds of Formula (IA) or (IB) include compounds of the formula:
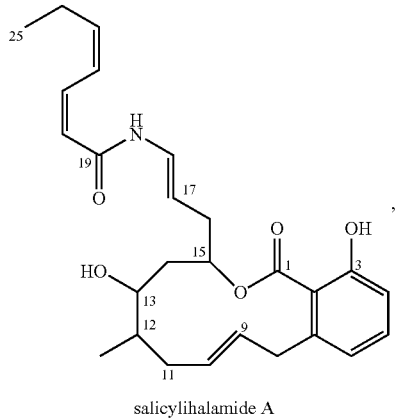
salicylihalamide A
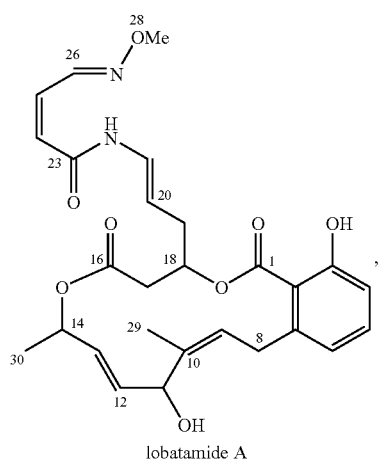
lobatamide A
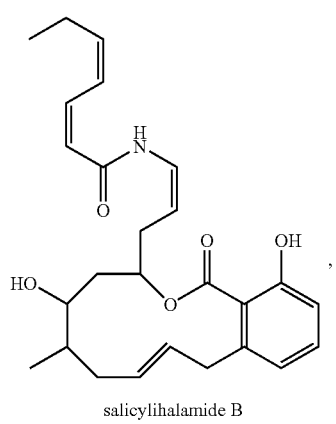
salicylihalamide B
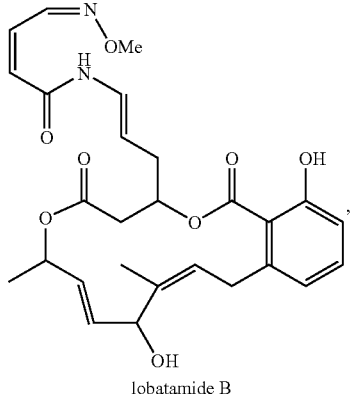
lobatamide B
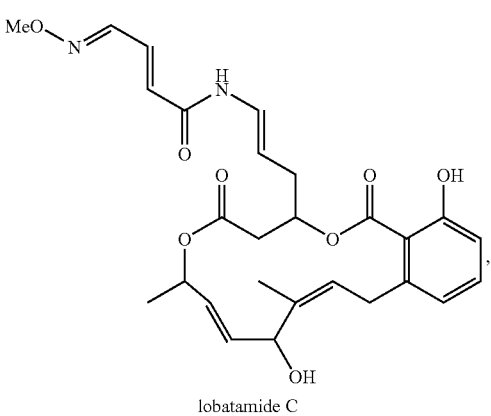
lobatamide C
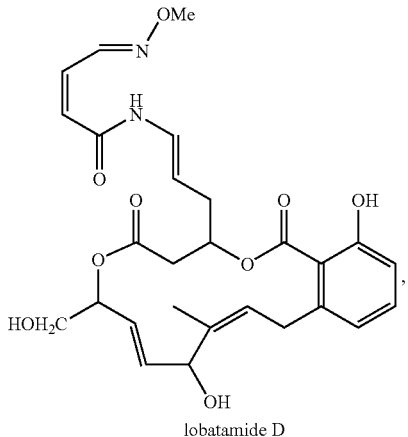
lobatamide D
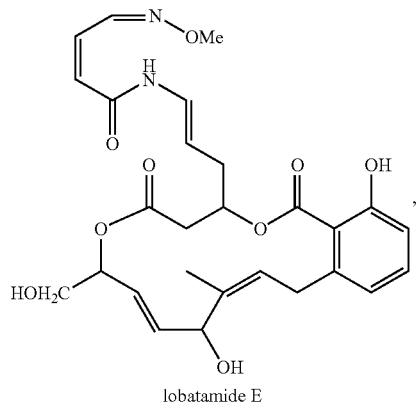
lobatamide E -continued

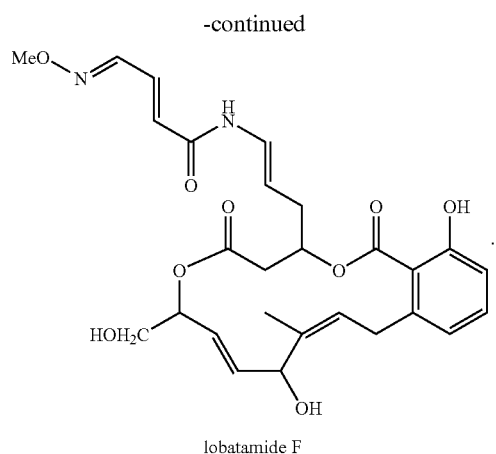

lobatamide F

The structure and absolute stereochemistry of salicylihalamide A are illustrated in FIG. 4.

Examples of vacuolar-type (H+)-ATPase inhibiting compounds of formulae (IC)-(IE) include compounds of the formula:

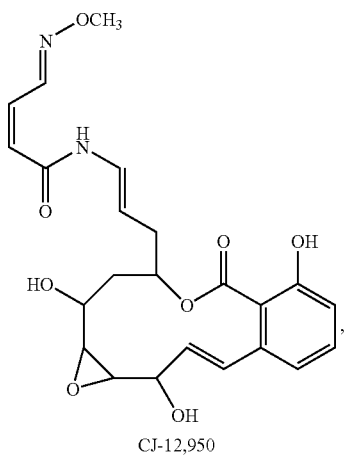

CJ-12,950

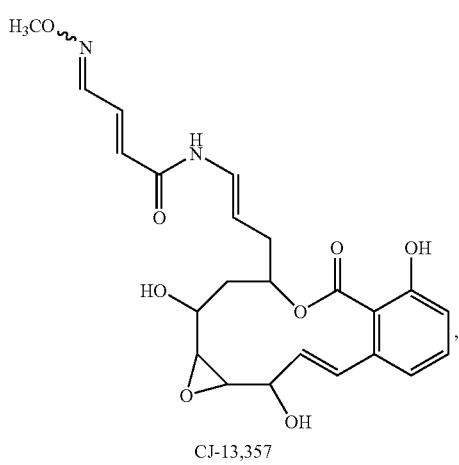

CJ-13,357

-continued

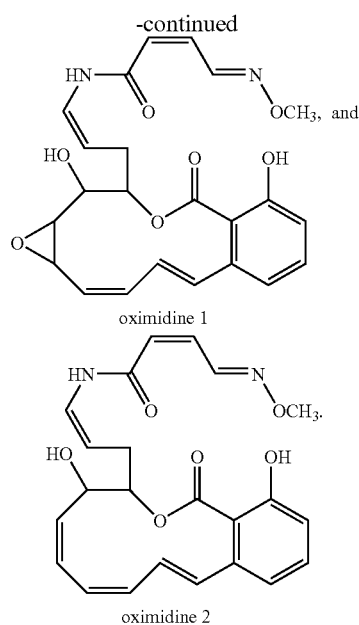

oximidine 1 oximidine 2

The compounds designated as CJ-12,950 and CJ-13,357 are described in Dekker at al., *J. Antibiotics*, 51, 14-20 (1998). Oximidines 1 and 2 are described in Kim et al., *J. Org. Chem.*, 64, 153-155 (19-99).

Examples of vacuolar-type (H+)-ATPase inhibiting compounds of formula (IF) include compounds of the formula:

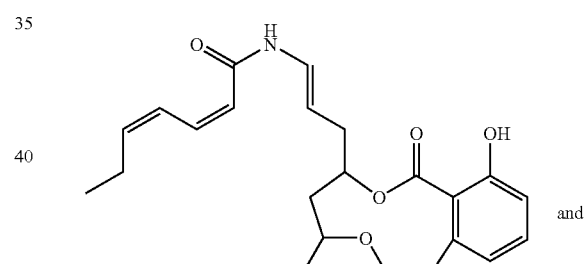

apicularen A

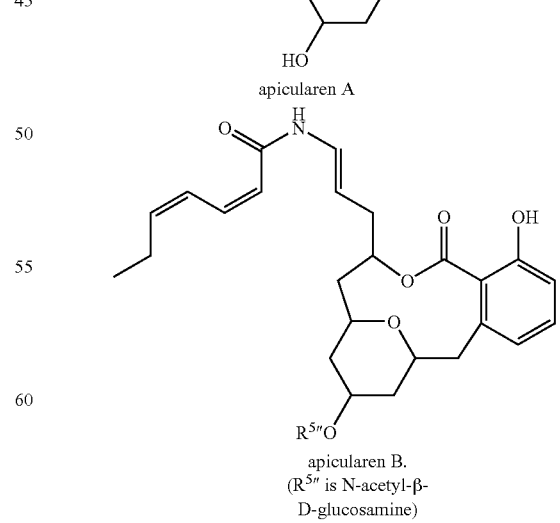

apicularen B.
($R^{5''}$ is N-acetyl-β-D-glucosamine)

Apicularens A and B are described in Kunze et al., *J. Antibiotics,* 51, 1075-1080 (1998).

In another embodiment, the present invention provides a method of treating or preventing a condition treatable by the inhibition of vacuolar-type (H+)-ATPase, which method includes administering a vacuolar-type (H+)-ATPase inhibiting-effective amount of at least one compound of Formula (I), wherein $R^1$-$R^3$ and $R^6$ are as defined herein, and Z is a contiguous linker comprising a chain of 0-6 atoms (including heteroatoms) which atoms, together with the five atoms beginning with the carbon of the aromatic ring of formula (I) in meta-relationship with $OR^1$ and ending with the carbon directly attached to the alkyl oxygen of the lactone, which carbons are covalently bonded to either end of linker Z, integrally form a 5-11 membered ring; or a pharmaceutically acceptable salt, an ester, or a prodrug thereof.

When Z is a contiguous linker comprising a chain of 0-6 atoms, the compound used in accordance with the present invention preferably is selected from the group consisting of:

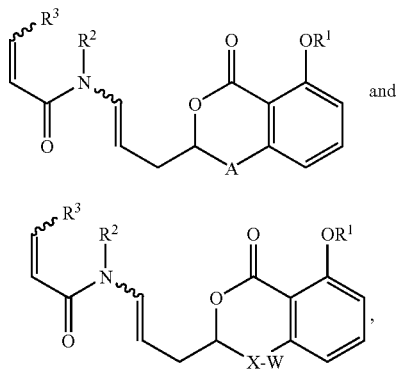

wherein $R^1$-$R^3$ are as defined herein; A is a covalent bond or a $C_1$-$C_6$ straight-chain saturated or unsaturated alkyl linker which is unsubstituted or is substituted with a one or more substituents selected from the group consisting of a halogen, a nitro, an amino, a hydroxyl, a thio, an acyl, an alkyl, and a cyano; X is a covalent bond or a $C_1$-$C_5$ straight-chain saturated or unsaturated alkyl linker which is unsubstituted or is substituted with a one or more substituents selected from the group consisting of a halogen, a nitro, an amino, a hydroxyl, a thio, an acyl, an alkyl, and a cyano; and W is O, S, C(O), C(S), S(O)$_n$, or N—$R^4$, wherein $R^4$ is H, a straight-chain or branched saturated or unsaturated alkyl, an aryl, $R^6CH_2$—, $R^6CO$—, or $R^6SO$—, $R^6$ is as defined in herein, and n is an integer from 0-2; or a pharmaceutically acceptable salt, an ester, or a prodrug thereof.

Compounds of formula (IG) or (IH) include, for example, compounds of the formula:

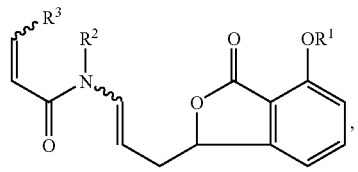

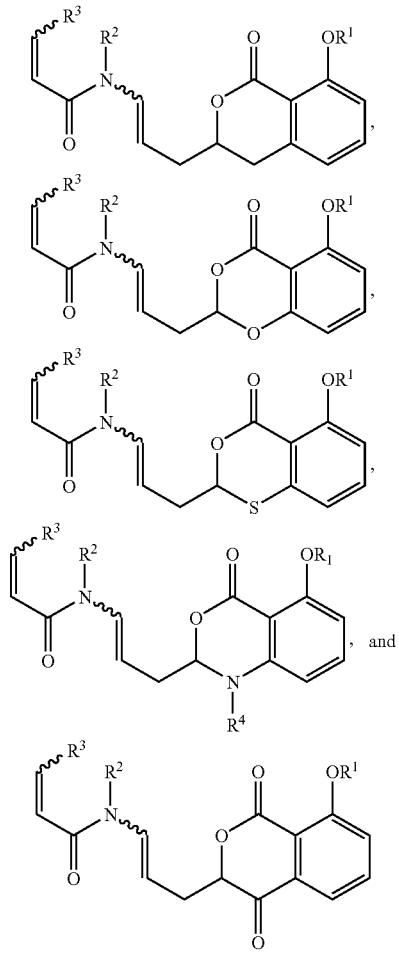

wherein $R^1$-$R^3$ are as defined herein; pharmaceutically acceptable salts, esters, and prodrugs thereof.

As indicated above, the compounds the present invention all share the structural component motif highlighted in FIG. 2. The compounds of the present invention are expected to possess vacuolar-type (H+)-ATPase inhibitory activity over a wide range of ring sizes, substitution patterns, structural variations, and the like. Indeed, compounds such as lobatamides A-F and salicylihalamides A and B exemplify compounds that incorporate the structural component motif highlighted in FIG. 2 and maintain potent vacuolar-type (H+)-ATPase inhibitory activity over a range of ring sizes (e.g., ranging from 12-15 members) and over a range of structural variations (e.g., variations in the structure of linker Z for salicylihalamide A versus lobatamide A).

The vacuolar-type (H+)-ATPase inhibiting compounds and compositions of the present invention can be used medically to regulate biological phenomena including, but not limited to: intra-organellar acidification of intracellular organelles; urinary acidification; bone resorption; fertility; angiogenesis; cellular invasiveness (e.g., tumor cell invasiveness); metastasis; and the development of drug resistance in tumor cells. Thus, the compounds of the present invention are useful in the treatment of diseases which can be controlled by the inhibition of vacuolar-type (H+)-ATPase. Such diseases include, for example, osteoporosis (see, e.g., Keeling et al., *Ann. New York Acad. Sci.,* 834, 600-608

(1997)), Alzheimer's disease, glaucoma, and abnormal urinary acidification (see, e.g., Nelson, *TIPS,* 12, 71-75 (1991)). Moreover, the vacuolar-type (H+)-ATPase inhibitors of the present invention can be used in the treatment or prevention of diseases which utilize an acid-promoted cell penetration mechanism. For example, the compounds of the present invention can be used to inhibit the entry of viruses (e.g., baculoviruses and retroviruses), or to inhibit the entry of protein toxins (e.g., diphtheria toxin), into cells (see, e.g., Mellman et al., *Ann. Rev. Biochem.,* 55, 663-699 (1986)). The compounds of the present invention also can be used to inhibit fertility in an animal, for example, a human (see, e.g., Wassarman, *Science,* 235, 553-560 (1987)), or to inhibit the invasiveness or metastasis of tumor cells, or to promote the sensitivity of cancer toward drugs by inhibiting the ability of cancer cells to develop resistance to drugs, thereby facilitating and/or making possible the chemotherapeutic treatment of cancer (see, e.g., Marquardt and Center, *J. Natl. Cancer Inst.,* 83, 1098-1102 (1991)).

The vacuolar-type (H+)-ATPase inhibiting compounds of the present invention can be included in a composition, e.g., a pharmaceutical composition. The composition can be produced by combining one or more compounds of the present invention with an appropriate pharmaceutically acceptable carrier, and can be formulated into a suitable preparation. Suitable preparations include, for example, preparations in solid, semi-solid, liquid, or gaseous forms such as tablets, capsules, powders, granules, ointments, solutions, suppositories, injections, inhalants, and aerosols, and other formulations known in the art for their respective routes of administration. In pharmaceutical dosage forms, a compound of the present invention can be used alone or in appropriate association, as well as in combination, with other pharmaceutically active compounds, including other vacuolar-type (H+)-ATPase inhibiting compounds, as described herein.

Any suitable carrier can be utilized. Suitable carriers include pharmaceutically or physiologically acceptable carriers. The following methods and carriers are merely exemplary and are in no way limiting. In the case of oral preparations, a compound of the present invention can be administered alone or in combination with a therapeutically effective amount of at least one other compound. Compositions used in accordance with the present invention can further include at least one additional compound other than a compound of the present invention, for example, an additional vacuolar-type (H+)-ATPase inhibitor (e.g., a concanamycin or a bafilomycin) or even an anticancer agent. The active ingredient(s) can be combined, if desired, with appropriate additives to make tablets, powders, granules, capsules, or the like.

Suitable additives can include, for example, conventional additives such as lactose, mannitol, corn starch or potato starch. Suitable additives also can include binders, for example, crystalline cellulose, cellulose derivatives, acacia, corn starch, or gelatins; disintegrants, for example, corn starch, potato starch or sodium carboxymethylcellulose; with lubricants such as talc or magnesium stearate. If desired, other additives such as, for example, diluents, buffering agents, moistening agents, preservatives, and/or flavoring agents, and the like, can be included in the composition.

The compounds used in accordance with the present invention can be formulated into a preparation for injection by dissolution, suspension, or emulsification in an aqueous or nonaqueous solvent, such as vegetable oil, synthetic aliphatic acid glycerides, esters of higher aliphatic acids, or propylene glycol (if desired, with conventional additives such as solubilizers, isotonic agents, suspending agents, emulsifying agents, stabilizers, and preservatives). The compounds of the present invention also can be made into an aerosol formulation to be administered via inhalation. Such aerosol formulations can be placed into pressurized acceptable propellants such as dichlorodifluoromethane, propane, nitrogen, and the like.

The compounds of the present invention can be formulated into suppositories by admixture with a variety of bases such as emulsifying bases or water-soluble bases. The suppository formulations can be administered rectally, and can include vehicles such as cocoa butter, carbowaxes, and polyethylene glycols, which melt at body temperature, but are solid at room temperature.

Unit dosage forms for oral or rectal administration such as syrups, elixirs, and suspensions can be provided wherein each dosage unit, e.g., teaspoonful, tablespoonful, tablet, or suppository contains a predetermined amount of the composition containing the compound of the present invention. Similarly, unit dosage forms for injection or intravenous administration can comprise a composition as a solution in sterile water, normal saline, or other pharmaceutically acceptably carrier.

The term "unit dosage form" as used herein refers to physically discrete units suitable as unitary dosages for human and animal subjects, each unit containing a predetermined quantity of at least one compound or compounds of the present invention (alone or, if desired, in combination with another therapeutic agent). The unit dosage can be determined by methods known to those of skill in the art, for example, by calculating the amount of active ingredient sufficient to produce the desired effect in association with a pharmaceutically acceptable carrier. The specifications for the unit dosage forms that can be used in accordance with the present invention depend on the particular effect to be achieved and the particular pharmacodynamics associated with the compound(s) in the individual host.

Pharmaceutically acceptable carriers, for example, vehicles, adjuvants, excipients, or diluents, are accessible to those of skill in the art and are typically available commercially. One skilled in the art can easily determine the appropriate method of administration for the exact formulation of the composition being used. Any necessary adjustments in dose can be readily made by a skilled practitioner to address the nature or severity of the condition being treated. Adjustments in dose also can be made on the basis of other factors such as, for example, the individual patient's overall physical health, sex, age, prior medical history, and the like.

In one embodiment, the method of the present invention includes co-administering a therapeutically effective amount of at least compound of the present invention in combination with a therapeutically effective amount of at least one additional compound other than a compound of the present invention. For example, a compound of the present invention can be co-administered with an additional vacuolar-type (H+)-ATPase inhibitor (e.g., a concanamycin or a bafilomycin), or with an anticancer agent (e.g., to inhibit the development of cancer cell resistance to the anticancer agent).

The compounds of the present invention can be administered by any suitable route including, for example, oral administration, intramuscular administration, subcutaneous, intravenous administration, or the like. For example, one or more vacuolar-type (H+)-ATPase inhibitors of the present invention (or a composition thereof) can be administered as a solution that is suitable for intravenous injection or infusion, a tablet, a capsule, or the like, or in any other suitable composition or formulation as described herein.

The vacuolar-type (H+)-ATPase "inhibiting-effective amount" is the dose necessary to achieve a vacuolar-type (H+)-ATPase "inhibiting-effective level" of the active compound in an individual patient. The vacuolar-type (H+)-ATPase inhibiting-effective amount can be defined, for example, as that amount required to be administered to an individual patient to achieve a vacuolar-type (H+)-ATPase inhibiting-effective blood level, tissue level, and/or intracellular level of a compound of the present invention to effect the desired medical treatment.

When the effective level is used as the preferred endpoint for dosing, the actual dose and schedule can vary depending, for example, upon interindividual differences in pharmacokinetics, drug distribution, metabolism, and the like. The effective level also can vary when one or more compounds of the present invention are used in combination with other therapeutic agents, for example, one or more additional vacuolar-type (H+)-ATPase inhibitors, anticancer compounds, or a combination thereof. Moreover, the effective level can vary depending upon the disease for which treatment is desired. For example, the effective level for the treatment of osteoporosis may vary relative to the effective level required for the treatment of abnormal urinary acidification, or for the inhibition of fertility.

Some compounds of the present invention, for example, certain 12 and 15 membered ring species, are known to possess potent antitumor activity (see, e.g., McKee et al., *J. Org. Chem.*, 63, 7805-7810 (1998), and International Publication No. WO 99/05136). To the extent that the compounds used in accordance with the present invention have anticancer activity, the effective blood level can be determined by analogy based on the effective blood level corresponding to anticancer activity. The effective level can be chosen, for example, as that level (e.g., $10^{-11}$-$10^{-7}$M from Example 4 herein) effective to inhibit the proliferation of tumor cells in a screening assay. Similarly, the effective level can be determined, for example, on the basis of the blood or tissue level in a patient that corresponds to a concentration of a therapeutic agent that effectively inhibits the growth of human cancers in an assay that is clinically predictive of anticancer activity. Further, the effective level can be determined, for example, based on a concentration at which certain markers of cancer in a patient's blood are inhibited by a particular compound that inhibits cancer. Alternatively, the effective level can be determined, for example, based on a concentration effective to slow or stop the growth of a patient's cancer, cause a patient's cancer to regress or disappear, render a patient asymptomatic to a particular cancer, or improve a cancer patient's subjective sense of condition. The anticancer effective level can then be used to approximate (e.g., by extrapolation), or even to determine, the level which is required clinically to achieve a vacuolar-type (H+)-ATPase inhibiting-effective blood, tissue, and/or intracellular level to effect the desired medical treatment. It will be appreciated that the determination of the therapeutically effective amount clinically required to effectively inhibit vacuolar-type (H+)-ATPase activity requires consideration of other variables that can influence the effective level, as discussed herein. When a fixed effective amount is used as a preferred endpoint for dosing, the actual dose and dosing schedule for drug administration can vary for each patient depending upon factors that include, for example, inter-individual differences in pharmacokinetics, drug disposition, metabolism, whether other drugs are used in combination, or other factors described herein that effect the effective level.

One skilled in the art can readily determine the appropriate dose, schedule, or method of administering a particular formulation, in order to achieve the desired effective level in an individual patient. One skilled in the art also can readily determine and use an appropriate indicator of the effective level of the compounds of the present invention. For example, the effective level can be determined by direct analysis (e.g., analytical chemistry) or by indirect analysis (e.g., with clinical chemistry indicators) of appropriate patient samples (e.g., blood and/or tissues). The effective level also can be determined, for example, by direct or indirect observations such as urine acidity, change in bone density, decrease in ocular pressure, or by the shrinkage or inhibition of growth of a tumor in a cancer patient (e.g., if the compound in question has anticancer activity). There are many references in the art that describe the protocols used in administering active compounds to a patient in need thereof. For example, the protocols used in the administration of anticancer agents to patients are described in "Cancer Chemotherapy: Principles and Practice" ed., Chabner and Collins, J. B. Lippincott, 1990, especially chapter 2, by J. B. Collins.

The method of the present invention can be made more effective by administering other compounds, such as, for example, another vacuolar-type (H+)-ATPase inhibitor (e.g., a concanamycin and/or a bafilomycin), along with a compound of the present invention. The compounds of the present invention also can be co-administered with an anticancer agent, in which case the effective level desirably is the level needed to inhibit the ability of the cancer to develop resistance to the anticancer agent. Suitable anticancer compounds include, for example, all of the known anticancer compounds approved for marketing in the United States, and those that will become approved in the future, for which drug resistance thereto can be controlled by the inhibition of vacuolar-type (H+)-ATPase.

The unique vacuolar-type (H+)-ATPase inhibitory activity of the compounds of the present invention can be determined using any suitable method known in the art, for example, assay methods. A suitable assay method for measuring vacuolar-type (H+)-ATPase inhibitory activity is described, for example, in Chan et al., *Anal. Biochem.*, 157, 375-380 (1986).

Alternatively, the unique vacuolar-type (H+)-ATPase inhibitory activity of the compounds of the present invention can be demonstrated using the U.S. National Cancer Institute's (NCI)'s 60 cell-line, human tumor, disease-oriented screen, which can accurately predict the anticancer activity of chemical compounds. Significantly, the NCI 60 cell-line screen also is a powerful tool that can be used to predict other types of biological activity, not limited to anticancer activity. In particular, the NCI 60 cell-line screen can be used to accurately predict vacuolar-type (H+)-ATPase inhibitory activity (see U.S. Patent Application Ser. No. 60/122,953). The NCI 60 cell-line human tumor screen, and its application in determining anticancer activity in connection with the compounds disclosed herein, is described in International Patent Application No. WO 99/05136.

The prediction of biological activity is based on the correlation of activity patterns generated in the NCI screen by compounds having known activity. The compounds compared in the correlation need not have particularly potent anticancer activity in order to display an activity pattern suitable for correlation in the NCI screen. Interestingly, compounds need not be structurally similar to one another in order correlate with each other in the NCI screen. Even if two structurally dissimilar compounds correlate strongly with each other in the NCI screen, they can be accurately predicted to have the same biological activity as each other in virtually any application, including non-cancer applications. For reviews pertinent to the NCI 60 cell-line screen, see Boyd, In: *Current Therapy in Oncology* (Niederhuber, ed.), Philadelphia: B. C. Decker, Inc., 1993, pp. 11-22; Boyd and Paull, *Drug Dev. Res.*, 34, 91-109 (1995); Grever and Chabner, In: *Cancer Principles and Practice of Oncology*, 5th Ed. (DeVita et al., eds.), Philadelphia: Lippincott-Raven, 1977, pp. 385-394; Paull et al., In: *Cancer Chemotherapeutic Agents* (Foye, ed.), Washington, D.C.: American Chemical Society Books, 1995, pp. 9-45; and Weinstein et al., *Science*, 275, 343-349 (1997).

The NCI 60 cell-line human tumor screen measures the ability of a compound to selectively kill or inhibit the growth of diverse human cancers. Generally, in the NCI screen, the compounds of the present invention display potent activity against certain types of human solid tumors (e.g., non-small cell lung cancer, renal cancer, and melanoma), and resistant strains thereof. By these observations, and with other detailed analyses of the characteristic tumor cellular response profiles, it can be shown that the compounds of the present invention have a uniquely characteristic bioactivity profile.

The NCI 60 cell-line human tumor primary screen also provides a means by which to identify natural sources of compounds. The NCI screen was designed and implemented during 1985-1990 under the direction, close scrutiny, and supervision of several internationally comprised and renowned extramural (non-NCI) advisory and review groups, including the NCI Division of Cancer Treatment's Board of Scientific Counselors, an Ad Hoc Expert Review-Committee thereof, the National Cancer Advisory Board, and the President's Cancer Panel (see Boyd, In: *Anticancer Drug Development Guide Preclinical Screening, Clinical Trials, and Approval* (Teicher, B. A., ed.), Totowa, N.J.: Humana Press, Inc., pp. 23-42, 1997). The impetus for development of the NCI screen was the international recognition that most of the commercially available anticancer drugs worldwide are essentially inactive or only transiently active against most forms of human cancer. Reviews are disclosed, for example, in Boyd, In: *Cancer: Principles and Practice of Oncology Updates* (DeVita, V. T., Jr., et al., eds), Philadelphia: Lippincott, 1989, pp. 11-22; and Boyd, In: *Current Therapy in Oncology* (Niederhuber, J. E., ed.), Philadelphia: B C Decker, 1993, pp. 11-22. Although this NCI screen has been operational only since 1990, it has already led to the discovery, development, and clinical use of significant new anticancer drugs in human cancer patients. For example, see Weinstein et al., *Science*, 275, 343-349 (1997); Grever and Chabner, In: *Cancer: Principles and Practice of Oncology*, 5th Ed. (DeVita, V. T., et al., eds.), Philadelphia: Lippincott-Raven, 1977, pp. 385-394; and Sausville, In: *Anticancer Drug Development Guide: Preclinical Screening, Clinical Trials, and Approval* (Teicher, B. A., ed.), Totowa, N.J.: Humana Press, Inc., 1997, pp. 217-226.

The NCI screen consists of a panel of 60 different human tumor cell lines against which compounds are tested over a defined range of concentrations to determine the relative degree of growth inhibition or cytotoxicity against each cell line. The design and operation of the screen is such that for each compound tested, both the absolute and relative sensitivities of individual cell lines comprising the screen are sufficiently reproducible that a characteristic profile or "fingerprint" of cellular response is generated. Compounds that are active in the NCI screen show pronounced differential tumor growth-inhibitory and/or cytotoxic effects to the diverse cell lines comprising the 60 cell-line panel. The degree of differential response between the most and least sensitive lines typically may be relatively small (e.g., 2- to 10-fold), or occasionally as great as 3-4 orders of magnitude. Furthermore, the cell lines may be widely heterogeneous in response to a given compound, or they may be comparatively homogeneous, with only a relatively few lines showing much greater or lesser sensitivity than average. Regardless of the magnitude of the differential or the degree of heterogeneity of response of the cell line panel, it is the reproducibility of the response "fingerprint" that is important to the useful information contained therein.

Detailed disclosures of the screening assay are published, for example, in Monks et al., *J. Natl. Cancer Inst.*, 83, 757-766 (1991); Skehan et al., *J. Natl. Cancer Inst.*, 82, 1107-1112 (1990); and Boyd and Paull, *Drug Dev. Res.*, 34, 484-488 (1995). The identities, sources, derivation, morphological, and immunocytochemical characteristics, and methods of maintenance of the cell lines comprising the NCI 60 cell line panel have been described in detail, for example, in Boyd, In: *Cancer: Principles and Practice of Oncology Updates* (DeVita, V. T., Jr., et al., eds), Philadelphia: Lippincott, 1989, pp. 1-12; Monks et al., *J. Natl. Cancer Inst.*, 83, 757-766 (1991); Stinson et al., *Anticancer Res.*, 12, 1034-1035 (1992); and Boyd and Paull, *Drug. Dev. Res.*, 34, 91-109 (1995).

In the screening assay, each agent is tested over a broad concentration range against every cell line in the panel. All lines are inoculated onto a series of standard 96-well microtitre plates on day zero, followed by a 24 h incubation in the absence of the test compound. The inoculation densities employed depend upon the particular cell line and its growth characteristics. Inoculation densities used are as published in Monks et al., *J. Natl. Cancer Inst.*, 83, 757-766 (1991); and Boyd and Paull, *Drug Dev. Res.*, 34, 91-109 (1995). Test compounds are evaluated at five 10-fold dilutions. Following a 48-hour incubation with the test compound, the cells are assayed by the sulforhodamine B procedure as described in Skehan et al., *J. Natl. Cancer Inst.*, 82, 1107-1112 (1990); Monks et al., *J. Natl. Cancer Inst.*, 83, 757-766 (1991); and Rubinstein et al., *J. Natl. Cancer Inst.*, 82, 1113-1118 (1990). Optical densities are measured on automated plate readers, followed by computerized data acquisition, processing, storage, and availability for display and analysis.

Each successful test of a compound generates 60 dose-response curves, which are printed in the NCI screening data report as a series of composites comprising the tumor-type subpanels. Data for any individual cell line(s) failing quality control criteria, or otherwise deficient for any cell line(s) not tested successfully, are eliminated from further analysis and are deleted from the screening report.

The "percentage growth" (PG) term, and meaning of the +50, 0, and −50 response reference lines, the calculated response parameters, $GI_{50}$, TGI, and $LC_{50}$, construction and use of "mean-graphs" and the COMPARE pattern-recognition algorithms are briefly summarized as follows. The 50% growth inhibition parameter ($GI_{50}$) is the concentration of test drug where $100 \times (T-T_o)/(C-T_o) = 50 = PG$. The optical density of the test well after the 48 hour drug exposure is T; the optical density at time zero is $T_o$; and the control optical density is C. The PG is a T/C-like parameter that can have values from +100 to −100. Whereas the $GI_{50}$, may be viewed as a growth-inhibitory level of effect, the TGI signifies a "total growth inhibition" or cytostatic level of effect. The TGI is the drug concentration where $100\times(T-T_o)/(C-T)=0=PG$. The $LC_{50}$ is the lethal concentration, "net cell killing" or cytotoxicity parameter. It is the concentration where $100\times(T-T_o)/T_o=-50=PG$. The control optical density is not used in the calculation of $LC_{50}$. For a detailed description of the "percentage growth" (PG) term, the +50, 0, and −50 response reference lines, the calculated response parameters, $GI_{50}$, TGI, and $LC_{50}$, the construction and use of "mean-graphs," and the COMPARE pattern-recognition algorithms, see Boyd et al., In: *Cytotoxic Anticancer Drugs: Models and Concepts for Drug Discovery and Development* (Valeriote, F. A., et al., eds.), Amsterdam: Kluwer Academic Publishers, 1992, pp. 11-34; Monks et al., *J. Natl. Cancer Inst.*, 83, 757-766 (1991); and Boyd and Paull, *Drug Dev. Res.*, 34, 91-109 (1995).

A mean-graph is a pattern created by plotting positive and negative values, termed "deltas," generated from a set of $GI_{50}$, TGI, or $LC_{50}$ concentrations obtained for a given compound tested against each cell line in the NCI in vitro screen. The deltas are generated from the $GI_{50}$, TGI, or $LC_{50}$ data by a three-step calculation. For example, the $GI_{50}$ value for each cell line successfully tested against a given compound is converted to its $\log_{10} GI_{50}$ value. The mean panel $\log_{10} GI_{50}$ value is obtained by averaging the individual $\log_{10} GI_{50}$ values. Each $\log_{10} GI_{50}$ value then is subtracted from the panel mean to create the corresponding delta.

To construct the mean-graph, the deltas are plotted horizontally in reference to a vertical line that represents the calculated mean panel $GI_{50}$. The negative deltas are plotted to the right of the mean reference line, thereby proportionately representing cell lines more sensitive than the calculated average. Conversely, the positive deltas are plotted to the left of the reference line to represent the less sensitive cell lines to the given agent. Thus, for example, a bar projecting 3 units to the right of the vertical reference line in a $GI_{50}$ mean-graph indicates that the $GI_{50}$ concentration for that cell line is 1000 times less than the panel-averaged $GI_{50}$ concentration. The TGI and $LC_{50}$ mean-graphs are prepared and interpreted similarly.

Three additional numbers are printed at the base of each of the three respective mean-graphs. These numbers are the MG-MID, the Delta (not be confused with the "delta" for an individual cell line), and the Range. The MG-MID is the calculated mean panel $GI_{50}$, TGI, or $LC_{50}$. The Delta is the number of $\log_{10}$ units by which the delta of the most sensitive line(s) of the panel differ(s) from the corresponding MG-MID. Similarly, the Range is the number of $\log_{10}$ units by which the delta of the most sensitive line(s) of the panel differ(s) from the delta(s) of the least sensitive line(s).

COMPARE is a computerized, pattern-recognition algorithm used in the evaluation and exploitation of data generated by the NCI screen. In essence, COMPARE is a method of determining and expressing the degree of similarity, or lack thereof, of mean-graph profiles generated on the same or different compounds. An early impetus for the creation of such a tool during the development of the screen was the need to standardize and to establish and monitor the screen's consistency and reproducibility over time. This is accomplished by the regular testing of standard compounds that are expected to generate the same or very similar profiles when screened repetitively against the same panel of cell lines.

The NCI screen is repetitively calibrated. In the course of standardizing the screen, NCI selected as reference compounds approximately 170 agents for which a considerable amount of information was available about their preclinical and/or clinical anticancer properties and mechanism(s) of action. These compounds included commercially marketed anticancer drugs, investigational anticancer drugs, and other anticancer drugs which were or had been in preclinical development based upon activities in other cancer-related test systems. The repetitive periodic screening of these prototype "standard agents" (the cumulative compilation of results of which forms the "Standard Agents Database") remains the basis for calibration and standardization of the screen.

Significantly, the NCI's Standard Agent Database also provides a key to many useful new drug discovery applications. For example, the characteristic response profile "fingerprint" of a selected standard agent may be used as the "seed" to probe any other available mean-graph database to see if there are any closely matching profiles contained therein. Similarly, a profile selected from any available mean-graph database can be used to probe the "Standard Agent Database" to determine whether or not there are any closely matching standard agent profiles. Additional databases used for such studies may be constructed or defined as desired and may be relatively small (e.g., comprising a single compound or a selected congeneric series of compounds) or very large (e.g., the entire databases from all pure compounds, mixtures, fractions, and extracts tested in the NCI screen to date).

Initial NCI studies with COMPARE showed that compounds with matching mean-graph patterns often had related chemical structures. However, closer examination of this phenomenon revealed that certain compounds of unrelated structures had matching mean-graph patterns and shared the same or related biochemical mechanisms of action. For example, see Boyd, In: *Current Therapy in Oncology* (Niederhuber, J. E., ed.), Philadelphia: BC Decker, 1993, pp. 11-22; and Paull et al., In: *Cancer Therapeutic Agents*, Washington, D.C.: Am. Chem. Soc. Books, pp. 9-45 (1995); and references cited therein.

COMPARE analyses can be performed using the mean-graph deltas calculated from either the $GI_{50}$'s, the TGI's, or the $LC_{50}$'s. When a selected particular mean-graph profile or "seed" is used to probe a given database, the appropriate delta value for each cell line is compared to the corresponding delta value for the same cell line for every mean-graph entry in the specified database set. If either delta value is missing for any cell line (e.g., due to test failure or quality control deletion), then that cell line is eliminated entirely from the calculation for that particular seed/mean-graph and database/mean-graph pair. Thus, for each mean-graph in the specified database, a set of pairs (maximum of 60) of delta values is obtained. The commercially available SAS statistical program is used to calculate a Pearson product moment correlation coefficient (0.0-1.0) for each set of delta value pairs. The mean-graphs of all compounds in the specified database can then be rank-ordered for similarity to the seed mean-graph. Public access to the NCI's "Standard Agents Database," as well as to a variety of NCI screening data display and analysis tools, including COMPARE, are available to investigators worldwide via the Internet (http://dtp.nci.nih.gov/).

By regular application of COMPARE, using selected prototype seed compounds from the Standard Agents Database, NCI has maintained ongoing surveillance of the total historical screening database accrued from inception to date. In this manner, compounds with screening fingerprints matching standard agent(s) having known or presumed known mechanism(s) of actions can be identified. NCI has been able to associate and subsequently confirm the database classification of compounds of previously unknown mechanisms of action into a number of different known mechanistic classes of interest. For example, new members have been classified within general mechanistic categories of tubulin-interactive antimitotics, antimetabolites, alkylating agents, topoisomerase inhibitors, DNA binders, and the like. These and numerous other examples resulting from this kind of database prospecting have been published, for example, in Paull et al., *Cancer Res.*, 52, 3892-3900 (1992), and references cited therein; and Paull et al., In: *Cancer Chemotherapeutic Agents*, Washington, D.C.: Am. Chem. Soc. Books, 1995, pp. 9-45, and references cited therein.

As part of NCI's continuing drug screening efforts, the characteristic screening "fingerprints" for concanamycin A (FIGS. 12A-12C) and bafilomycin $A_1$ were determined in the NCI screen. There was a high correlation between the "fingerprints" for bafilomycin and concanamycin.

Quite surprisingly, it has been discovered that, uniquely among the tens of thousands of mean-graph "fingerprints" analyzed by applicant, the characteristic screening "fingerprints" for certain 12 and 15 membered ring compounds of the present invention correlate almost perfectly with concanamycin A (the most potent heretofore known vacuolar-type (H+)-ATPase inhibitor). The correlation for certain 12 and 15 membered ring compounds of the present invention is so precise, that the possibility of coincidence is effectively ruled out. It is therefore concluded that the compounds of the present invention, whose mean graph fingerprints in the NCI screen correlate with those of concanamycin A, are inhibitors of vacuolar-type (H+)-ATPase. Indeed, it has been further confirmed by specific vacuolar-type (H+)-ATPase bioassay that compounds of the present invention whose fingerprints in the NCI 60 cell-line screen correlate with those of concanamycin A have potent vacuolar-type (H+)-ATPase inhibitory activity, as expected. Thus, the NCI 60 cell-line screen can be used to demonstrate that any selected compound of the present invention is an inhibitor of vacuolar-type (H+)-ATPase.

Compounds whose mean-graph "fingerprints" generated by the NCI 60 cell-line screen correlate highly with one another can be expected to share a common molecular target or biological mechanism of action, even if the compounds differ significantly in structure. A high correlation can be established, for example, by COMPARE correlation coefficients of approximately 0.8 to 0.9, or greater. See Boyd, In: *Current Therapy in Oncology* (Niederhuber, J. E., ed) Philadelphia: B. C. Decker, 1993, pp. 11-22; Boyd and Paull, *Drug Dev. Res.*, 34, 91-109, 1995; Paull et al., In: *Cancer Therapeutic Agents*, Washington, D.C.: Am. Chem. Soc. Books, 1995, pp. 9-45. Thus, the concanamycins, bafilomycins, salicylihalamides and lobatamides, for example, whose NCI 60 cell-line screen correlation coefficients with respect to each other are high, can all be shown to share the same molecular target, vacuolar-type (H+)-ATPase. Further illustration of this characteristic is provided in Example 5.

One skilled in the art will appreciate that not all vacuolar-type (H+)-ATPase inhibitors will inhibit equally the vacuolar-type (H+)-ATPase activity present in different kinds or locations of intracellular organelles, or in different kinds or locations of plasma membranes, or in different kinds or locations of cells or tissues. In other words, a given vacuolar-type (H+)-inhibitory compound may preferentially inhibit vacuolar-type (H+)-ATPase activity in one or more kind or location of intracellular organelle, plasma membrane, cell or tissue. Thus, the skilled practitioner will typically select a particular vacuolar-type (H+)-ATPase inhibitory compound for a desired therapeutic use. Compound selection can be based upon the particular kind or location of intracellular organelle or plasma membrane vacuolar-type (H+)-ATPase preferentially inhibited by the compound. Indeed, there are clear precedents in the literature to indicate that compounds can be selected for particular applications based upon preferential inhibition of one or more kind of vacuolar-type (H+)-ATPase over another. For example, Gagliardi et al., *J. Med. Chem.*, 41, 1568-1573, (1998), identified compounds that selectively inhibit human osteoclast vacuolar-type (H+)-ATPase activity compared to human renal cortical vacuolar-type (H+)-ATPase activity; such compounds therefore are expected to be particularly useful in treating osteoporosis.

In addition to the pharmacological utility of inhibitors of mammalian vacuolar-type (H+)-ATPase activity, pharmacological utility may also be obtained by inhibition of non-mammalian vacuolar-type (H+)-ATPase activity. For example, the known vacuolar-type (H+)-ATPase inhibitors bafilomycin $A_1$ and concanamycin A potently inhibit fungal as well as mammalian vacuolar-type (H+)-ATPase activity, and those compounds have strong antifungal activity. See Bowman et al., *Proc. Natl. Acad. Sci. USA*, 85, 7972-7976 (1988); Dröse et al., *Biochemistry*, 32, 3902-3906 (1993); Dröse and Altendorf, *J. Exp. Biol.*, 200, 1-8 (1997). Remarkably, certain compounds of the present invention have been found to selectively inhibit mammalian (versus non-mammalian) vacuolar-type (H+)-ATPase, indicating that those compounds inhibit the enzyme by a mechanism that is distinct from those of any previously known inhibitor.

There is also evidence that vacuolar-type (H+)-ATPase plays important roles in the proliferation of tumor cells, and the consequent invasiveness and metastasis thereof. See Montcourrier et al., *J. Cell Sci.*, 107, 2381-2391 (1994); Martinez-Zaguilan et al., *Am. J. Physiol.*, 265, C1015-C1-29 (1993); Martinez-Zaguilan et al., *J. Cell Physiol.*, 176, 196-205 (1998); Nishihara et al., *Biochem. Biophys. Res. Commun.*, 212, 255-262 (1995); Manabe, et al., *J. Cell Physiol.*, 157, 445-452 (1993). Furthermore, acidification of intracellular organelles can contribute to the sequestration and cellular efflux of conventional anticancer drugs. See Marquardt and Center, *J. Natl. Cancer Inst.*, 83, 1098-1102 (1991); Benderra et al., *Intl. J. Oncol.*, 12, 711-715 (1998); Mariyama et al., *J. Biochem.*, 115, 213-218 (1994). Therefore, vacuolar-type (H+)-ATPase inhibitory compounds of the present invention can be used to inhibit the proliferation of tumor cells, as well as the consequent invasiveness and metastasis thereof. Furthermore, the compounds of the present invention can be used to inhibit drug-resistance of tumor cells to conventional anticancer agents.

The particular compound or composition used in accordance with the present invention may be selected based upon the desired kind or site of vacuolar-type (H+)-ATPase inhibition, and/or based upon other pharmacological, toxicological, pharmaceutical or other pertinent considerations that are well-known to those skilled in the art. Routine methods for the specific bioassay, quantitation and comparisons of inhibitory activity of compounds and compositions of the present invention against vacuolar-type (H+)-ATPase activity in various tissues, cells, organelles and other preparations is well-documented in the literature (see, e.g., Bowman et al., *Proc. Natl. Acad. Sci. USA*, 85, 7972-7976 (1988); Gagliardi et al., *J. Med. Chem.*, 41, 1883-1893 (1998); Gagliardi et al., *J. Med. Chem.*, 41, 1568-1573 (1998); and references cited therein).

The compounds of the present invention are structurally unique. Moreover, COMPARE analyses of $GI_{50}$ and TGI mean-graph screening profiles of certain compounds of the present invention consistently show a high degree of commonality with respect to each other (e.g., $GI_{50}$ and TGI-COMPARE Pearson correlation coefficients of at least 0.6-0.8 or greater), but do not show any such correlations with any known standard agent. Similarly, extracts of natural organisms which can be shown to contain compounds of the present invention typically give $GI_{50}$ and TGI mean-graph screening fingerprints with similarly high $GI_{50}$ and TGI-COMPARE Pearson correlations (e.g., typically 0.6-0.7 or greater) to the compounds of the present invention. This allows a person of skill in the art to readily identify productive source organisms and extracts thereof, from which the skilled artisan can readily obtain and use the compounds of the present invention or precursors thereof. Identification and/or characterization of the present inventive compounds is further facilitated by the presence of certain characteristic NMR signals. Such characteristic NMR signals can further confirm the identification and selection of compound mixtures, including crude extracts of natural organisms and partially purified fractions thereof, or synthetic or semi-synthetic reaction products, that contain the compounds. This is further illustrated as follows.

Figure 1:
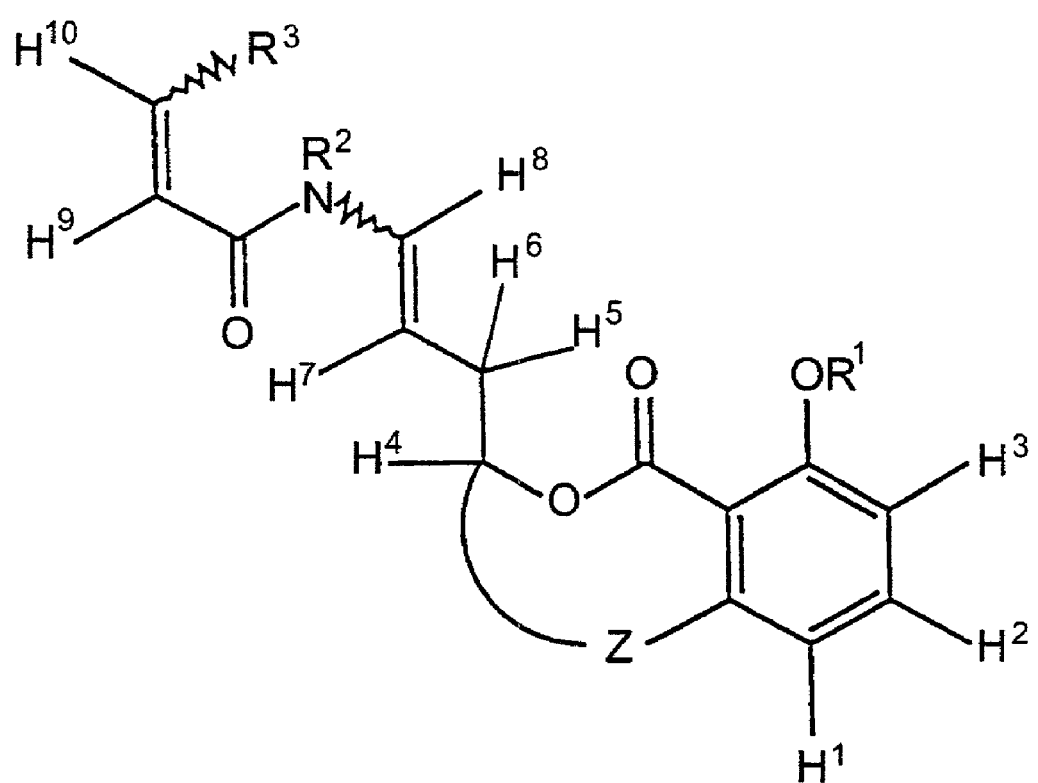
FIG. 1 is a general representation of certain compounds of the present invention in which $H^1$-$H^{10}$ denote hydrogen substituents that produce characteristic NMR signals.

FIG. 1 shows the structural locations of ten protons, depicted as hydrogen atoms ($H^1$-$H^{10}$), shared by preferred compounds of the present invention. Proton NMR spectroscopy (500 MHz) of compounds of the present invention shows that these ten protons produce resonances with chemical shift values that, taken together, are highly characteristic of the compounds of the present invention. These characteristic NMR peaks (which may vary in multiplicity depending upon the specific compound) are consistently centered within the following ranges of chemical shift values (when recorded in $CD_3OD$ and referenced to residual methanol) $H^1$, 6.60-6.70; $H^2$, 7.10-7.20; $H^3$ 6.65-6.75; $H^4$, 5.30-5.70; $H^{5,6}$, 2.30-2.60; $H^7$, 5.00-5.45; $H^8$, 6.70-6.90; $H^9$, 5.60-6.30; $H^{10}$, 6.40-7.20. For example, the particular $^1H$ NMR (500 MHz) chemical shifts and multiplicities of resonances for $H^1$-$H^{10}$ (in $CD_3OD$) for exemplary compounds of the present invention, salicylihalamides A and B, and lobatamides A and B, are illustrated below in Table 1.

TABLE 1

| H-Atom # | Salicylihalamide A ($^1H$ δ) | Salicylihalamide B ($^1H$ δ) | Lobatamide A ($^1H$ δ) | Lobatamide B ($^1H$ δ) |
|---|---|---|---|---|
| 1 | 6.65 d | 6.66 d | 6.63 d | 6.63 d |
| 2 | 7.12 t | 7.12 t | 7.14 dd | 7.14 dd |
| 3 | 6.72 d | 6.71 d | 6.68 d | 6.68 d |
| 4 | 5.36 m | 5.41 m | 5.58 m | 5.58 m |
| 5, 6 | 2.39 ddd, 2.42 ddd | 2.43 ddd, 2.53 ddd | 2.48 dd | 2.48 br. t |
| 7 | 5.36 m | 5.07 ddd | 5.34 dt | 5.34 m |
| 8 | 6.80 d | 6.73 d | 6.82 d | 6.82 d |
| 9 | 5.68 d | 5.84 d | 6.04 d | 6.05 d |
| 10 | 6.87 dt | 6.87 dt | 6.45 dd | 7.04 dd |

At least six of the characteristic resonances (specifically those representing $H_1$-$H_3$ and $H_9$-$H_{10}$) of the compound(s) of the present invention described in Table 1 are readily discernible in crude extracts of natural organisms that contain them. Thus, compounds of the present invention can be further identified from extracts of natural organisms when the extracts exhibit a characteristic mean-graph screening profile and exhibit a proton NMR spectrum with the aforementioned characteristic resonances for $H^1$-$H^3$ and $H^8$-$H^{10}$. Extracts having a characteristic mean-graph screening profile include those, for example, showing greater than or equal to 0.6-0.7 $GI_{50}$- and/or TGI-COMPARE correlation to the corresponding screening profile of a representative pure compound of the present invention. Once such an extract is selected, a practitioner of the art can obtain the compounds of the present invention according to the description provided herein. One such approach is illustrated in Example 1.

Certain 12-15 membered ring compounds of the present invention can be readily obtained from natural sources, including solvent extracts of marine sponges and tunicates, for example, from aqueous and organic solvent extracts of sponge species from the genus *Haliclona* and tunicate species from the genus *Aplidium*. Extracts of *Haliclona* sponges or *Aplidium* tunicates can be prepared from any suitable solvent, for example, organic solvents, water, and mixtures thereof. Fresh sponges or tunicates can be used, but more generally they are frozen immediately after harvesting, and then are either used directly or are freeze-dried before the extraction is done. When a marine sponge is used as a source for obtaining compounds of the present invention, it is preferably from the genus *Haliclona*, but is more preferably a *Haliclona* species, and is most preferably a *Haliclona* species collected near Rottnest Island, Western Australia (see Example 1).

When a tunicate is used as a source for obtaining compounds of the present invention, it is preferably from the genus *Aplidium*. More preferably the tunicate is an *Aplidium* species, which is sill more preferably *Aplidium lobatum*, and most preferably is *Aplidium lobatum* collected off the southwestern coast of Australia due west of Hillary Boat Harbor (see Example 1) Specific extracts of *Haliclona* and *Aplidium* species that contain compounds of the present invention can be identified and selected based upon the anticancer screening profile they produce in the NCI 60-cell human tumor screen. Such extracts containing compounds of the present invention also can be identified and selected based upon key proton NMR signals (Table 1) that are characteristic of the structural component motif (FIG. 2) shared by the compounds of the present invention (see also Example 1).

From the aforementioned selected extracts, a variety of methods can be used for isolation and purification of compounds of the present invention. During each step of isolation and purification, the aforementioned characteristic anti-cancer screening profile or a suitable bioassay, and the aforementioned characteristic proton NMR signals, can be obtained for intermediate fractions, as well as partially purified and purified compounds, to ensure isolation of the desired compounds of the present invention.

A preferred method of obtaining certain compounds of the present invention from natural source materials includes the steps of:

(a) obtaining a fresh or frozen sample of a marine sponge or tunicate (or other suitable natural source material) that includes one or more compounds of the present invention or a precursor thereof, (b) extracting the compound(s) or precursor(s) thereof from the sample with water or organic solvent(s) which dissolves the compound(s) or precursor(s) to form an aqueous or organic extract, (c) optionally treating the extract with ethanol to precipitate and remove high molecular weight proteins and sulfated polysaccharides, (d) partitioning the extract between a nonpolar organic solvent and an aqueous solvent to form a partitioned aqueous, nonpolar or polar organic extract containing the desired compound(s) or precursor(s) thereof, (e) chromatographing the partitioned extract, for example, on an adsorption, partition, or size-exclusion matrix, to form fractions, and (f) isolating compound(s) of the present invention or precursor(s) thereof from the fraction(s) containing it (them).

In step (b), the solvent can include a mixture of a suitable nonpolar organic solvent and a suitable polar organic solvent. Suitable nonpolar organic solvents include, for example, $CH_2Cl_2$, $CHCl_3$, toluene, and hexane. Suitable polar organic solvents include, for example, MeOH, EtOH, isopropyl alcohol, and acetone. In step (d) suitable organic nonpolar solvents include $CH_2Cl_2$, hexane, $CCl_4$, $CHCl_3$, MeOtBu, and ethyl acetate; and typical aqueous solvents are mixtures of water and methanol. Non-limiting examples of solvent mixtures that can be used in this partitioning step include: (1) $CH_2Cl_2$ vs. 19:1 $H_2O$-MeOH, (2) hexane vs. 9:1 MeOH—$H_2O$, (3) $CCl_4$ vs. 8:2 MeOH—$H_2O$, (4) $CH_2Cl_2$ vs. 7:3 MeOH—$H_2O$, and (5) EtOAc vs. $H_2O$. In step (d), the chromatography preferably is column chromatography. When column chromatography is used, the chromatographic matrix preferably is the adsorption type, the partition type, the size exclusion type, or a suitable combination thereof. Preferably, the solvent and the matrix are not too acidic in nature when the compound to be isolated is not particularly acid stable. Sephadex™ LH-20, a particularly preferred matrix for isolation of certain types of compounds of the present invention, combines all three of the aforesaid matrix types, and is characterized by mild treatment and good recoveries. The isolation step (f) can be carried out, for example, by either simply evaporating the solvent or by recrystallization.

Figure 3:
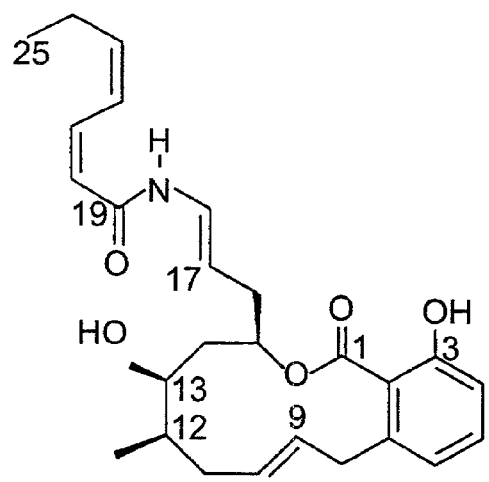
FIG. 3 illustrates the absolute stereochemistry of salicylihalamide A.

In one approach, a selected sample of frozen *Haliclona* species sponge is ground to a powder with dry ice. The dry ice is allowed to sublime, distilled $H_2O$ is added, and the thawed material is stirred for 3 h at 3° C., then centrifuged. The marc is lyophilized and extracted with a mixture of $CH_2Cl_2$—MeOH (1:1 v/v) at room temperature (e.g., 20-25° C.) overnight. The solvent is drained, and the marc is rinsed with MeOH. The combined organic extracts are evaporated to dryness. The crude organic extract is subjected to vacuum-liquid chromatography in several batches on Diol-60 columns, eluting successively with hexane, $CH_2Cl_2$—MeOH EtOAc, acetone, and MeOH. The EtOAc fraction is passed through a column of Sephadex™ LH-20 with $CHCl_2$—MeOH (1:1) to give a fraction with the characteristic bioactivity profile and NMR signals of the compound(s) of the present invention. A second Sephadex™ LH-20 column is eluted with hexane-toluene-MeOH (3:2:2) to afford substantially purified compound(s) of the present invention. Salicylihalamide A (FIG. 3A) and its $\Delta^{17}$-cis-isomer (salicylihalamide B) (FIG. 3C) are isolated by C-18 reverse-phase HPLC (using a linear gradient from 70% to 100% MeOH) in pure form. More specific illustrations of isolation of representative compounds of the present invention are given in Example 1.

The definitive proofs of structure of the isolated compounds can be obtained by a combination of methods including primary spectral analyses (e.g., high-resolution NMR and mass spectrometry, infrared and UV spectroscopy), comparisons of spectral and physico-chemical properties with related literature precedents, and by x-ray crystallographic analysis. These are further illustrated in Example 2 herein.

EXAMPLES

The following examples further illustrate the present invention but, of course, should not be construed as in any way limiting its scope.

Example 1

This example illustrates a procedure for obtaining certain compounds of the present invention from marine sponges and tunicates.

The particular extract of a *Haliclona* sp. sponge selected from the NCI Natural Products Repository, Frederick, Md., for investigation in the present example showed an NCI 60-cell screening mean-graph (TGI) fingerprint that was highly correlated (TGI-COMPARE Pearson correlation coefficient greater than or equal to 0.7) to that of either salicylihalamide A or lobatamide A. The extract also showed proton NMR (500 MHz) resonances at chemical shift values (and multiplicities) recorded in $CD_3OD$ and referenced to residual methanol of: 6.65 (d), 7.12 (t), 6.72 (d), 6.80 (d), 5.68 (d), and 6.87 (dt). The selected extract was from a *Haliclona* sp. sponge that had been collected by P. Murphy in Southwestern Australia, 0.7 nautical miles off Rottnest Island, in March, 1989, at a depth of 15 meters. The sponge reportedly occurred as a green mass with amorphous lobes, growing on the underside of a rocky overhang, and was identified by P. Jane Fromont of James Cook University. A voucher specimen of this particular sponge collection (coded as serial number Q66C2670) is on deposit at the Smithsonian Institution Taxonomy and Sorting Center, Suitland, Md.

Salicylihalamides A and B were isolated as follows. Approximately 450 g frozen wet wt. of the sponge was ground to a powder with dry ice. The dry ice was allowed to sublime, distilled $H_2O$ was added, and the thawed material was stirred for 3 h at 3° C., then centrifuged. The marc was freeze-dried and extracted with a mixture of $CH_2Cl_2$-MeOH (1:1 v/v) at room temperature overnight. The solvent was removed by filtration, and the marc was rinsed with MeOH. The combined solutions were evaporated to yield approximately 3.5 g of crude extract.

Initial attempts to isolate the active constituents revealed that the bioactivity was lost from crude extracts and chromatographic fractions thereof in the presence of deuterated chloroform. For example, overnight storage of $CDCl_3$ solutions of partially purified fractions resulted in the formation of a tarry, insoluble residue that was inactive in the anticancer screen. Therefore, all subsequent attempts at isolation avoided the use of chloroform or exposure of samples to $CDCl_3$, and no further problems with decomposition or loss of bioactivity were encountered. Moreover, there was no indication of any instability of the pure isolated compounds in any of the other common organic solvents employed, nor in aqueous or biological media.

A typical isolation and purification of the salicylihalamides from the selected crude extract is as follows. An aliquot of extract (330 mg) was coated on 2.1 g of diol bonded phase and sequentially batch-eluted with 100 ml portions of hexane, $CH_2Cl_2$, EtOAc, acetone, and MeOH. The cytotoxic $CH_2Cl_2$ and EtOAc eluates were combined (107 mg) and permeated through Sephadex™ LH-20 with hexane-toluene-MeOH (3:2:2 v/v, 1.5×45 cm column) to yield four fractions, the second of which (8.4 mg) showed NMR signals corresponding to salicylihalamide A. HPLC on wide-pore C-18 (Rainin™ 1×25 cm) using a linear gradient from 70% to 100% MeOH over 20 min yielded 5.5 mg of pure salicylihalamide A (retention time 13 min) and a smaller amount (approximately 0.5 mg) of salicylihalamide B (retention time 14.5 min).

Physicochemical and spectroanalytical data for salicylihalamide A were as follows: amorphous solid; $[\alpha]_D$ −35° (c=0.7, MeOH); $\lambda_{max}$ (MeOH) 280 nm ($\epsilon$=34,000) $\nu_{max}$ (film) 3288, 2964, 1697, 1651, 1606, 1588, 1520, 1464, 1293, 1268, 1247, 1214, 1123, 1068, 972, 869, 735 cm$^{-1}$; for $^1$H and $^{13}$C NMR, see Example 2, Table 2 (below); EIMS m/z 439 [M$^+$] (43), 421 (1), 410 (5), 409 (2), 392 (2), 330 (7), 315 (8), 313 (3), 312 (3), 296 (10), 288 (12), 278 (4), 231 (12), 191 (40), 149 (17), 125 (18), 124 (6), 109 (100), 108 (19), 107 (16), 96 (63), 91 (10), 83 (31), 82 (50), 81 (87), 79 (35), 56 (27), 55 (24), 43 (14), 18 (19); HREIMS m/z 439.2354 (M$^+$, calcd for $C_{26}H_{33}NO_5$, 439.2350).

Physicochemical and spectroanalytical data for salicylihalamide B were as follows: amorphous solid; $[\alpha]_D$ −73° (c=0.3, MeOH); $\lambda_{max}$ (MeOH) 280 nm ($\epsilon$=38,000); $\nu_{max}$ (film) 3356, 2964, 2923, 1690, 1651, 1588, 1503, 1463, 1294, 1246, 1212, 1121, 1032, 972 cm$^{-1}$; $^1$H NMR ($C_6D_6$) δ 0.77 (3H, t, 7.3), 0.83 (3H, d, 6.8), 1.22 (dd, 15.2, 8.8), 1.32 (br s), 1.50 (br q, 6.8), 1.73 (br m), 1.74 (dd, 15.2, 10.5), 1.89 (ddd, 15.2, 7.8, 7.4), 1.95 (2H, quintet, 7.3), 2.05 (ddd, 14.7, 6.8, 6.4), 2.08 (br m), 3.25 (br d, 16.5), 3.27 (br d, 8.8), 3.56 (dd, 16.5, 4.9), 4.52 (dt, 10.2, 8.8, 8.8), 5.08 (ddd, 15.6, 7.3, 6.4), 5.17 (very br m), 5.20 (very br m), 5.48 (d, 11.2), 5.62 (dt, 10.7, 7.8, 7.3), 6.45 (dd, 8.3, 3.9), 6.62 (dd, 11.2, 10.8), 6.95 (m), 7.29 (t, 10.3), 7.66 (br d, 10.2), 7.93 (t, 10.8), 11.58 (br s); $^{13}$C NMR ($C_6D_6$) δ13.8, 14.0, 20.8, 31.5, 36.2, 38.0, 38.4, 39.4, 70.9, 76.1, 103.3, 117.2, 119.5, 123.7, 124.9, 125.4, 126.8, 132.8, 134.6, 137.4, 141.9, 163.0, 172.0 (3 of the quaternary carbons were not observed); HREIMS m/z 439.2351 (M$^+$, calcd for $C_{26}H_{33}NO_5$, 439.2350).

The extract of *Aplidium lobatum* selected from the NCI Natural Products Repository, Frederick, Md., for investigation in the present example showed an NCI 60-cell screening mean-graph (TGI) fingerprint that was highly correlated (TGI-COMPARE Pearson correlation coefficient greater than or equal to 0.7) to that of either salicylihalamide A or lobatamide A. The extract also showed proton NMR (500 MHZ) resonances at chemical shift values (and multiplicities) recorded in $CD_3OD$ and referenced to residual methanol of: 6.63 (d), 7.14 (t), 6.68 (d), 6.82 (d), 6.04 (d), and 6.45 (dd). The selected extract was from an *Aplidium lobatum* collected by P. Murphy off the southwestern coast of Australia due west of Hillary Boat Harbor at a depth of 6 meters. The taxonomy was provided by Patricia Kott of the Queensland Museum. Voucher specimens of this particular tunicate collection (coded as serial number Q66C2780) are on deposit both at the Australian Institute of Marine Science and the Smithsonian Institute. Lobatamides A and B were isolated as follows.

The *A. lobatum* (642 g wet weight) was frozen immediately after collection until extraction. The aqueous extract (13.8 g) was first taken through an EtOH precipitation procedure to remove high molecular weight proteins and sulfated polysaccharides as follows. The extract was divided into 5 g aliquots, each of which was dissolved in H—O (40 ml) followed by addition of EtOH (40 ml). The solutions were allowed to sit overnight at −20° C., after which the precipitates were pelleted by centrifugation, and the supernatants were decanted and combined. The combined precipitate was washed with $H_2O$-EtOH (1:1, 40 ml) and pelleted again with centrifugation. The wash was decanted and added to the combined supernatant. The EtOH was removed from the combined supernatant by rotary evaporation, and the remaining $H_2O$ was removed by lyophilization. The lyophilized supernatant was partitioned between EtOAc and $H_2O$ to yield cytotoxic EtOAc soluble materials enriched in the compounds of interest, as determined both by the aforementioned characteristic NCI 60 cell-line screening profile and proton NMR chemical shifts. This EtOAc-soluble material was sequentially chromatographed using gel permeation (Sephadex™ LH-20, 1:1 MeOH-MeCN), followed by VLC (amino-bonded phase, $CH_2Cl_2$—MeOH gradient 100-90% $CH_2Cl_2$), Sanki CPC (5:7:4 CHCl—MeOH—$H_2O$, ascending mode, 1.7 ml/min), and finally HPLC ($C_{18}$, 3:7 MeCN—$H_2O$) to yield lobatamide A (1.1 mg, 8.0×10$^{-3}$ wet wt) and lobatamide B (1.4 mg, 0.01% wet wt).

Physicochemical and spectroanalytical data obtained for lobatamide A were as follows: $[\alpha]_D$ −7.9° (c 0.24, MeOH); UV (MeOH) $\lambda_{max}$ 273 nm (log $\epsilon$ 4.22); IR (film) $\nu_{max}$ 3590-3128 (br), 2974, 2933, 1739, 1656, 1523, 1461, 1451, 1374, 1266, 1215, 1169, 1113, 1042 cm$^{-1}$; HRFABMS (noba) MH$^+$ m/z 513.2257 for $C_{27}H_{33}N_2O_8$ Δ+2.0 mmu; FABMS (magic bullet) m/z 535 (M+Na$^+$, 8%) 513 (MH$^-$, 16), 495 (15), 460 (20), 289 (65), 239 (22), 176 (30), 154 (100), 138 (100), 105 (83).

FAB mass spectra were obtained on a JEOL™ SX102 spectrometer using a 10 kV xenon gun to desorb the samples from a magic bullet matrix (5:1 DTT-DTE). Spectra were run in both positive and negative ionization conditions. Fragmentation analyses were performed by B/E linked scans of the parent and fragmentation ions. Where necessary, a helium collision gas was used in the first field free region to enhance this fragmentation. Exchange spectra were performed under chemical ionization (CI) conditions on a Finnigan 4500 spectrometer using the direct exposure probe. Exchanges were determined by comparing spectra obtained using $ND_3$ as the reagent gas with those from $NH_3$. HRFABMS data for structurally significant fragments were as follows: II: 495.2115 for $C_{27}H_{31}N_2O_7$, calcd 495.2131; 3 exchangeable protons; III: 239.1021 for $C_{11}H_{15}N_2O_4$, calcd 239.1032; 2 exchangeable protons; V: 112.0402 for $C_5H_6NO_2$, calcd 112.0399; VI: seen in CI only; 3 exchangeable protons; VII: 257.1129 for $C_{16}H_{17}O_3$, calcd 257.1137; 2 exchangeable protons; VIII: 291.1231 for $C_{16}H_{19}O_5$, calcd 291.1231; IX: 273.1118 for $C_{16}H_{17}O_4$, calcd 273.1127; X: 219.0650 for $C_{12}H_{11}O_4$, calcd 219.0657.

Physicochemical and spectroanalytical data obtained for lobatamide B were as follows: $[\alpha]_D$ −15° (c 0.03, MeOH); UV (MeOH) $\lambda_{max}$ 288 nm (log $\epsilon$ 4.55); IR (film) $\nu_{max}$ 3580-3118 (br), 3056, 2974, 2933, 1733, 1651, 1605, 1584, 1528, 1467, 1451, 1267, 1221, 1175, 1113, 1046 cm$^{-1}$; HRFABMS (magic bullet) MH$^+$ m/z 513.2244 for $C_{27}H_{33}N_2O_8$ Δ+0.7 mmu; FABMS (glyc) m/z 513 (MH$^-$, 10%), 495 (10), 461 (8), 279 (55), 239 (23), 177 (25), 153 (100), 135 (100).

Example 2

This example illustrates the structure proofs of particular compounds of the present invention.

Salicylihalamide A, such as obtained and characterized spectroanalytically in Example 1, was an amorphous solid with a molecular formula established by HREIMS as $C_{26}H_{33}NO_5$. The $^{13}$C and DEPT NMR spectra (Table 2) showed 26 unique resonances: 5 quaternary, 14 methine, 5 methylene, and 2 methyl carbons. Chemical shift values further characterized two ester or amide carbonyls, 14 olefinic or aromatic carbons, and two oxygenated methines. Three exchangeable protons completed the proton count. The IR spectrum confirmed OH and/or NH (3288 cm$^{-1}$)

functionalities and suggested the presence of both an amide (1651 cm$^{-1}$) and an intramolecularly hydrogen-bonded conjugated ester (1697 cm$^{-1}$). The $^{13}$C (125 MHz) and $^{1}$H (500 MHz) NMR data for salicylihalamide A in C$_6$D$_6$ and CD$_3$OD are illustrated below in Table 2.

4B) and the amide carbonyl (δ 162.9 in C$_6$D$_6$ and 165.9 in CD$_3$OD) of substructure C (FIG. 4C) established the connection of B to C through this amide carbonyl carbon. This was confirmed by an HMBC correlation between the amide proton and carbonyl in C$_6$D$_6$ and by the base peak in the

TABLE 2

| C# | δ$_c$ (C$_6$D$_6$) | δ$_H$ (multiplicity, Hz) (C$_6$D$_6$)[a] | HMBC ($^1$H Correlation, C$_6$D$_6$) | δ$_c$ (CD$_3$OD) | δ$_H$ (multiplicity, Hz) (CD$_3$OD)[a] | HMBC ($^1$H correlation, CD$_3$OD) |
|---|---|---|---|---|---|---|
| 1 | 171.2 | — | 15 | 171.0 | — | 15 |
| 2 | 114.7[b] | — | 4, 6, 8a, 8b | 123.0 | — | 6 |
| 3 | 163.0 | — | 4 and/or 5 | 157.1 | — | 5 |
| 4 | 117.1 | 6.97(m) | 5, 6 | 115.3 | 6.72(d, 7.3) | 6 |
| 5 | 134.0 | 6.97(m) | 6 | 131.6 | 7.12(t, 7.3) | — |
| 6 | 123.6 | 6.48(dd, 6.4, 2.0) | 4 and/or 5, 8a, 8b | 122.5 | 6.65(d, 7.3) | 4, 8b |
| 7 | 142.6 | — | 5, 6, 8a, 8b, 9 | 140.7 | — | 5, 8b |
| 8 | 39.3 | 3.32(br d, 16.6) 3.61(br dd, 16.6, 4.9) | 9 | 38.8 | 3.34(br dd, 16.6, 7.8) 3.56(dd, 16.6, 8.3) | 6, 9, 10 |
| 9 | 132.7 | 5.28(dt, 15.1, 4.9, 4.4) | 8a, 8b, 11a, 11b | 130.7 | 5.29(dddd, 15.2, 8.3, 7.8, 1.5) | 8b, 11b |
| 10 | 127.0 | 5.05(br m) | 8a, 8b, 11a, 11b | 131.7 | 5.36(m) | 8b, 11a |
| 11 | 38.5 | 1.65(dd, 13.7, 8.8) 2.12(m) | 9, 13, 26 | 38.9 | 1.75(m) 2.28(m) | 9, 10 |
| 12 | 37.6 | 1.51(br dq, 6.8, 3.5) | 11a, 13, 14b, 26 | 38.6 | 1.87(br m) | — |
| 13 | 70.5 | 3.46(dd, 8.8, 3.5) | 14a, 15, 26 | 72.0 | 4.12(dd, 9.3, 3.4) | 14a, 15 |
| 14 | 35.4 | 1.28(dd, 15.0, 8.8) 1.66(dd, 15.0, 10.3) | 13, 15, 16a, 16b | 36.6 | 1.37(dd, 15.3, 9.3) 1.75(m) | 13, 15, 16 |
| 15 | 75.3 | 5.55(dt, 10.3, 6.5) | 13, 14b, 16a, 16b, 17 | 76.0 | 5.36(m) | 13, 14b, 16 |
| 16 | 36.3 | 2.07(ddd, 14.6, 7.3, 6.5) 2.20(ddd, 14.6, 7.3, 6.5) | 14b, 15, 17 | 37.6 | 2.39(ddd, 14.2, 6.8, 6.3) 2.42(ddd, 14.2, 6.8, 6.3) | 15, 17 |
| 17 | 107.0 | 4.84(dt, 14.5, 7.3) | 15, 16a, 16b | 110.4 | 5.36(m) | 15, 16 |
| 18 | 126.0 | 7.13(dd, 14.5, 10.8) | 16a, 16b, 17 | 126.2 | 6.80(d, 14.7) | 16 |
| 19 | 162.9 | — | 20, 21, NH | 165.9 | — | 20, 21 |
| 20 | 119.6 | 5.17(d, 11.2) | | 120.3 | 5.68(d, 11.7) | — |
| 21 | 136.9 | 6.62(dt, 11.2, 1.0) | 20, 23 | 137.7 | 6.87(dt, 11.7, 1.0) | 23 |
| 22 | 124.9 | 7.92(dt, 10.8, 1.5) | 20, 24 | 125.3 | 7.30(dt, 10.7, 1.5) | 20, 24 |
| 23 | 141.7 | 5.63(ddddd, 10.8, 7.3, 7.3, 1.0, 1.0) | 21, 24, 25 | 142.6 | 5.82(ddddd, 10.7, 7.4, 7.4, 1.4, 1.0) | 21, 24, 25 |
| 24 | 20.8 | 1.97(d quintets, 7.3, 7.3, 7.3, 1.5) | 23, 25 | 21.5 | 2.28(d quintets, 7.4, 7.4, 7.4, 7.4, 1.5) | 22, 23, 25 |
| 25 | 14.0 | 0.77(t, 7.3) | 23, 24 | 14.4 | 1.02(t, 7.4) | 23, 24 |
| 26 | 13.9 | 0.82(d, 6.8) | 11a, 13 | 13.6 | 0.85(d, 6.8) | 11b, 13 |
| NH | — | 6.76(d, 10.8) | — | — | — | — |
| OH (C-3) | — | 11.46(br s) | — | — | — | — |

[a]With geminal protons, the smaller δ-value is given the "a" designation, the larger δ-value is given the "b" designation.
[b]Weak and broad.

Because of the sensitivity of salicylihalamide A to CDCl$_3$, all NMR spectroscopy experiments were carried out in C$_6$D$_6$ or CD$_3$OD. Signals obscured by or unresolved in the first solvent were readily discernible in the second. Consequently, $^1$H-$^1$H COSY, HMQC, and HMBC NMR data were gathered in both solvents. The $^1$H-$^1$H COSY spectrum of salicylihalamide A in C$_6$D$_6$ revealed the following correlations (H/H): 4/6, 5/6, 8a/8b, 8a/9, 8a/10, 8a/11b, 8b/9, 9/10, 10/11a, 10/11b, 11a/11b, 11a/12, 11b/12, 12/13, 12/26, 13/14a, 13/14b, 14a/14b, 14a/15, 14b/15, 15/16a, 15/16b, 16a/16b, 16a/17, 16a/18, 16b/17, 16b/18, 17/18, 18/NH, 20/21, 20/22, 20/23, 21/22, 21/23, 22/23, 22/24, 23/24, 24/25. From a combination of the HMQC (Table 2) and the COSY spectral data, the partial structures illustrated in FIGS. 5A-5C were generated.

Figure 4A:
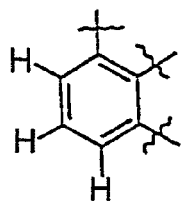
FIG. 4A illustrates a component partial structure used in the structure analysis of salicylihalamide A.
Figure 4B:
FIG. 4B illustrates a component partial structure used in the structure analysis of salicylihalamide A.
Figure 4C:
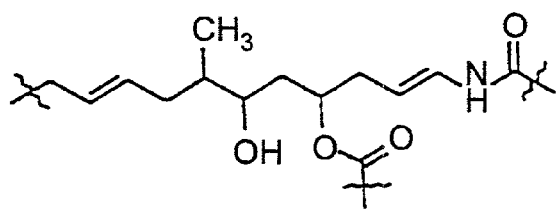
FIG. 4C illustrates a component partial structure used in the structure analysis of salicylihalamide A.

The enamide functionality in segment C (FIG. 4C) was identified through a 10.8 Hz coupling between the adjacent olefinic and amide N—H protons; the latter was characterized by its variable chemical shift values. All 26 carbons were accounted for in partial structures A, B, and C, corresponding to FIGS. 4A, 4B, and 4C, respectively. In the HMBC spectra (Table 2), coupling between the two vinyl hydrogens [δ 5.17 (H-20) and 6.62 (H-21) in C$_6$D$_6$; δ 5.68 and 6.87 in CD$_3$OD] of the hexadiene substructure B (FIG.

mass spectrum (m/z 109, C$_7$H$_9$O). The IR spectral evidence that the ester carbonyl was both conjugated and intramolecularly hydrogen-bonded (1697 cm$^{-1}$) was supported by the low-field chemical shift of the phenolic OH (δ 11.46, C6D$_6$). This indicated that the ester carbonyl was ortho to the phenolic OH in substructure A (FIG. 4A). The remaining open aromatic position then had to be occupied by the allylic carbon of moiety C (FIG. 4C), giving the structure for salicylihalamide A.

Confirmation of the aromatic substitution pattern came from HMBC correlations, which were optimized for 8.3 Hz couplings. In CD$_3$OD, the phenolic carbon and the amide carbonyl carbon were resolved, as were all three aromatic protons and all six aromatic carbons. Moreover, the latter were not obscured by solvent resonances. In CD$_3$OD, the aromatic proton at δ 7.12 (H-5) showed a correlation to both the oxygen-bearing phenolic carbon at δ157.1 (C-3) and the quaternary aromatic carbon at 140.7 (C-7). As this δ 7.12 proton was a triplet (J=7.3 Hz) in the $^1$H NMR spectrum, the two quaternary aromatic carbons to which it was correlated were meta to it. The δ 6.65 (H-6) aromatic hydrogen showed correlation to two different aromatic carbons, the methine at δ 115.3 (C-4) and the quaternary carbon at δ 123.0 (C-2). Furthermore, the δ 6.65 proton was correlated to the side-chain aliphatic carbon at δ 38.8 (C-8), necessitating the placement of this side-chain ortho to the δ 6.65 hydrogen. To accommodate an ortho substituent and account for its chemical shift, this δ 6.65 hydrogen had to be para to the phenolic OH. Confirming this assignment were the correlations observed between the benzylic proton (H-8, δ 3.56) of the side-chain and both the quaternary aromatic carbon at δ 140.7 (C-7) and the δ 122.5 (C-6) aromatic carbon bearing the δ 6.65 hydrogen. The only remaining aromatic site for the ester carbonyl attachment was that ortho to the phenolic OH (at δ 123.0), as shown in the structure for salicylihalamide A. Additional HMBC correlations are shown in Table 2.

Figure 5:
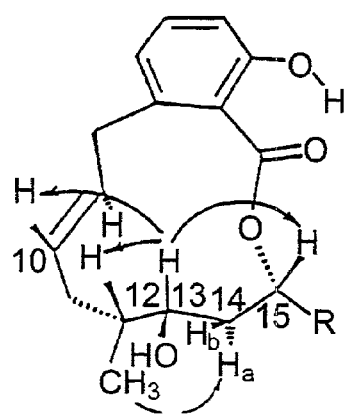
FIG. 5 illustrates various nOe relationships in salicylihalamide A.
Figure 6:
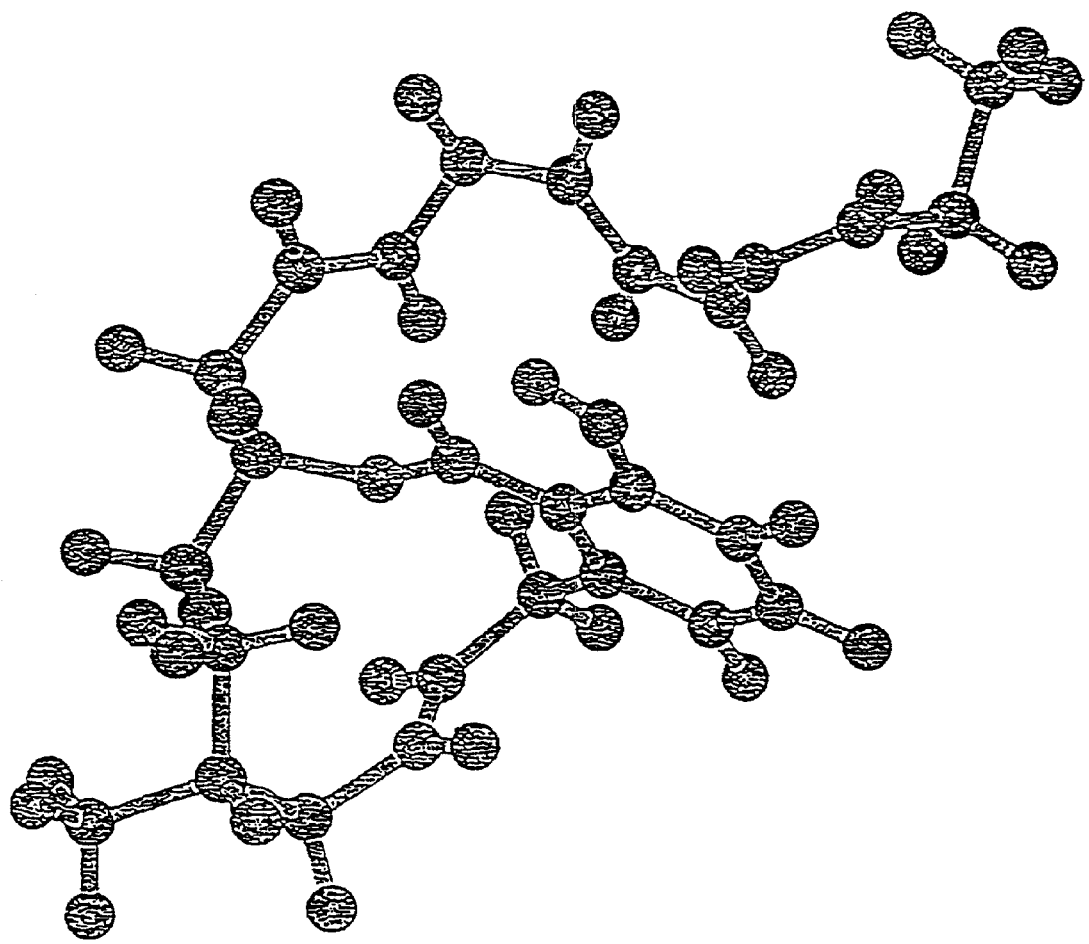
FIG. 6 shows a computer-generated model of the conformation of salicylihalamide A.

The relative stereochemistry of salicylihalamide A was deduced from a combination of $^1H$-$^1H$ coupling constants and difference nOe spectra. FIG. 5 illustrates important nOe interactions; most notable were the interactions of the alcohol methine (H-13) with the ester methine (H-15), the methyl-bearing methine (H-12), and the olefinic hydrogen (H-10). All four of these protons must reside on the same face of the molecule, leading to the relative stereochemistry depicted in FIG. 3. The dihedral angle between the ester methine (H-15) and H-14a must be approximately 90°, since no coupling was observed between these two vicinal hydrogens. The dihedral angle between H-15 and H-14b must approach 180° to accommodate both their coupling constant (10.3 Hz) and the lack of a measurable nOe between them. Likewise, H-14b and the alcohol methine (H-13) showed no measurable coupling, indicating a dihedral angle of approximately 90°, while a large dihedral angle between H-14a and H-13 was needed to accommodate a sizeable coupling (8.8 Hz). H-13, in turn, displayed a J-value of 3.5 Hz and a substantial nOe with H-12, suggesting a dihedral angle of approximately 60° between these two protons. Molecular modeling studies, generating minimum energy structures with the nOe constraints described above, gave rise to predicted J-values that agreed within 1-1.5 Hz of the actual experimental values. FIG. 6 depicts one such computer-generated model of salicylihalamide A. Thermodynamic modeling calculations were performed using Macromodel v3.0 [Mohamadi et al., J. Computat. Chem., 11, 440-467 (1990)] implemented on a VAX 6620 computer. An input model with a flat macrolide structure with relative stereochemistry constructed by Dreiding models was drawn by hand. Distance constraints were applied sequentially, and energy minimization was performed at each step. After constraints corresponding to the prominent observed transannular nOe's had been applied, the constraints were removed, and the structure was minimized without constraint to produce the final model. The graphic (FIG. 6) was produced by downloading the structure and printing from the Chem3D program.

The question of absolute stereochemistry was addressed through the use of Mosher esters. See Ohtani et al., J. Org. Chem., 56, 1296-1297 (1991); Dale et al., J. Am. Chem. Soc., 95, 512-519 (1973); Oh et al., J. Org. Chem., 54, 4499-4503 (1989); Leclercq et al., Tetrahedron Lett., 50, 8465-8488 (1994); and Kaneko et al., Tetrahedron Lett., 35, 4107-4110 (1994). Both the (R)- and (S)-methoxy trifluoromethylphenyl acetate (MTPA) diesters of salicylihalamide A were prepared and subjected to $^1H$ NMR analysis (Table 3). A small amount of the tris-MTPA derivative (diester imide) was formed in each case and was removed by preparative TLC prior to NMR analyses. The Mosher ester analysis of salicylihalamide A in $C_6D_6$ is illustrated below in Table 3.

TABLE 3

| | H-10 | H-26 | H-14a | H-15 | H-17 |
|---|---|---|---|---|---|
| R-MTPA diester | 4.92 | 0.52 | 1.58 | 5.55 | 4.64 |
| S-MTPA diester | 5.58 | 0.63 | 1.52 | 5.04 | 4.44 |
| Δ ($δ_S - δ_R$) | +0.66 | +0.11 | −0.06 | −0.51 | −0.20 |

The preparation of the MTPA esters was performed as follows. To a mixture of 0.5 mg of salicylihalamide in 10 μl of anhydrous $CH_2Cl_2$ and 15 μl of anhydrous pyridine in a septum-sealed vial were added 1.2 μl of the enantiomercially pure α-methoxy-α-trifluoromethyl phenylacetyl chloride. The reaction mixture was allowed to stand at 25° C. for 16 h $H_2O$ and $CH_2Cl_2$ were added, and the $CH_2Cl_2$ layer was washed several times with $H_2O$, then passed through a short column of anhydrous $Na_2S_4$ and evaporated to dryness under $N_2$. The residue was subjected to reverse-phase TLC ($C_{18}$) with MeOH to give di- and tri-MTPA derivatives. Mass spectral data were as follows: (diesters) HRFABMS m/z 872.324 [(R)-derivative]; 872.323 [(S)-derivative] (MH$^+$, calcd for $C_{46}H_{48}F_6NO_9$, 872.322); (diester imides) HRFABMS m/z 1088.361 [(R)-derivative]; 1088.362 [(S)-derivative] (MH$^+$, calcd for $C_{56}H_{55}F_9NO_{11}$, 1088.362).

Figure 7A:
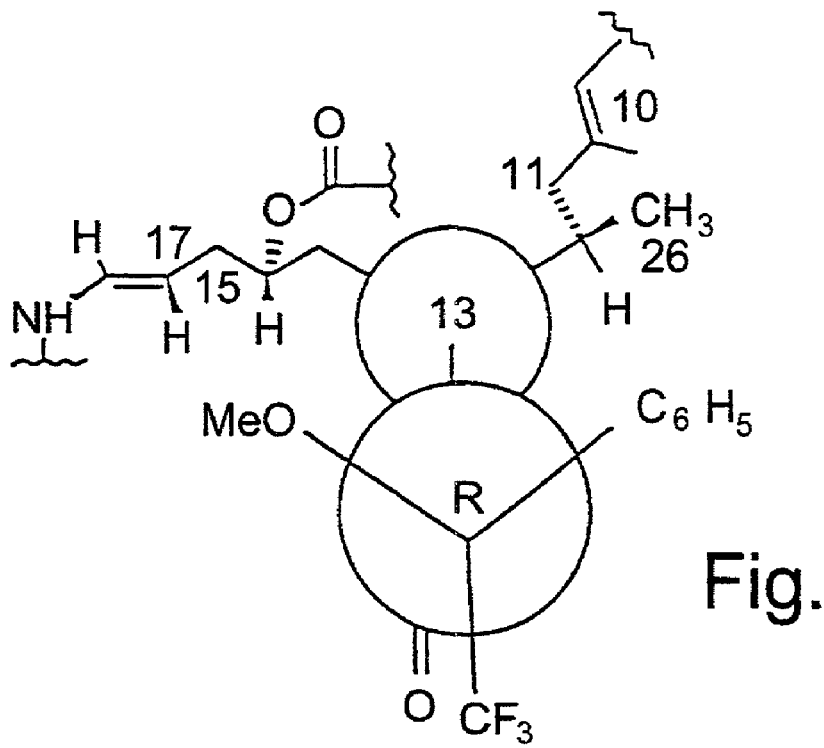
FIG. 7A illustrates a Newman projection depicting the partial structure of the (R)-Mosher derivative of salicylihalamide A.
Figure 7B:
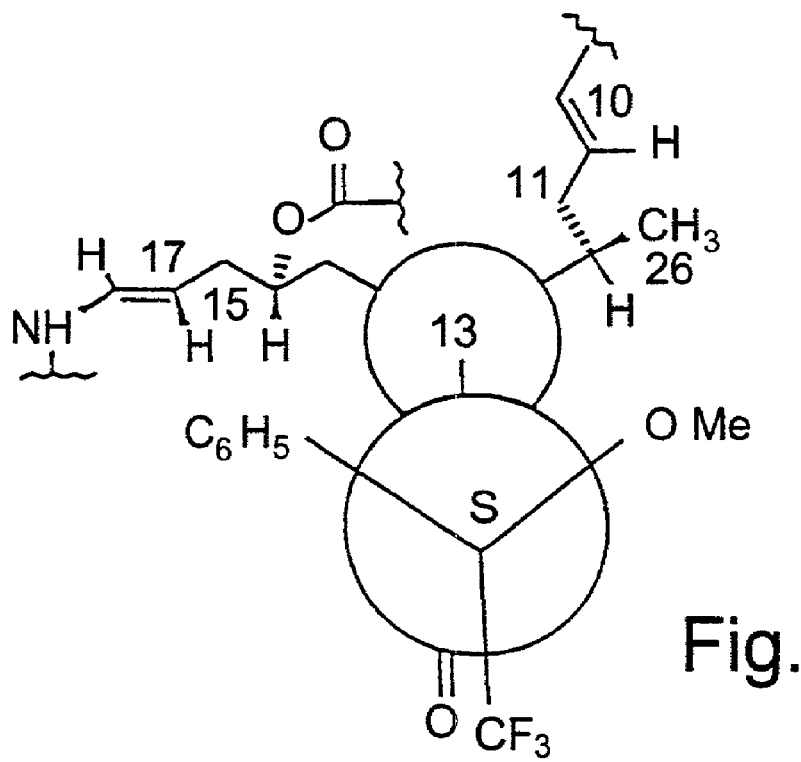
FIG. 7B illustrates a Newman projection depicting the partial structure of the (S)-Mosher derivative of salicylihalamide A.

Analysis of the Mosher ester NMR data was as follows. The C-12 methyl hydrogens (H-26) and H-10 of the (R)-derivative appeared upfield of those of the (S)-derivative in $C_6D_6$. Likewise, H-14a, H-15, and H-17 appeared downfield in the (R)-derivative relative to the (S)-derivative in $C_6D_6$ (FIGS. 7A and 7B, respectively). That the H-17 on the same face of the molecule as the Mosher ester site was evident from a strong nOe between H-17 and the ester methine, H-15. Similar results were observed in NMR spectra recorded in $CD_3OD$. These data allowed the absolute configuration at C-13 to be assigned as S. The partial structures shown in FIGS. 7A and 7B depict the Newman projections accounting for the observed chemical shift differences. In the (S,S)-diastereomer the H-10 and Me-26 hydrogens experience shielding from the phenyl group, while in the (S,S)-diastereomer H-14a, H-15, and H-17 experience shielding from the phenyl group. If C-13 were of (R)-configuration, just the opposite shielding results would be obtained. As the relative stereochemistry of all three chiral centers had been established, assignment of (S)-configuration at C-13 conferred the (R)-configuration at C-12 and C-15. The absolute configuration is therefore as depicted for salicylihalamide A in FIG. 3.

Accompanying salicylihalamide A in the sponge extract was a minor component whose spectral data were nearly identical to those of salicylihalamide A. Its structure was determined by careful comparison of $^1H$, $^{13}C$, and $^1H$-$^1H$ COSY NMR data in both $C_6D_6$ and $CD_3OD$ with those of salicylihalamide A. The sequence of proton-carbon connectivities was identical to that of salicylihalamide A. The only significant difference between salicylihalamide A and its isomer, salicylihalamide B, was the coupling constant for H-17 and H-18, 10.2 Hz, compared to 14.6 Hz for salicylihalamide A. Thus, salicylihalamide B was the 17-Z isomer of salicylihalamide A.

Lobatamide A, such as obtained and characterized spectroanalytically in Example 1, had a molecular formula of $C_{27}H_{33}N_2O_8$ as established by HRFABMS (noba, m/z 513.2257, MH$^+$, calcd 513.2237). The presence of 3 exchangeable protons was indicated by a CIMS deuterium exchange experiment using $ND_3$ as the ionizing agent. The $^{13}C$ NMR spectrum of lobatamide A (Table 4) contained signals for all 27 carbons, including two ester carbonyls (δ 171.9, 170.0), an amide carbonyl (δ 164.2), 15 sp² carbons (14 of which were accounted for by a phenyl ring and 4 olefins), 3 oxygenated methine carbons (δ 73.8, 73.3, 73.0), 3 methylenes (δ 33.1, 35.6, 38.9), and 3 methyl groups (δ 62.7 (OCH₃), 20.2, 19.6). The ²H and ¹³C NMR data for lobatamide A and lobatamide B are illustrated in Table 4 below. All spectra were recorded in CD₃OD and referenced to residual methanol.

2.48) which was, in turn, coupled to a second trans-olefin ($\delta_C$ 109.9, $\delta_H$ 5.34; $\delta_C$ 126.9, $\delta_H$ 6.82; J=14.2 Hz). The remaining spin system, labeled as fragment E in FIG. 8, consisted of 3 olefinic protons ($\delta_C$ 126.1, $\delta_H$ 6.04; $\delta_C$ 135.6, $\delta_H$ 6.45; and $\delta_C$ 148.7, $\delta_H$ 8.95). Two of these protons ($\delta_H$ 6.04 and $\delta_H$ 6.45, H24 and H25, respectively) formed a cis olefin based on the $J_{24,25}$ of 11.7 Hz and the observed nOe between the protons. Both the chemical shift of the carbon at 148.7 ppm and the downfield shift of its proton to 8.95

| | A | | | B | |
|---|---|---|---|---|---|
| atom # | ¹³C δ (mult.) | ¹H δ (#H, mult., J Hz) | HMBC correl. to C # | ¹³C δ (mult.) | ¹H δ (#H, mult., J Hz) |
| 1 | 170.0 (s) | | | 170.0 (s) | |
| 2 | 122.3 (s) | | | 122.3 (s) | |
| 3 | 156.7 (s) | | | 156.7 (s) | |
| 4 | 114.4 (d) | 6.68 (1H, d, 7.8) | 2, 6 | 114.4 (d) | 6.68 (1H, d, 7.8) |
| 5 | 131.8 (d) | 7.14 (1H, t, 7.8) | 3, 7 | 131.8 (d) | 7.14 (1H, t, 7.8) |
| 6 | 120.8 (d) | 6.63 (1H, d, 7.8) | 2, 4, 8 | 120.9 (d) | 6.63 (1H, d, 7.8) |
| 7 | 141.2 (s) | | | 141.2 (s) | |
| 8a | 33.1 (t) | 3.21 (1H, dd, 17.1, 8.3) | 2, 6, 7, 9, 10 | 33.1 (t) | 3.21 (1H, dd, 8.8, 18.1) |
| b | | 2.93 (1H, br d, 17.1) | | | 2.93 (1H, br d, 18.1) |
| 9 | 125.6 (d) | 5.17 (1H, m) | 11, 25 | 125.6 (d) | 5.17 (1H, m) |
| 10 | 139.4 (s) | | | 139.4 (s) | |
| 11 | 73.3 (d) | 4.78 (1H, d, 8.8) | 9, 10, 12, 13 | 73.3 (d) | 4.78 (1H, d, 8.8) |
| 12 | 135.0 (d) | 5.66 (1H, dd, 15.1, 8.8) | 10, 11, 13 | 135.0 (d) | 5.66 (1H, dd, 15.1, 8.8) |
| 13 | 132.7 (d) | 5.50 (1H, dd, 15.1, 8.3) | 11, 12, 26 | 132.7 (d) | 5.50 (1H, dd, 15.1, 8.3) |
| 14 | 73.8 (d) | 5.23 (1H, dq, 8.3, 6.3) | 12, 15 | 73.8 (d) | 5.23 (1H, dq, 8.3, 6.8) |
| 16 | 171.9 (s) | | | 171.9 (s) | |
| 17a | 38.9 (t) | 2.67 (1H, d, 16.6) | 16, 17 | 38.9 (t) | 2.67 (1H, dd, 16.6, 2.4) |
| b | | 2.59 (1H, dd, 16.6, 10.7) | | | 2.59 (1H, dd, 16.6, 10.7) |
| 18 | 73.0 (d) | 5.58 (1H, m) | 1, 15, 19 | 73.0 (d) | 5.58 (1H, m) |
| 19 | 35.6 (t) | 2.48 (2H, dd, 7.3, 6.3) | 16, 17, 19, 20 | 35.6 (t) | 2.48 (2H, br t, 6.8) |
| 20 | 109.9 (d) | 5.34 (1H, dt, 14.2, 7.8) | 18, 20 | 110.2 (d) | 5.34 (1H, m) |
| 21 | 126.9 (d) | 6.82 (1H, d, 14.2) | 18, 19, 21 | 126.8 (d) | 6.82 (1H, d, 14.2) |
| 23 | 164.2 (s) | | | 164.0 (s) | |
| 24 | 126.1 (d) | 6.04 (1H, d, 11.7) | 21 | 127.9 (d) | 6.05 (1H, d, 11.7) |
| 25 | 135.6 (d) | 6.45 (1H, dd, 11.7, 11.2) | 21 | 127.5 (d) | 7.04 (1H, dd, 11.7, 9.8) |
| 26 | 148.7 (d) | 8.95 (1H, d, 11.2) | 23 | 144.4 (d) | 8.36 (1H, d, 9.8) |
| 28 | 62.7 (q) | 3.91 (3H, s) | | 62.6 (q) | 3.91 (3H, s) |
| 29 | 19.6 (q) | 1.79 (3H, s) | 9, 10, 11 | 19.6 (q) | 1.79 (3H, d, 6.8) |
| 30 | 20.2 (q) | 1.35 (3H, d, 6.3) | 13, 14 | 20.2 (q) | 1.35 (3H, s) |

Figure 8:
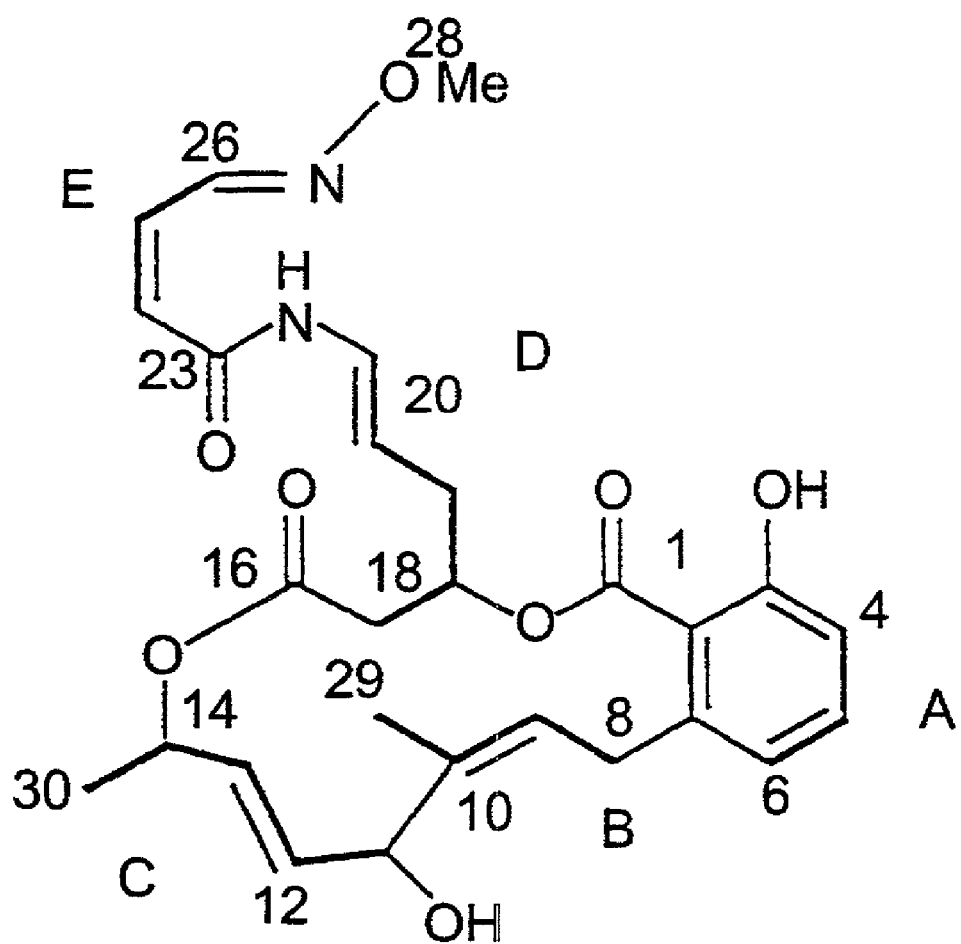
FIG. 8 illustrates the partial structures (shown in bold) as used in the structural analysis of lobatamide A.

A series of NMR experiments, including COSY, difference nOe, HMQC, and HMBC, was used to construct the five partial structures depicted in FIG. 8 by the emboldened bonds (designated as A-E in FIG. 8). Fragment A (FIG. 8) consisted of three adjacent aromatic protons ($\delta_C$ 114.4, $\delta_H$ 6.68, d, J=7.8 Hz; $\delta_C$ 131.8, $\delta_H$ 7.14, t, J=7.8 Hz; $\delta_C$ 120.8, 6, $\delta_H$ 6.63, d, J=7.8 Hz). Fragment B (FIG. 8) consisted of a methylene group ($\delta_C$ 33.1, $\delta_H$ 2.93, dd, J=17.1, 8.3 Hz and $\delta_H$ 3.21, d, J=17.1 Hz) and the olefinic proton of a trisubstituted olefin ($\delta_C$ 125.6, $\delta_H$ 5.17, m; $\delta_C$ 139.4). An HMBC experiment indicated that the singlet methyl group ($\delta_C$ 21.8, $\delta_H$ 1.79) was a substituent on the olefinic carbon at 139.4 ppm which was also correlated to the olefinic proton at 5.17 ppm. The Z-geometry of this olefin was determined from the nOe observed between the methyl group (δ 1.79) and the proton at δ 5.17. Fragment C (FIG. 8) consisted of an oxygenated methine ($\delta_C$ 73.3, $\delta_H$ 4.78) coupled to an olefin ($\delta_C$ 135.0, $\delta_H$ 5.66 and $\delta_C$ 132.7, $\delta_H$ 5.50) designated as trans (E), based on the 15.1 Hz coupling observed between the olefinic protons. The proton at 5.50 ppm was further coupled to a proton residing on another oxygenated carbon ($\delta_C$ 73.8, $\delta_H$ 5.23), which was, in turn, coupled to the doublet methyl resonating at $\delta_H$ 1.35 ($\delta_C$ 20.2). Fragment D (FIG. 8) began with a diastereotopic methylene [$\delta_C$ 38.9, $\delta_H$ 2.67 & 2.59 (J=16.6 Hz)] coupled to an oxygenated methine ($\delta_C$ 73.0, $\delta_H$ 5.53). The methine was coupled to a methylene ($\delta_C$ 35.6, $\delta_H$ ppm suggested that this carbon was bonded to the remaining nitrogen atom in an imine-type bond. In addition, this proton was not correlated to any carbons except the neighboring olefin, already identified as part of fragment E. The carbon chemical shift of 148.7 was consistent with the presence of an oxime (Gordon et al., *J. Org. Chem.*, 49, 97-100 (1984)), and such a functional group accounted for the remaining nitrogen and oxygen atoms required by the molecular formula. The presence of a H25-H26 coupling constant near 11 Hz, plus the nOe correlations observed between those two protons, suggested that the olefin and oxime were in a s-cis relationship. These partial structures account for all of the structural elements of lobatamide A except for the methoxyl group. The methoxyl functionality was, in the end, placed on the oxime at N27 based on its carbon chemical shift ($\delta_C$ 62.7), which was consistent with other oxime methyl ethers and supported by the weak nOe observed between the methoxyl signal at 3.91 ppm and the proton at 8.95 ppm (H26). The observed nOe and the chemical shifts of the oxime carbon and proton supported E (syn) geometry for the oxime double bond (Gordon et al., *J. Org. Chem.*, 49, 97-100 (1984); Wolkowski et al., *Tetrahedron Lett.*, 565-568 (1972)). The presence of an oxime methyl ether was also supported by MS data (vide infra).

Figure 9:
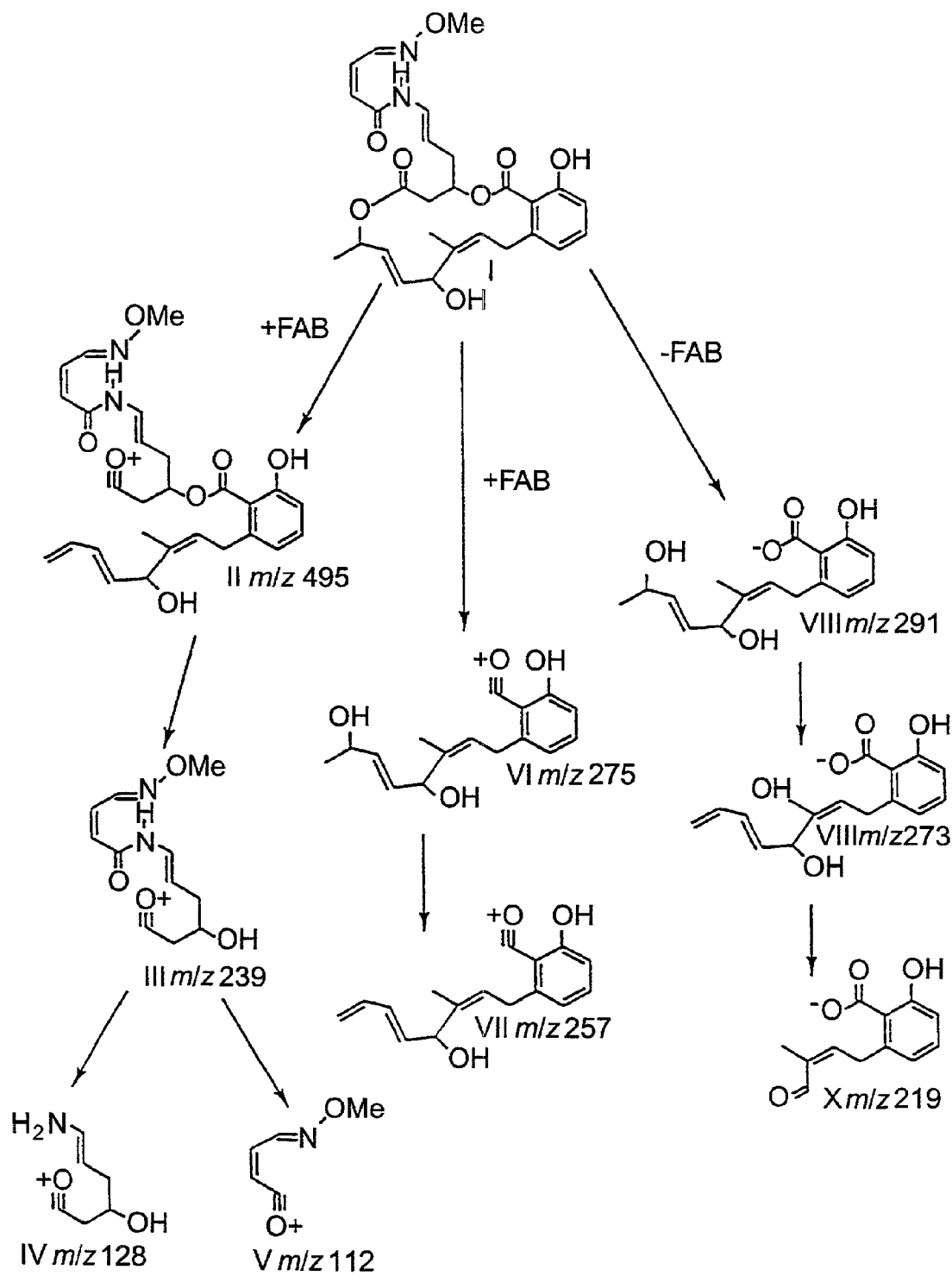
FIG. 9 illustrates the mass spectrometric fragmentation analysis for lobatamide A.

The substitution pattern around the phenyl ring of fragment A (FIG. 9) was determined based on HMBC experiments optimized for 8.3 and 5.5 Hz couplings. The aromatic proton at δ 7.14 (H5), which was coupled to two ortho protons, was correlated to both a phenol carbon at δ 156.7, and a second, quaternary carbon at δ 141.2, suggesting that both were meta to this proton. The carbon at δ 141.2 was further correlated to the methylene protons at C8, thus identifying it as C7 and requiring attachment of that methylene to this carbon. Correlations to H6 (δ 6.63) were observed from δ 114.4 (C4), 122.3 (C2) and the terminal carbon of the side chain (δ 33.1), placing the side chain ortho to C6 at C7. This left C2 (δ 122.3) as the only point of attachment for the ester carbonyl at δ 170.0 (C1).

Fragments A and B (FIG. 8) were connected through C7, based on HMBC correlations of that carbon to protons at δ 7.14 (H5), δ 6.63 (H6), and δ 3.21 (H8a). Additional correlations supporting this connection were those between H6 and C8, H8 and C2, and H8 and C6. Correlations from C10 to H11 and H12, along with those observed to H29 from C9, C10, and C11, provided the connection between fragments B and C (FIG. 8). The correlation between H14 and the ester carbonyl at δ 171.9 (C16), which was further correlated to both protons on C17 (δ 2.59, 2.67), as well as H18, provided the connection between fragments C and D (FIG. 8). H18 (δ 5.58) was further correlated to the second ester carbonyl at δ 170.0 (C1), which was previously linked to fragment A at C2 (FIG. 8). Finally, fragments D and E (FIG. 8) were linked through an amide bond based on the observed correlations between the carbonyl at δ 164.2 and protons at H21, H24, and H25. Thus, HMBC experiments provided the final data leading to the gross structure of lobatamide A.

Additional, critical support for the structure of lobatamide A was provided by mass spectrometry (see methodology and data from Example 1). Deuterium exchange experiments provided results consistent with a structure with 3 exchangeable protons. Lobatamide A fragmented to give several structurally significant ions (FIG. 9), the sequence of which was determined by linked scan analyses of the fragment ions. In positive ion mode, elimination of a water molecule dominated the upper mass range to give a peak at m/z 495 (II). Although there is more than one structure that can be drawn for this ion, II is based on subsequent fragmentation and deuterium exchange data. Cleavage of the second ester bond yielded a dominant ion at m/z 239 (III) characteristic of the upper half of the molecule. This further fragmented to yield ions at m/z 128 (IV) and m/z 112 (V). This latter fragment (V, m/z 112) strongly supported location of the methoxyl on an oxime. Initial fragmentation at the other ester bond yielded fragment ions at m/z 275 (VI) and then m/z 257 (VII). In negative ion mode, fragmentation was dominated by cleavage at both ester bonds to yield ions at m/z 291 (VIII), m/z 273 (IX), and m/z 219 (X), further characterizing the macrocyclic ring. Upon acetylation, lobatamide A yielded a diacetate, m/z 596, which, on fragmentation in positive ion mode, gave further support to the lobatamide A structure (fragment ions comparable to II, VI, and VII showed two acetylations, while analogous structure III, IV and V showed no change).

Lobatamide B was isomeric with lobatamide A. Indeed, the only significant difference in the $^1$H NMR spectrum of lobatamide B was the downfield shift of H25 to 7.04 ppm (vs. 6.45 ppm in lobatamide A) and the upfield shift of H26 to 8.36 ppm (vs. 8.95 ppm in lobatamide A). The upfield shift of this proton is consistent with Z (anti) geometry about the oxime bond. These shifts in the proton spectrum were accompanied by similar changes in the corresponding carbon signals, with C25 appearing at δ 127.5, upfield from 135.6 ppm in lobatamide A, and C26 moving upfield to 144.4 ppm (vs. δ 148.7 in lobatamide A). These differences indicated that the geometry of the oxime methyl ether was changed to Z in lobatamide B. No nOe was observed between the oxime OMe and H26, as was seen with lobatamide A. The mass spectrum of lobatamide B showed essentially the same fragmentations as those seen in lobatamide A, further supporting that only the geometry of the oxime had changed in lobatamide B.

Example 3

This example illustrates the isolation and structure of particular compounds of the present invention, Lobatamides C-F.

Lobatamides C-F were isolated from *Aplidium lobatum*, and the structures elucidated, according to procedures analogous to those described in Examples 1 and 2 for lobatamides A and B. Lobatamide C, was shown by HRFABMS to be isomeric with lobatamides A and B, namely $C_{27}H_{32}N_2O_8$. As with the latter compounds, the presence of three exchangeable protons was indicated by a CIMS deuterium exchange experiment using $ND_3$ as the ionizing agent. The structural similarities among the three compounds were clearly evident from both the $^{13}$C and $^1$H NMR spectra (Tables 4-6). The $^{13}$C NMR spectrum of lobatamide C contained signals for all 27 carbons, including two ester carbonyls (δ 171.7, 169.9); an amide carbonyl (δ 164.1); 15 $sp^2$ carbons, fourteen of which were accounted for a phenyl ring and four olefins; three oxygenated methine carbons (δ 73.7, 73.2, 72.9); three methylenes (δ 33.0, 35.5, 38.8); and three methyl groups (δ 62.7 ($OCH_3$), 20.2, 19.5).

Based on a standard series of one- and two-dimensional NMR experiments, which included HMQC and HMBC, the five spin systems illustrated in FIG. 8 (labeled as regions A-E) for lobatamide A could also be identified for lobatamide C. Of the five spin systems defined, only one system (FIG. 8, region E) was different from those found in lobatamides A and B. This system contained a trans olefin based on the 15.1 Hz coupling constant between H24 and H25. This coupling constant was 11.7 Hz for both lobatamides A and B. For lobatamide C, the configuration of the oxime methyl ether was assigned as E based on the carbon chemical shifts for C26 and C25 at $δ_c$ 149.3 and 135.5, respectively; in addition, the one bond $J_{CH}$ of C26 was 175 Hz.

Fragments A and B (FIG. 8, regions A and B, respectively) were connected through C7, based on HMBC correlations of that carbon to protons at δ7.14 (H5) and δ 3.21 (H8a). Additional correlations supporting this connection were those between H6 and C8, and H8 and C2. Correlations from C10 to H11 and H12, along with those observed to H29 from C9, C10 and C11, provided the connection between fragments B and C (FIG. 8, regions B and C, respectively). The correlation between H14 and the ester carbonyl at δ 171.7 (C16), which was further correlated to both protons on C17 (δ 2.60, 268), as well as H18, provided the connection between fragments C and D (FIG. 8, regions C and D, respectively). H18 (δ 5.60) was further correlated to the second ester carbonyl at δ 169.9 (C1), which was previously linked to fragment A at C2. Finally, fragments D and E (FIG. 8, regions D and E, respectively) were linked through an amide bond, based on the observed correlations between the carbonyl at δ 164.1 (C23) and H24 and H25. No correlation between H21 and C23 was observed in the HMBC experiments; however, the presence of the amide bond was supported by the similarities of both the $^1$H and $^{13}$C NMR spectra. Thus, HMBC experiments led to the gross structure of lobatamide C; furthermore, as with lobatamides A and B, the deduced structure for lobatamide C was further confirmed by linked scan mass spectrometry. In all three cases, the identification of the same molecular formula and observation of the same fragmentations (see FIG. 8) supported the three structures as geometric isomers.

The three additional isolated compounds, lobatamides D-F, all had a molecular formula of $C_{27}H_{32}N_2O_9$, indicating the presence of one more oxygen than lobatamides A-C. Deuterium-exchange CIMS experiments confirmed that the extra oxygen could be accounted for by an additional hydroxyl group in the latter four compounds. The $^{13}C$ and $^1H$ NMR data (Tables 5 and 6, respectively) further revealed the structures of lobatamides D-F.

For lobatamide D, a standard set of one and two-dimensional NMR experiments was obtained to identify the five spin systems present; of these, four (regions A-C and E depicted in FIG. 8) were identical to those of lobatamide A. Fragment D (corresponding to region D of FIG. 8), however, terminated in a hydroxy methylene ($\delta_C$ 64.2; $\delta_H$ 3.70, dd, J=12.1, 7.8 Hz; 3.65, dd, J=12.1, 3.9 Hz) rather than a methyl group. Linked scan mass spectrometry studies of lobatamide D indicated that several of the fragment ions differed by 16 amu relative to those of lobatamides A-C. These ions included II (to m/z 511), VI (to m/z 291), VII (to m/z 273), VIII (to m/z 307), and IX (to m/z 289). In addition, fragment VII lost the elements of water to yield an ion at m/z 255, thus establishing the C30 location of the extra hydroxyl group in lobatamide D. The carbon and proton chemical shifts and $J_{CH}$ values closely matched those reported for lobatamide A, indicating that both compounds possessed the same geometries at the $\Delta^{24,25}$-olefin and the oxime bonds.

Comparison of the $^1H$ and $^{13}C$ NMR spectra obtained for lobatamides D and E suggested they differed only in the geometry of the oxime methyl ether functionality. The chemical shift for the oxime carbon (C26) in lobatamide E appeared upfield relative to that for lobatamide D (144.5 ppm and 148.7 ppm, respectively), as was that for C25 (127.6 and 135.9 ppm for lobatamides E and D, respectively). These differences in the carbon spectra were paralleled by an analogous upfield shift of the signal for H26 (8.36 ppm for lobatamide E relative to 8.95 ppm for lobatamide D). In addition, the one bond heteronuclear coupling constant for C26 in lobatamide E was 190 Hz. These data indicated that the oxime methyl ether was of Z-geometry, as was the case with lobatamide B. A comparison of the spectral data for lobatamides B and E showed a close correlation between the chemical shifts in both the $^1H$ and $^{13}C$ spectra, supporting the structure of lobatamide E.

A comparison of the $^1H$ and $^{13}C$ spectra and a series of NMR experiments confirmed the gross structure of lobatamide F. As with lobatamide C, the C24-C25 olefin had E geometry based on the 15.6 Hz coupling constant. The consistent coupling constant of 10 Hz between H25 and H26, as well as the NOE observed between the two protons, indicated that the olefin-oxime bonds were in an s-cis relationship. Finally, the carbon chemical shifts of C26 (149.4 ppm) and C25 (135.5 ppm) corresponded closely with those of lobatamides A, C and D, and were downfield of the C25 and C26 shifts of lobatamides B and E. In addition, the one bond heteronuclear coupling constant of 178 Hz was consistent with those of the other lobatamides possessing E-geometry at the oxime bond.

Additional physicochemical and spectroanalytical data for lobatamides C-F were as follows. Lobatamide C: $[\alpha]_D$ −15.5° (c 0.113, MeOH); UV (MeOH) $\lambda_{max}$ 280 (log $\epsilon$4.04) nm; IR (film) $v_{max}$ 3590-3108 (br), 3067, 2975, 2933, 1733, 1656, 1616, 1584, 1467, 1451, 1354, 1267, 1215, 1175, 1113, 1042, 959, 790 cm$^{-1}$; HRFABMS (magic bullet) MNa$^+$ m/z 535.2065, calcd. for $C_{27}H_{33}N_2O_8$ 513.2255; FABMS (m-bullet) m/z 551 (MNa$^+$, 55%), 535 (60), 495 (20), 257 (32), 239 (50), 193 (100). Lobatamide D: $[\alpha]_D$ −35.0° (c 0.08, MeOH); UV (MeOH) $\lambda_{max}$ 281 (log $\epsilon$4.23) IR (film) $v_{max}$ 3593-3123 (br), 2924, 1738, 1650, 1607, 1529, 1464, 1450, 1269, 1218, 1168, 1117, 1042, 964, 755 cm$^{-1}$; HRFABMS (m-bullet) MH$^+$ m/z 529.2164, calcd. for $C_{27}H_{33}N_2O_9$ 529.2186; FABMS (noba) m/z 551 (MNa$^+$, 100%), 529 (6), 511 (10), 239 (12). Lobatamide E: $[\alpha]_D$ −26.7° (c 0.06, MeOH); UV (MeOH) $\lambda_{max}$ 282 (log $\epsilon$4.25) IR (film) $v_{max}$ 3591-3110 (br), 2924, 1734, 1652, 1539, 1269, 1046, 668 cm$^{-1}$; HRFABMS (m-bullet) MH$^+$ m/z (529.2184), calcd. for $C_{27}H_{33}N_2O_9$ 529.2186; FABMS (glyc) m/z 551 (MNa$^+$, 5%), 511 (17), 239 (33), 217 (30), 112 (100). Lobatamide F: $[\alpha]_D$ −19.2° (c 0.067, MeOH); UV (MeOH) $\lambda_{max}$ 280 (log $\epsilon$4.17) IR (film) $v_{max}$ 3591-3108 (br), 2912, 1737, 1657, 1607, 1525, 1481, 1268, 1214, 1167, 1114, 1042, 973, 755, 668 cm$^{-1}$; HRFABMS (noba) MNa$^+$ m/z 551.2015, calcd. for $C_{27}H_{33}N_2O_9$ 529.2186; FABMS (magic bullet) m/z 551 (MNa$^+$, 50), 511 (20), 301 (40), 239 (10), 112 (100).

The $^{13}C$ NMR data (125 MHZ, CD$_3$OD) for Lobatamides C-F are illustrated below in Table 5. The $^1H$ NMR Data (500 MHz, CD$_3$OD) for Lobatamides C-F are illustrated below in Table 6.

TABLE 5

| C # | Lobatamide C | Lobatamide D | Lobatamide E | Lobatamide F |
| --- | --- | --- | --- | --- |
| 1 | 169.9 | 169.9 | 170 | 170 |
| 2 | 122.2 | 122.3 | 122.3 | 122.2 |
| 3 | 156.6 | 156.6 | 156.7 | 156.6 |
| 4 | 114.2 | 114.4 | 114.4 | 114.4 |
| 5 | 131.7 | 131.9 | 131.9 | 131.9 |
| 6 | 120.8 | 120.8 | 120.9 | 120.9 |
| 7 | 141.1 | 141.2 | 141.2 | 141.2 |
| 8 | 33 | 33.1 | 33.1 | 33.1 |
| 9 | 125.5 | 125.7 | 125.7 | 125.7 |
| 10 | 139.4 | 139.4 | 139.4 | 139.4 |
| 11 | 73.2 | 73.4 | 73.4 | 73.4 |
| 12 | 134.9 | 137.6 | 137.6 | 137.4 |
| 13 | 132.6 | 128.1 | 128.1 | 128.2 |
| 14 | 73.7 | 78.4 | 78.1 | 78.4 |
| 16 | 171.7 | 172.1 | 172.1 | 172.1 |
| 17 | 38.8 | 38.9 | 38.9 | 38.9 |
| 18 | 72.9 | 73.1 | 73.1 | 73.1 |
| 19 | 35.5 | 35.6 | 35.6 | 35.6 |
| 20 | 110.2 | 109.8 | 110.2 | 110.2 |
| 21 | 126.9 | 126.9 | 126.9 | 126.9 |
| 23 | 164.1 | 164.3 | 164.2 | 164.2 |
| 24 | 130.2 | 126.1 | 127.9 | 130.2 |
| 25 | 135.5 | 135.9 | 127.6 | 135.5 |
| 26 | 149.2 | 148.7 | 144.5 | 149.4 |
| 28 | 62.7 | 62.7 | 62.6 | 62.8 |
| 29 | 19.5 | 19.6 | 19.7 | 19.7 |
| 30 | 20.2 | 64.2 | 64.2 | 64.2 |

TABLE 6

| C # | Lobatamide C $^1H$ (mult., J Hz) | Lobatamide D $^1H$ (mult., J Hz) | Lobatamide E $^1H$ (mult., J Hz) | Lobatamide F $^1H$ (mult., J Hz) |
| --- | --- | --- | --- | --- |
| 2 | 6.68 (d, 8.3) | 6.68 (d, 7.8) | 6.68 (d, 8.3) | 6.68 (d, 7.8) |
| 5 | 7.14 (dd, 7.8, 8.3)[a] | 7.14 (dd, 7.8, 7.8) | 7.14 (dd, 7.8, 8.3) | 7.14 (dd, 7.3, 7.8)[b] |
| 6 | 6.63 (d, 7.8) | 6.63 (d, 7.8) | 6.63 (d, 7.8) | 6.63 (d, 7.3) |
| 8a | 3.21 (dd, 8.8, 17.6) | 3.25 (dd, 8.8, 17.1) | 3.25 (dd, 9.3, 17.6) | 3.21 (dd, 8.8, 17.6) |

TABLE 6-continued

| C # | Lobatamide C $^1$H (mult., J Hz) | Lobatamide D $^1$H (mult., J Hz) | Lobatamide E $^1$H (mult., J Hz) | Lobatamide F $^1$H (mult., J Hz) |
|---|---|---|---|---|
| b | 2.95 (br d, 17.6) | 2.96 (br d, 17.1) | 2.95 (br d, 17.6) | 2.95 (br d, 17.6) |
| 9 | 5.17 (m) | 5.20 (m) | 5.18 (m) | 5.17 (m) |
| 11 | 4.79 (d, 8.8) | 4.80 (d, 8.3) | 4.79 (d, 8.8) | 4.79 (d, 8.8) |
| 2 | 5.67 (dd, 8.8, 15.1) | 5.76 (dd, 6.6, 15.6) | 5.75 (dd, 8.8, 15.1) | 5.78 (dd, 8.8, 15.6) |
| 13 | 5.50 (dd, 8.8, 15.1) | 5.48 (dd, 9.3, 15.6) | 5.50 (dd, 9.3, 15.1) | 5.50 (dd, 8.8, 15.6) |
| 14 | 5.23 (dq, 8.8, 6.4) | 5.16 (m) | 5.16 (m) | 5.14 (m) |
| 17a | 2.68 (dd, 2.4, 16.6) | 2.73 (dd, 2.0, 16.6) | 2.73 (dd, 2.4, 16.6) | 2.73 (dd, 2.4, 16.6) |
| b | 2.60 (dd, 10.8, 16.6) | 2.67 (dd, 10.7, 17.1) | 2.67 (dd, 10.2, 16.6) | 2.67 (dd, 10.7, 16.6) |
| 18 | 5.60 (m) | 5.58 (m) | 5.60 (m) | 5.61 (m) |
| 19 | 2.48 (2H, m) | 2.48 (2H, br t, 6.8) | 2.48 (2H, br t, 6.8) | 2.48 (2H, br t, 6.8) |
| 20 | 5.37 (dt, 7.8, 14.6) | 5.34 (dt, 7.8, 14.2) | 5.35 (dt, 7.3, 14.2) | 5.37 (dt, 7.3, 14.2) |
| 21 | 6.87 (d, 14.6) | 6.82 (d, 14.6) | 6.83 (d, 14.2) | 6.87 (d, 14.2) |
| 24 | 6.28 (d, 15.1) | 6.05 (d, 11.2) | 6.05 (d, 11.7) | 6.28 (d, 15.6) |
| 25 | 7.14 (dd, 10.2, 15.1)[a] | 6.49 (dd, 10.2, 11.2) | 7.03 (dd, 9.8, 11.7) | 7.13 (dd, 9.8, 15.6)[b] |
| 26 | 7.86 (d, 10.2) | 8.95 (d, 10.2) | 8.36 (d, 9.8) | 7.85 (d, 9.8) |
| 28 | 3.91 (3H, s) | 3.89 (3H, s) | 3.89 (3H, s) | 3.91 (3H, s) |
| 29 | 1.79 (3H, s) | 1.79 (3H, s) | 1.80 (3H, s) | 1.78 (3H, s) |
| 30a | 1.34 (3H, d, 6.3) | 3.70 (dd, 7.8, 12.1) | 3.70 (dd, 7.3, 12.2) | 3.70 (dd, 7.3, 11.7) |
| b |  | 3.65 (dd, 3.9, 12.1) | 3.65 (dd, 3.9, 12.2) | 3.65 (dd, 3.9, 11.7) |

[a,b]overlapping multiplets

Example 4

This example illustrates the general procedure for obtaining the activity profile of compounds of the present invention using the NCI 60 cell-line screen. In this example, salicylihalamide A and lobatamide A were tested, as follows. The Compounds were tested in the NCI 60 cell-line screen as described in detail in Boyd and Paull, *Drug Dev. Res.*, 34, 91-109 (1995); and Monks et al., *J. Natl. Cancer Inst.*, 83, 757-766 (1991). Briefly, stock solutions of the compounds were prepared initially in dimethylsulfoxide at 400× the desired final highest test concentrations and stored at −70° C. until use. The final highest test concentrations studied in this example varied between $10^{-5}$ and $10^{-8}$ molar. At the time of screening, an aliquot of the thawed stock was diluted with complete medium containing 50 μg/ml gentamycin to give a concentration of 2× the desired final highest test concentration. Four additional 10-fold serial dilutions were then made to provide a total of five concentrations, spanning a 4-$\log_{10}$ concentration range. One hundred μl aliquots of these intermediate dilutions were immediately added to the appropriate microtitre wells, each already containing the appropriate numbers and types of cells in 100 μl of culture medium, resulting in the desired five final concentrations.

The 60 cell lines used, and the respective inoculation densities, were as described in Boyd and Paull, *Drug Dev. Res.*, 34, 91-109 (1995), and Monks et al., *J. Natl. Cancer Inst.*, 83, 757-766 (1991). Following the compound additions, the plates were incubated for 48 h at 37° C. under a 5% $CO_2$/air atmosphere and 100% humidity. Then, adherent cells (all lines except the leukemia) were fixed in situ by gentle addition of cold trichloroacetic acid (50 μl of 50% w/v) and incubated for 60 min at 4° C. Supernatants were discarded, and plates were washed five times with deionized water and air dried. Sulforhodamine B solution (SRB; 100 μl at 0.4% w/v in 1 acetic acid) was added to each plate, followed by further incubation for 10 min at room temperature. Excess unbound dye was then removed by washing five times with 1% acetic acid, followed by air drying. The bound stain in each well was solubilized by addition of 100 μl of 10 mM unbuffered Tris base; this was followed by a determination of optical densities (515 nm) on an automated plate reader. For suspension cell cultures (the leukemias), the method was the same except that at the end of the drug incubation period the settled cells were fixed in situ to the bottoms of the microtitre wells by gentle addition of 50 μl of 80% trichloroacetic acid. Appropriate control wells were included in the test plate format (Monks et al., *J. Natl. Cancer Inst.*, 83, 757-766 (1991)) to allow subtraction of background optical densities, drug-blank corrections, and a determination of cell densities at time 0 (the time at which compounds are added).

The quadruplicate testing of pure salicylihalamide A in the NCI 60 cell-line screen gave the following averaged, individual negative $\log_{10}$ $GI_{50}$ values shown along with the respective subpanel and cell-line identifiers: (Leukemia) CCRF-CEM (7.89), HL-60-TB (9.04), K-562 (8.41), MOLT-4 (7.96), RPMI-8226 (7.89), SR (8.44); (Lung) A549/ATCC (8.54), EKVX (7.52), HOP-62 (8.38), HOP-92 (7.77), NCI-H226 (8.80), NCI-H23 (6.55), NCI-H322M (6.72), NCI-H460 (9.01), NCI-H522 (7.26); [Colon] COLO 205 (8.07), HCC-2998 (6.74), HCT-116 (8.74), HCT-15 (8.44), HT29 (8.54), KM12 (8.30), SW-620 (7.54); (Brain) SF-268 (7.55), SF-295 (8.96), SF-539 (7.89), SNB-19 (6.47), SNB-75 (6.21), U251 (7.57); (Melanoma) LOX-IMVI (9.11), MALME-3M (7.62), M14 (8.92), SK-MEL-2 (7.47), SK-MEL-28 (7.00), SK-MEL-5 (9.00), UACC-257 (8.47), UACC-62 (8.38); (Ovary) IGROV1 (7.89), OVCAR-3 (7.03), OVCAR-4 (5.30), OVCAR-5 (8.11), OVCAR-8 (8.43), SK-OV-3 (5.54); (Kidney) 786-0 (7.92), A498 (6.55), ACHN (8.01), CAKI-1 (8.96), RXF-393 (9.07), SN-12C (7.77), TK-10 (5.74), UO-31 (8.31); (Prostate) PC-3 (7.51), DU-145 (8.26); [Breast] MCF-7 (7.12), MCF-7-ADR-RES (8.07), MDA-MB-231/ATCC (6.92), HS-578T (5.85), MDA-MB-435 (7.82), MDA-N (8.00), BT-549 (9.30), T-47D (8.34).

$GI_{50}$ and TGI-COMPARE analyses of the full data set obtained from the screening of salicylihalamide A revealed that the compound gave a striking pattern of differential cytotoxicity in the NCI 60 cell-line screen that is characteristic of certain compounds of the present invention (e.g., Pearson correlation coefficients greater than or equal to 0.7-0.8 with lobatamides A and B) but unlike that of any known conventional anticancer drug class. COMPARE pattern-recognition analyses of the mean graph profile of salicylihalamide A did not reveal any significant correlation to the profiles of known anticancer compounds contained in the NCI's standard agents database. The mean panel $GI_{50}$ concentration of salicylihalamide A was approximately 15 nM, and the range of differential sensitivity among the 60 cell-lines comprising the NCI panel was greater than or equal to $10^3$.

Similarly, the triplicate testing of lobatamide A (FIGS. 10A-10C) and lobatamide B in the NCI 60 cell-line screen yielded mean-graph profiles that correlated highly with each other (e.g., TGI-COMPARE Pearson correlation coefficients greater than or equal to 0.9) and highly characteristic of certain compounds of the present invention (e.g., TGI-COMPARE Pearson correlation coefficients with salicylihalamide A of greater than or equal to 0.7-0.8). Lobatamide D, lobatamide E, and lobatamide F also were tested in accordance with this example.

These data can be used to generate mean graph "fingerprints," which can be used to identify a molecular target for a particular compound or class of compounds. The molecular target (and, therefore, the biological activity) for a particular compound can be determined by correlating the mean graph "fingerprints" of the compound in question with those of prototype ("seed") compounds, as demonstrated further in Example 5.

Figure 10A:
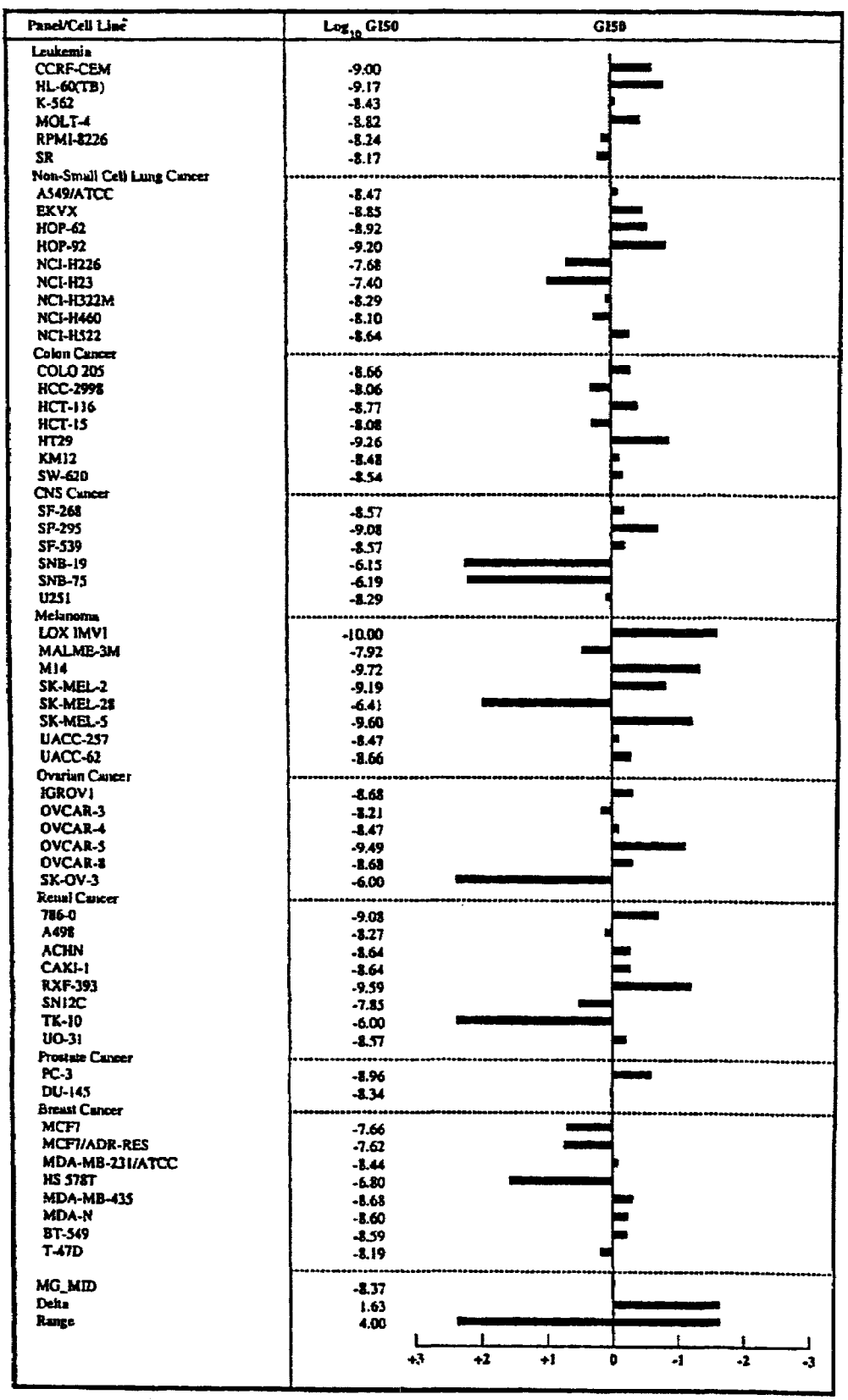
FIG. 10A illustrates the $GI_{50}$-based mean-graph "fingerprint" of lobatamide A in the NCI 60 cell-line screen.
Figure 10B:
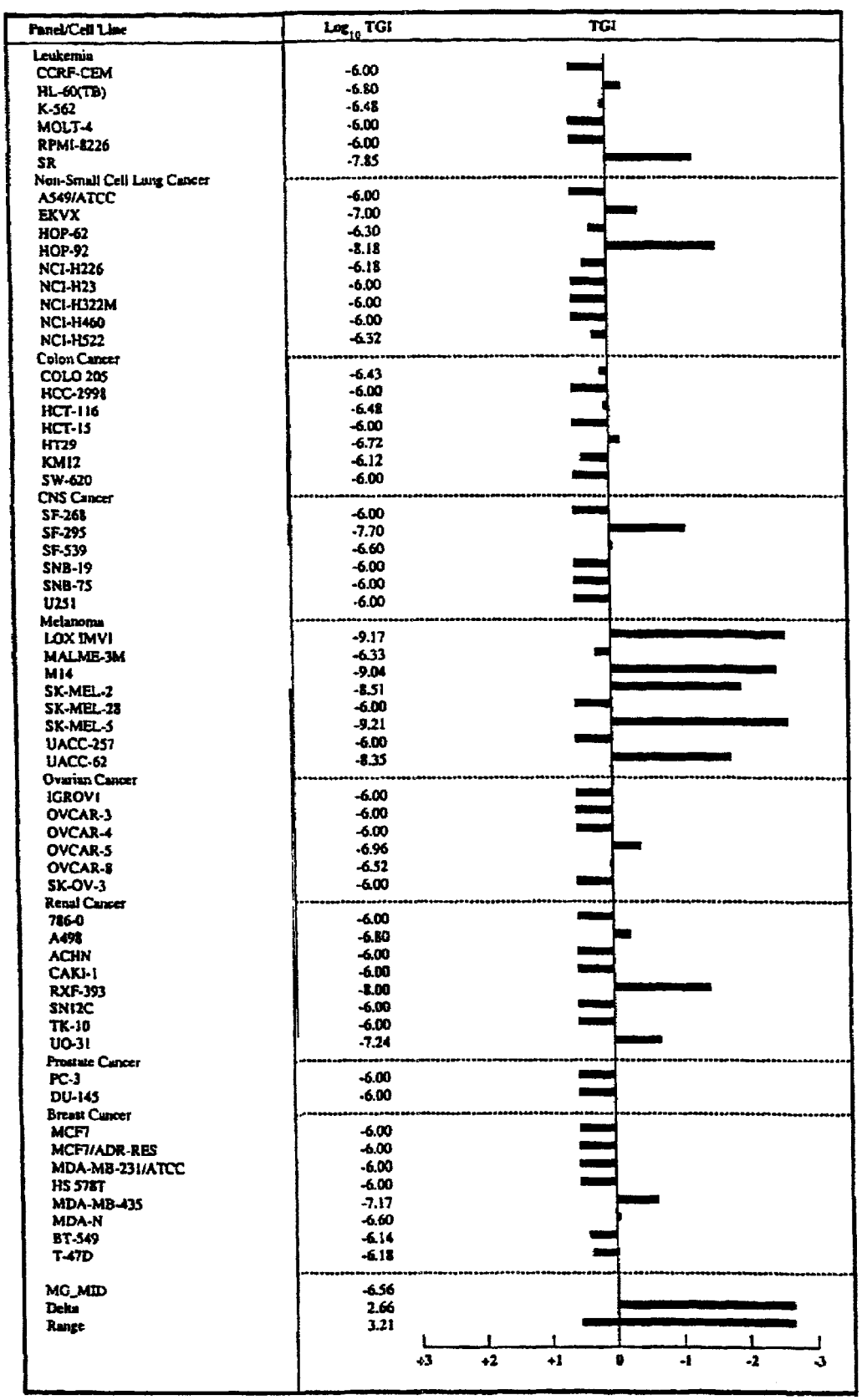
FIG. 10B illustrates the TGI-based mean-graph "fingerprint" of lobatamide A in the NCI 60 cell-line screen.
Figure 10C:
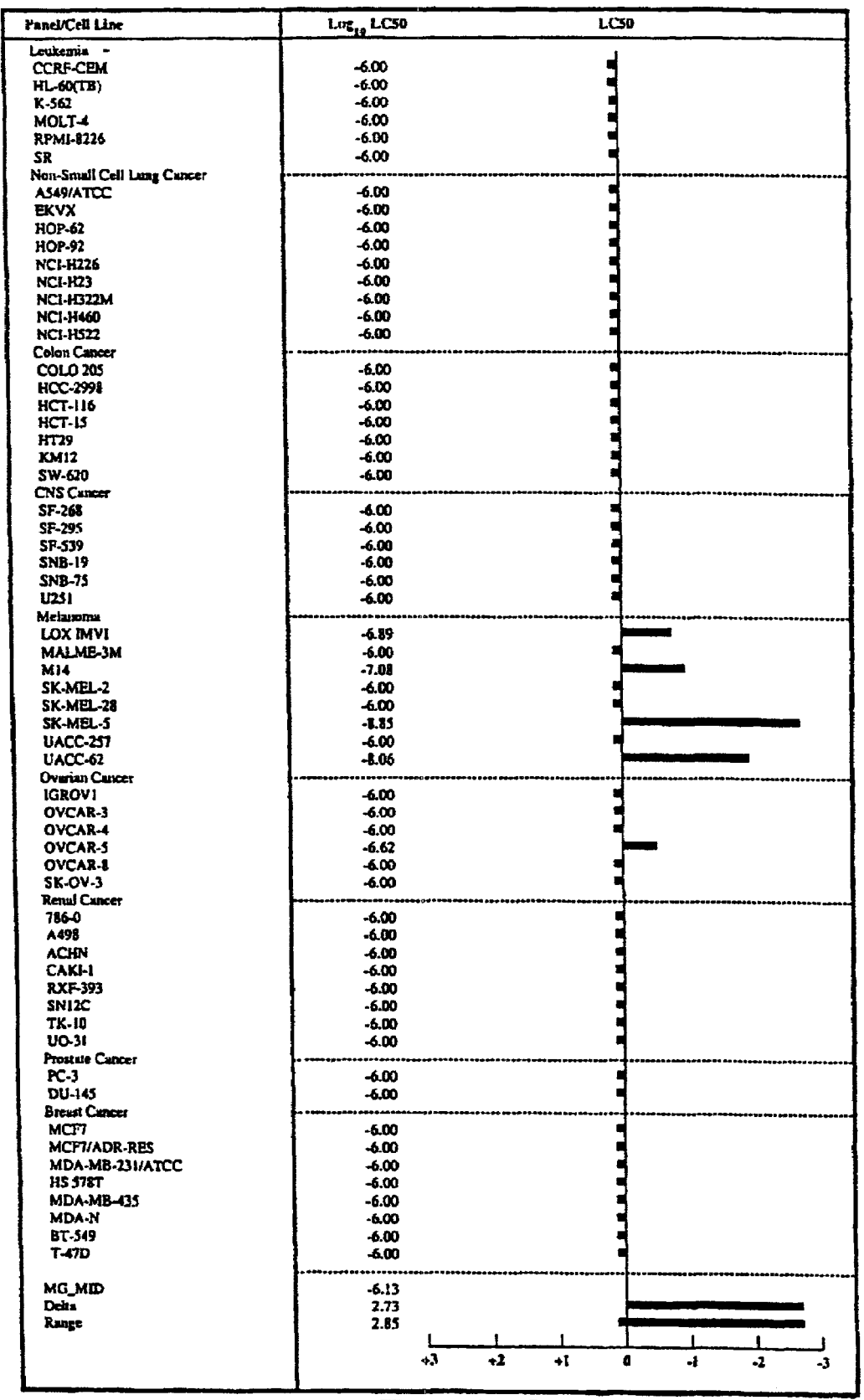
FIG. 10C illustrates the $LC_{50}$-based mean-graph "fingerprint" of lobatamide A in the NCI 60 cell-line screen.

Representative mean graph "fingerprints" for lobatamides A and D, obtained in the NCI 60 cell-line screen, were generated. The mean graph "fingerprints" for lobatamide A, obtained in the NCI 60 cell-line screen, are graphically depicted in FIGS. 10A-10C. FIG. 10A graphically represents the $GI_{50}$ mean graph "fingerprint" for lobatamide A. FIG. 10B graphically represents the TGI mean graph "fingerprint" for lobatamide A. FIG. 10C graphically represents the $LC_{50}$ mean graph "fingerprint" for lobatamide A.

Example 5

This example demonstrates the vacuolar-type (H+)-ATPase inhibitory activity of particular compounds of the present invention. This method employs the NCI 60 cell-line in vitro screen to obtain a mean-graph "fingerprint" of a desired mechanistic prototype compound, then using a computer-based search algorithm called COMPARE, to search a database or mean-graph "fingerprints" of structurally unrelated compounds, to thereby identify compounds with fingerprints very similar if not indistinguishable, from that of the selected prototype (or "seed"). The degree of similarity is determined by calculation of a COMPARE correlation coefficient, which can vary from a lowest value of zero (which indicates no correlation), to a highest value of one (which indicates a perfect correlation). A high COMPARE correlation (i.e., indicating a high degree of similarity) between the mean-graph "fingerprints" of different compounds indicates that the compounds act on the same or similar molecular target and therefore share essentially the same or similar mechanism of biological activity. In practical terms, a COMPARE correlation coefficient of about 0.9 or higher indicates that, within the limits or experimental error of the screening process, the mean-graph "fingerprints" of the compared compounds are essentially identical or indistinguishable, and therefore that the compounds act on the same molecular target. For pertinent background on the NCI 60 cell-line screen and the method and applications of COMPARE, see Boyd, In: *Current Therapy in Oncology* (Niederhuber, J. E., ed) Philadelphia: B. C. Decker, 1993, pp. 11-22; Boyd and Paull, *Drug Dev. Res.*, 34, 91-109, 1995; Paull et al., In: *Cancer Chemotherapeutic Agents*, Washington, D.C.: Am. Chem. Soc. Books, 1995, pp. 11-45.

Figure 11A:
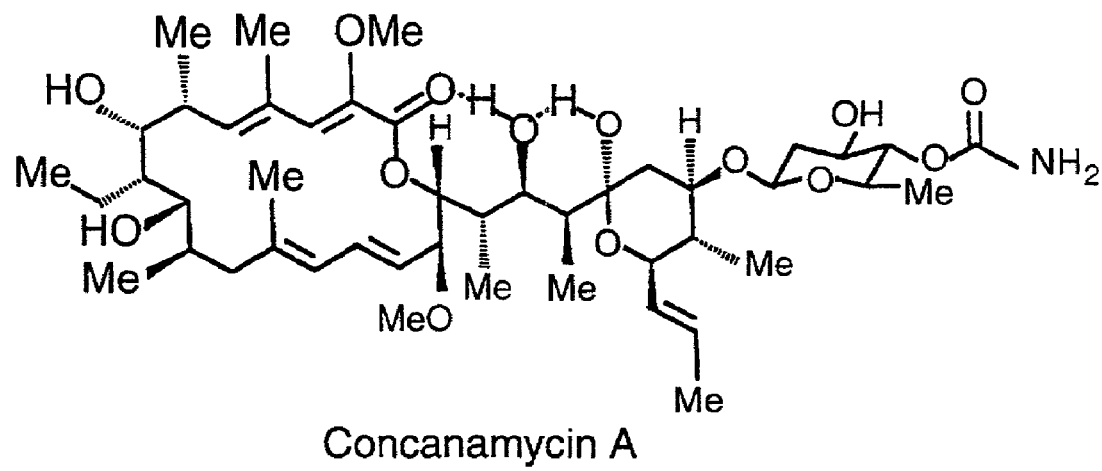
FIG. 11A illustrates the structure of concanamycin A.
Figure 11B:
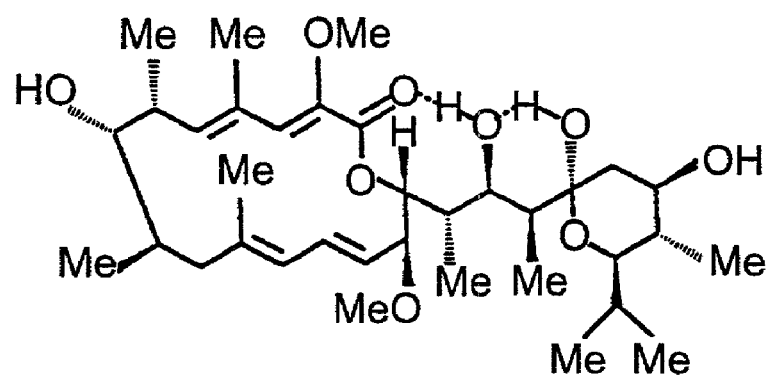
FIG. 11B illustrates the structure of bafilomycin $A_1$.

The most potent heretofore known vacuolar-type (H+)-ATPase inhibitor, concanamycin A (see FIG. 11A), was selected as the mechanistic prototype (or "seed") to use in a COMPARE analysis for purposes of this example. Another known, albeit less potent, vacuolar-type (H+)-ATPase inhibitor, bafilomycin $A_1$ (see FIG. 11B) was selected for use as a "positive control". For pertinent background on concanamycins and bafilomycins, see Bowman et al., *Proc. Natl. Acad. Sci.* USA, 85, 7972-7976 (1988); Dröse et al., *Biochemistry*, 32, 3902-3906 (1993); Dröse and Altendorf, *J. Exp. Biol.*, 200, 1-8 (1997).

The initial selection of concanamycin A and bafilomycin $A_1$ originally was based upon surveillance (e.g., see Boyd and Paull, *Drug Dev. Res.* 34, 91-109, 1995) of NCI databases for higher-than-chance (e.g., COMPARE correlation coefficients 0.5) with the "fingerprints" of known mechanistic prototype compounds of interest (e.g., concanamycin A) contained in the NCI's historical databases. In the present example, authentic, well-characterized and documented reference samples of concanamycin A and bafilomycin $A_1$ were obtained from a commercial supplier (Kamiya Biochemical Company, Tukwila, Wash.). Exemplary test compounds of the present invention selected for this example included salicylihalamide A, lobatamide A, lobatamide B, lobatamide C, lobatamide D, lobatamide E, and lobatamide F.

The aforementioned "seed" compound, the positive control compound, and the test compounds were each formulated in DMSO and complete medium, and the resulting compositions were subjected contemporaneously to the NCI 60 cell-line testing procedure as described in Example 4. Each compound was tested in quadruplicate using an upper concentration limit of $10^{-6}$ molar, and 1 $\log_{10}$ dilutions. Resulting data for each compound were used to construct the corresponding mean-graph "fingerprints", and a COMPARE correlation analysis was performed as described further below.

Figure 12A:
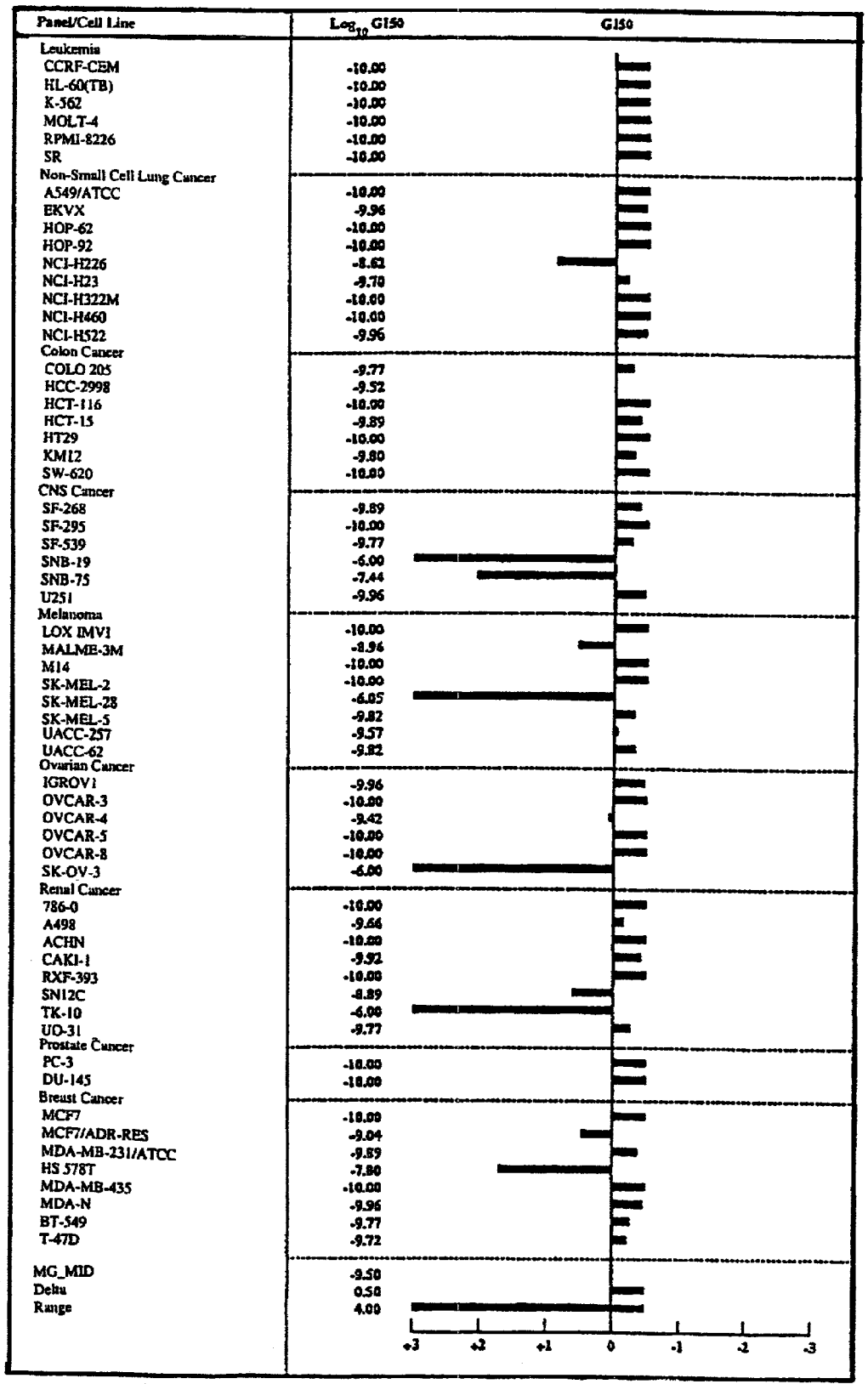
FIG. 12A illustrates the $GI_{50}$-based mean-graph "fingerprint" of concanamycin A in the NCI 60 cell-line screen.
Figure 12B:
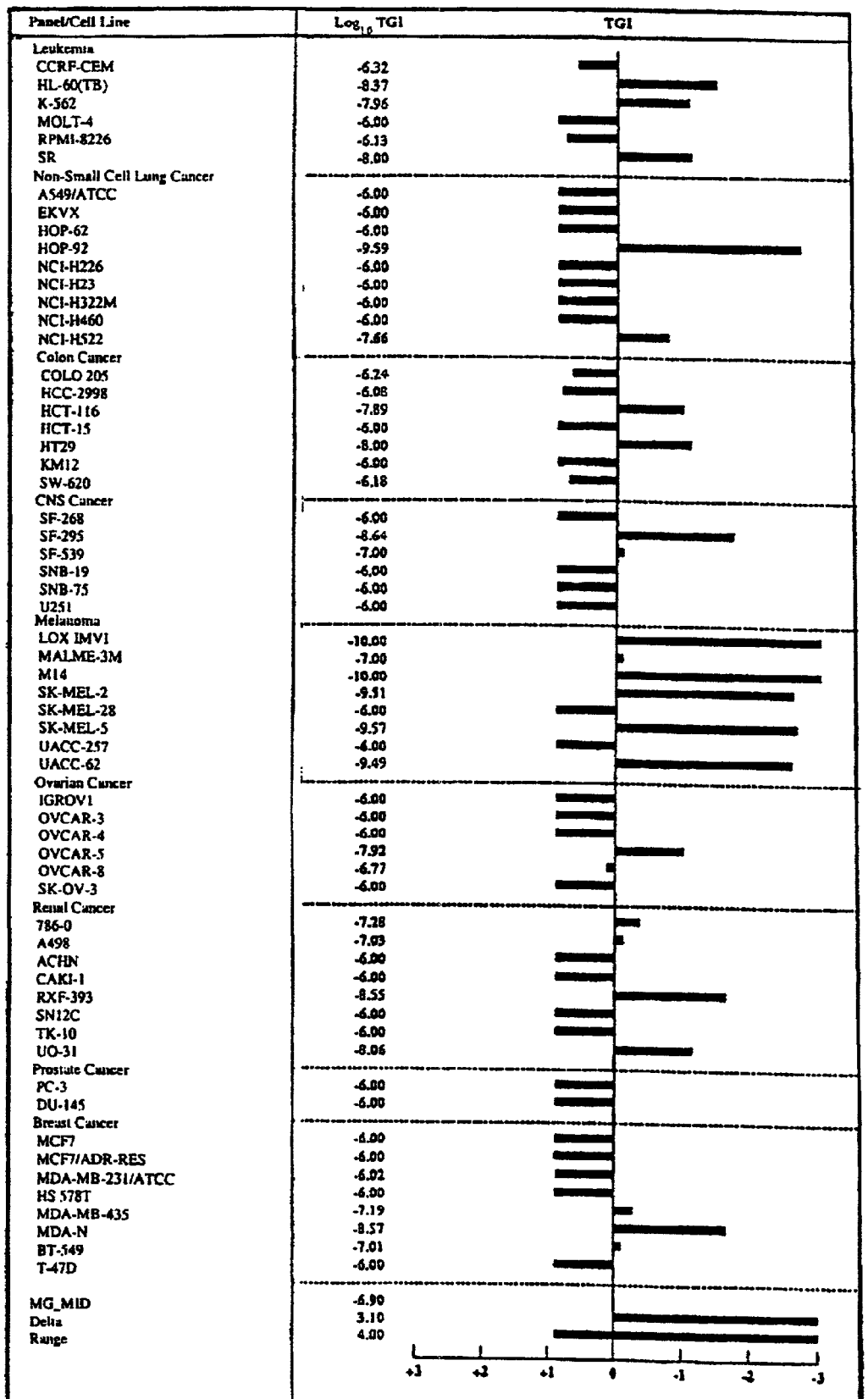
FIG. 12B illustrates the TGI-based mean-graph "fingerprint" of concanamycin A in the NCI 60 cell-line screen.
Figure 12C:
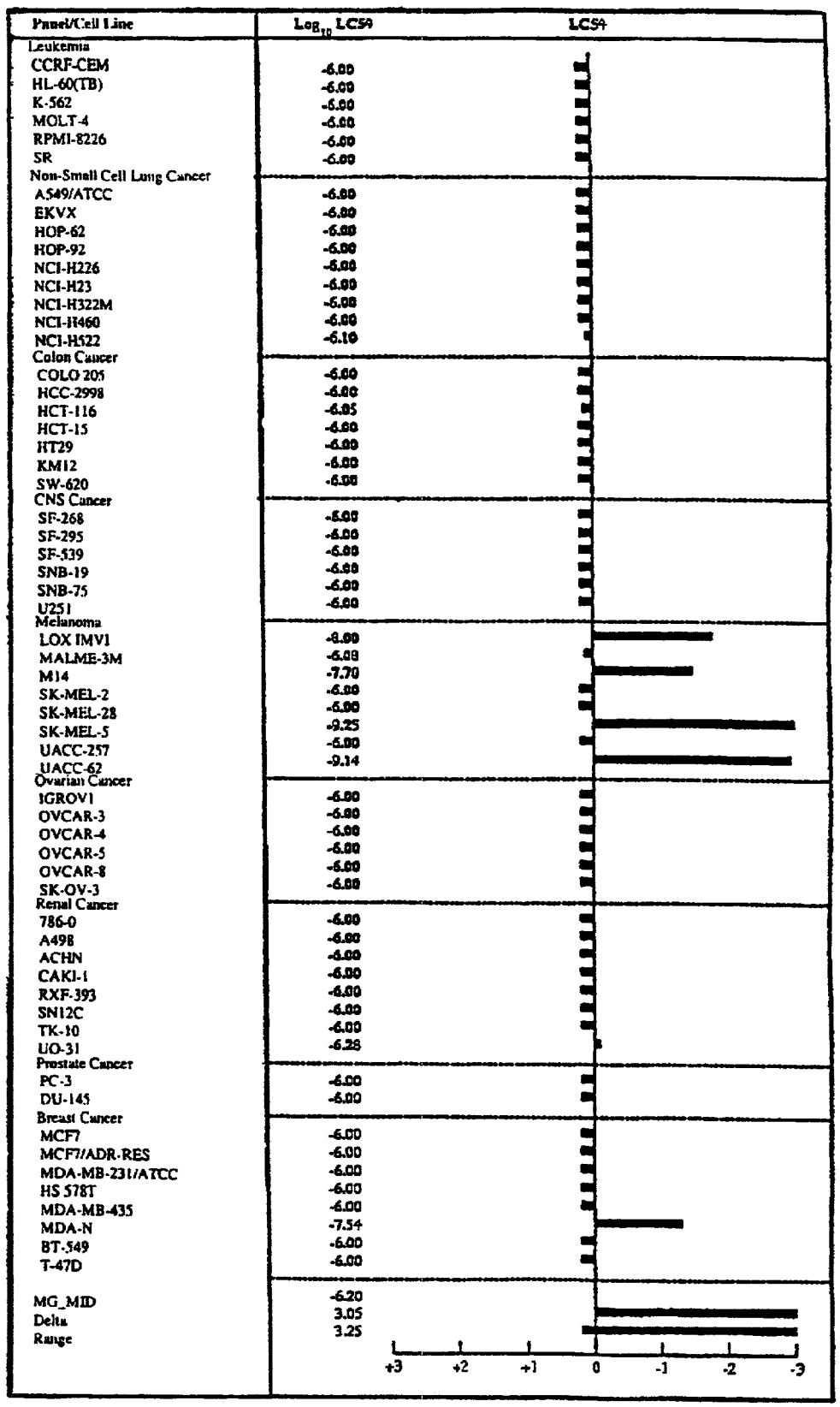
FIG. 12C illustrates the $LC_{50}$-based mean-graph "fingerprint" of concanamycin A in the NCI 60 cell-line screen.

FIGS. 12A-12C illustrate the $GI_{50}$, TGI and $LC_{50}$ mean-graph "fingerprints," respectively, of the mechanistic prototype (or "seed") compound, concanamycin A. The database that was used in this example, and that was searched using a concanamycin A "seed" comprised, in addition to the mean-graph "fingerprints" obtained from the contemporaneous testing of the aforementioned compounds (i.e., the selected "seed" compound, positive control and test compounds), more than 8000 mean-graph "fingerprints" from the prior testing of structurally diverse pure compounds. The database also comprised the mean-graph "fingerprints" obtained from crude extracts and partially purified fractions thereof, unrelated to the "seed" compound, or to the positive control or test compounds of the present invention, or to extracts or fractions having any known or suspected content of any of the aforementioned compounds.

As appropriate for this demonstration, the TGI mean-graph, derived from the contemporaneous testing of concanamycin A (FIG. 12B), was used as the "seed" to search against the TGI mean-graphs contained in the aforementioned database, and as the basis for calculation of the COMPARE coefficients. The $GI_{50}$ mean-graphs of each compound tested in the present study were used for the calculation of mean panel $GI_{50}$ values.

Table 7 summarizes the TGI-COMPARE correlation coefficients and mean-panel $GI_{50}$ values from the testing of concanamycin A, bafilomycin $A_1$, salicylihalamide A and lobatamides A-F in the NCI 60 cell-line screen. The mean-panel $GI_{50}$ values are also shown in Table 7. The COMPARE correlations shown in Table 7 were performed using the TGI mean-graph of concanamycin A as the "seed."

TABLE 7

| Compound | TGI-COMPARE correlation coefficient | Mean-Panel $GI_{50}$ ($\times 10^{-9}$ M) | ($\pm$ S.D.) |
|---|---|---|---|
| concanamycin A | 1.00 | 0.33 | (0.04) |
| bafilomycin $A_1$ | 0.96 | 4.6 | (1.7) |
| salicylihalamide A | 0.83 | 33.0 | (23.0) |
| lobatamide A | 0.91 | 4.8 | (1.7) |
| lobatamide B | 0.89 | 0.73 | (0.24) |
| lobatamide C | 0.89 | 2.5 | (1.5) |
| lobatamide D | 0.92 | 1.1 | (0.33) |

TABLE 7-continued

| Compound | TGI-COMPARE correlation coefficient | Mean-Panel GI$_{50}$ (× 10$^{-9}$ M) | (± S.D.) |
|---|---|---|---|
| lobatamide E | 0.89 | 1.3 | (1.0) |
| lobatamide F | 0.95 | 10.0 | (3.0) |

As shown by the expected perfect correlation (COM-PARE correlation coefficient, 1.0) of the seed compound (concanamycin A) with itself, the computer-based algorithm analysis was working properly and precisely for this demonstration. Moreover, the positive control compound, bafilomycin A$_1$, showed a correlation with the seed compound of approximately 0.96, confirming that this analysis could correctly identify compounds which, although structurally distinct from the seed, nonetheless share the same molecular target (i.e., in this instance, vacuolar-type (H+)-ATPase). Most notably, all of the selected test compounds in the present example showed, in reference to the "seed", COM-PARE correlation coefficients of at least 0.85 or higher, thus demonstrating that their molecular target is likewise vacuolar-type (H+)-ATPase. Indeed remarkably, when the >8000 "fingerprints", comprising the database searched in this analysis, were ordered from highest to lowest correlation with the seed, the top seven matches were lobatamide A, lobatamide B, lobatamide C, lobatamide D, lobatamide E, lobatamide F, and salicylihalamide A. The mean-panel GI$_{50}$ values suggest that the compounds of the present invention may exhibit a range of relative absolute potencies against vacuolar-type (H+)-ATPase.

In a further iteration of the COMPARE analysis as used in this demonstration, the mean-graph "fingerprint" of lobatamide D was instead used as the "seed" to search the aforementioned database. The results of this further iteration of the COMPARE analyses are shown below in Table 8, which shows the TGI-COMPARE correlation coefficients from the testing of concanamycin A, bafilomycin A$_1$, salicylihalamide A and lobatamides A-D in the NCI 60 cell-line screen. The COMPARE correlations shown in Table 8 were performed using the TGI mean-graph of lobatamide D as the "seed."

TABLE 8

| Compound | TGI-COMPARE correlation coefficient |
|---|---|
| concanamycin A | 0.92 |
| bafilomycin A$_1$ | 0.94 |
| salicylihalamide A | 0.90 |
| lobatamide A | 0.92 |
| lobatamide B | 0.94 |
| lobatamide C | 0.97 |
| lobatamide D | 1.00 |
| lobatamide E | 0.95 |
| lobatamide F | 0.97 |

In this case, the obtained correlation coefficients were even higher, ranging from 0.90 (salicylihalamide A) to 0.97 (lobatamide C and lobatamide F), further confirming that all of the compounds tested in this example share the same molecular target, vacuolar-type (H+)-ATPase. Thus, the tested compounds of the present invention are approximately at least as potent as the most potent heretofore known vacuolar-type (H+)-ATPase inhibitors. The compounds of the present invention are advantageous in that they are structurally far less complex than the concanamycins or the bafilomycins (see, e.g., FIGS. 11A and 11B), thereby providing easier synthetic access to the compounds of the present invention by synthetic methods which are known to those of skill in the art.

Example 6

This example demonstrates the vacuolar-type (H+)-ATPase inhibitory activity of salicylihalamide A and lobatamide A using representative human vacuolar-type (H+)-ATPase inhibition assays.

Inhibition of bafilomycin-sensitive vacuolar-type (H+)-ATPase activity was measured in partially purified membrane vesicle preparations from human osteoclastoma cells (hOc), human renal cortical cells (hK), and macrophage cells (J774). The vesicles were prepared by appropriate adaptations of methods described in Gagliardi et al., *J. Med. Chem.*, 41, 1568-1573 (1998); and Gagliardi et al., *J. Med. Chem.*, 41, 1883-1893 (1998).

Vacuolar-type (H+)-ATPase assays were performed in the presence of oligomycin (5 µg/ml) and vanadate (1 mM) as inhibitors of F- and P-ATPases, respectively. A calorimetric method was used to quantitate the residual bafilomycin-sensitive vacuolar-type (H+)-ATPase activity (see Chan et al., *Anal. Biochem.*, 157, 375-380 (1986)). The assay measures the release of inorganic phosphate from ATP at 37° during 30 minutes of incubation. The reaction is initiated by the addition of MgSO$_4$ (5 M final concentration).

The inhibitory activities for salicylihalamide A and lobatamide A against vacuolar-type (H+)-ATPase derived from human osteoclastoma cells (hOc), human kidney cells (hK), and macrophage cells (J774) are shown below in Table 9.

TABLE 9

| COMPOUND | IC$_{50}$ (nM) | | |
|---|---|---|---|
| | hOc | hk | J774 |
| Salicylihalamide A | 0.6 | 0.3 | 2.8 |
| Lobatamide A | 7.6 | 1.8 | 2.8 |

The foregoing data provide yet another confirmation that salicylihalamide A and lobatamide A are potent vacuolar-type (H+)-ATPase inhibitors, with IC$_{50}$'s in the nanomolar to sub-nanomolar range.

Moreover, salicylihalamide A and lobatamide A, in marked contrast to the "prototypical" vacuolar-type (H+)-ATPase inhibitors, concanamycins and bafilomycins, have been found to be highly selective inhibitors of mammalian vacuolar-type (H+)-ATPase. Salicylihalamide A and folimycin (concanamycin A) were tested side-by-side for inhibitory activity against mammalian vacuolar-type (H+)-ATPase (from chromaffin granule membranes) and fungal vacuolar-type (H+)-ATPase (from *Neurospora crassa*). The inhibitory data were obtained using the same procedures and biological preparations described in Bowman et al., *Proc. Natl. Acad. Sci. USA*, 85, 7972-7976 (November 1988). The data obtained thereby confirmed that folimycin is a potent inhibitor of both the mammalian and fungal enzymes, whereas salicylihalamide A, which also proved to be a potent inhibitor of the mammalian enzyme, had little or no inhibitory activity against the fungal enzyme. The same type of selectivity for mammalian vacuolar-type (H+)-ATPase also was observed for lobatamide A. These results demonstrate that the salicylihalamides and lobatamides of the present invention operate by a mechanism that is markedly different than that of known "prototypical" inhibitors. These results further demonstrate that the salicylihalamides and lobatamides of the present invention have unprecedented selectivity toward mammalian isoforms of vacuolar-type (H+)-ATPase.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

The invention claimed is:

1. A method of treating a condition treatable by the inhibition of vacuolar-type (H+)-ATPase, said method comprising administering to a patient in need thereof an amount effective to inhibit vacuolar-type (H+)-ATPase of at least one compound of the formula:

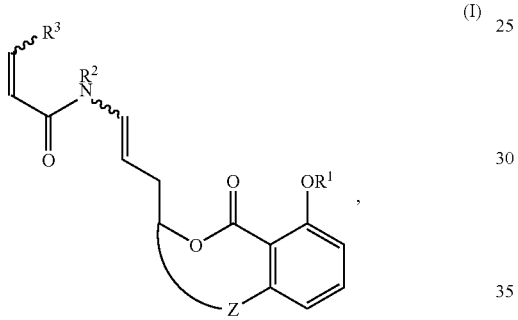

wherein
- $R^1$ and $R^2$ are the same or different and each is H, a straight-chain or branched saturated or unsaturated alkyl, an aryl, $R^6CH_2$—, $R^6CO$—, or $R^6SO_2$—, wherein $R^6$ is H, a straight-chain or branched saturated or unsaturated alkyl, or an aryl;
- $R^3$ is H, a straight-chain or branched saturated or unsaturated alkyl, an aryl, an oxime, or an oxime methyl ether;
- the aromatic ring of formula (I) is unsubstituted or substituted with at least one substituent selected from the group consisting of a halogen, a nitro, an amino, a hydroxyl, a thio, an acyl, an alkyl, and a cyano;
- the saturated alkyl, unsaturated alkyl and aryl substituents defined in any one or more of $R^1$, $R^2$, $R^3$, or $R^6$ are unsubstituted or substituted with at least one substituent selected from the group consisting of a halogen, a nitro, an amino, a hydroxyl, a thio, an acyl, an alkyl, and a cyano; and
- Z is a contiguous linker comprising a chain of 7-10 carbon atoms which, together with the five atoms beginning with the carbon of the aromatic ring of formula (I) in meta-relationship with $OR^1$ and ending with the carbon directly attached to the alkyl oxygen of the lactone of formula (I), said carbons being covalently bonded to either end of linker Z, integrally form a 12-15 membered ring;

or a pharmaceutically acceptable salt, an ester, or a prodrug thereof, wherein the condition is osteoporosis.

2. The method of claim 1, wherein said compound is selected from the group consisting of:

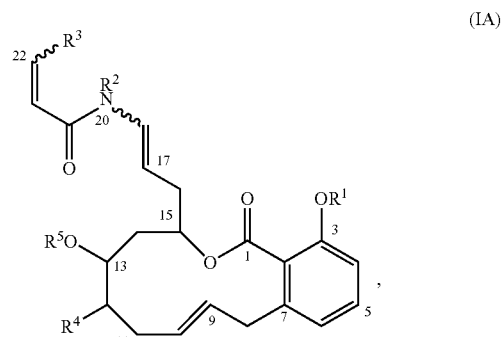

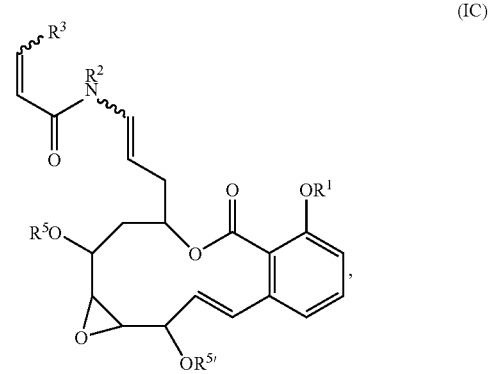

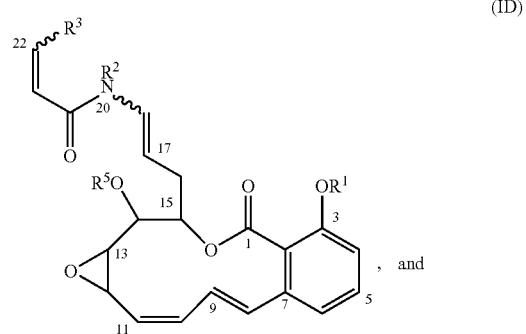

, and

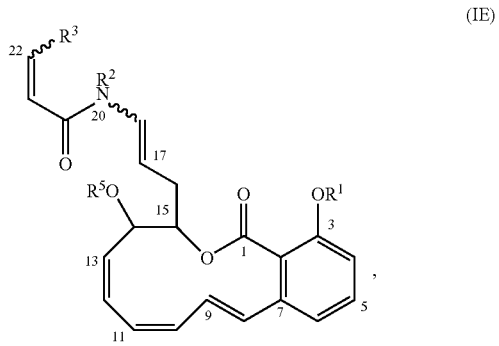

, wherein
- R¹ and R² are the same or different and each is H, a straight-chain or branched saturated or unsaturated alkyl, an aryl, R⁶CH₂—, R⁶CO—, or R⁶SO₂—, wherein R⁶ is H, a straight-chain or branched saturated or unsaturated alkyl, or an aryl;
- R³ is H, a straight-chain or branched saturated or unsaturated alkyl, an aryl, an oxime, or an oxime methyl ether;
- R⁴ is H, an alkyl, or R⁷CH₂—, wherein R⁷ is R⁶O—, R⁶CO₂—, or R⁶SO₃—;
- R⁵ and R⁵' are the same or different and each is H, a straight-chain or branched saturated or unsaturated alkyl, an aryl, a glycoside, R⁶CH₂—, R⁶CO—, or R⁶SO₂—;
- the saturated alkyl, unsaturated alkyl and aryl defined in any one or more of R¹, R², R³, R⁵, R⁵' or R⁶, and the alkyl defined in R⁴, are unsubstituted or substituted with at least one substituent selected from the group consisting of a halogen, a nitro, an amino, a hydroxyl, a thio, an acyl, an alkyl, and a cyano; and
- the aromatic ring of formula (I) is unsubstituted or substituted with at least one substituent selected from the group consisting of a halogen, a nitro, an amino, a hydroxyl, a thio, an acyl, an alkyl, and a cyano;
- or a pharmaceutically acceptable salt, an ester, or a prodrug thereof.

3. The method of claim 2, wherein said compound is selected from the group consisting of:

salicylihalamide A salicylihalamide B

CJ-12,950

CJ-13,357 oximidine 1 oximidine 2 or a pharmaceutically acceptable salt, an ester, or a prodrug thereof.

4. The method of claim 1, which further comprises co-administering to a patient in need thereof a therapeutically effective amount of at least one additional compound other than a compound defined in claim 1.

5. The method of claim 4, wherein said additional compound is selected from the group consisting of bafilomycins and concanamycins.

6. The method of claim 5, wherein said additional compound is concanamycin A.

7. The method of claim 5, wherein said additional compound is bafilomycin $A_1$.

8. The method of claim 1, wherein said vacuolar-type (H+)-ATPase inhibiting-effective amount is effective to inhibit intra-organellar acidification of intracellular organelles.

9. The method of claim 1, wherein said vacuolar-type (H+)-ATPase inhibiting-effective amount is effective to treat osteoporosis.

10. A method of treating a condition treatable by the inhibition of vacuolar-type (H+)-ATPase, said method comprising administering to a patient in need thereof an amount effective to inhibit vacuolar-type (H+)-ATPase of at least one compound of the formula:

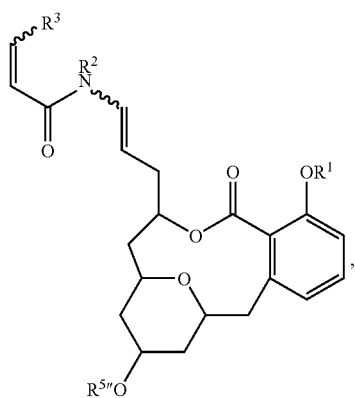

(IF)

wherein
$R^1$-$R^3$ are as defined in claim 1 and
$R^{5''}$ is H, a straight-chain or branched saturated or unsaturated alkyl, an aryl, a glycoside, $R^6CH_2$—, $R^6CO$—, or $R^6SO_2$—, wherein $R^6$ is as defined in claim 1 and
the saturated alkyl, unsaturated alkyl and aryl defined in $R^{5''}$ are unsubstituted or substituted with at least one substituent selected from the group consisting of a halogen, a nitro, an amino, a hydroxyl, a thio, an acyl, an alkyl, and a cyano,
wherein the condition is osteoporosis.

11. The method of claim 10, wherein said compound is selected from the group consisting of:

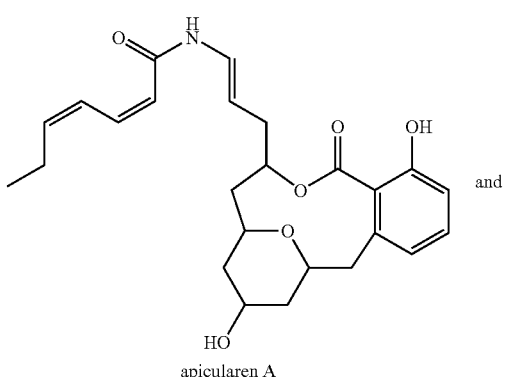

apicularen A and

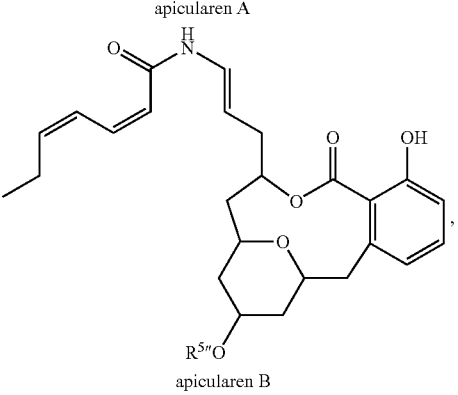

apicularen B wherein $R^{5''}$ is N-acetyl-β-D-glucosamine.

* * * * *